United States Patent
Burkhart et al.

(10) Patent No.: US 11,912,736 B2
(45) Date of Patent: Feb. 27, 2024

(54) DIARYL TREHALOSE COMPOUNDS AND USES THEREOF

(71) Applicant: THE UNIVERSITY OF MONTANA, Missoula, MT (US)

(72) Inventors: David Burkhart, Missoula, MT (US); George Ettenger, Missoula, MT (US); Jay Evans, Corvallis, MT (US); Kendal T. Ryter, Hamilton, MT (US); Alyson Smith, Bonner, MT (US)

(73) Assignee: THE UNIVERSITY OF MONTANA, Missoula, MT (US)

( * ) Notice: Subject to any disclaimer, the term of this patent is extended or adjusted under 35 U.S.C. 154(b) by 6 days.

(21) Appl. No.: 16/968,075

(22) PCT Filed: Feb. 21, 2019

(86) PCT No.: PCT/US2019/019012
§ 371 (c)(1),
(2) Date: Aug. 6, 2020

(87) PCT Pub. No.: WO2019/165114
PCT Pub. Date: Aug. 29, 2019

(65) Prior Publication Data
US 2021/0139521 A1  May 13, 2021

Related U.S. Application Data

(60) Provisional application No. 62/633,375, filed on Feb. 21, 2018.

(51) Int. Cl.
*C07H 13/08* (2006.01)
*A61P 37/04* (2006.01)
*A61K 39/04* (2006.01)
*A61K 39/39* (2006.01)
*C07H 15/04* (2006.01)

(52) U.S. Cl.
CPC ............. *C07H 13/08* (2013.01); *A61K 39/04* (2013.01); *A61K 39/39* (2013.01); *A61P 37/04* (2018.01); *C07H 15/04* (2013.01)

(58) Field of Classification Search
None
See application file for complete search history.

(56) References Cited

U.S. PATENT DOCUMENTS

| | | |
|---|---|---|
| 4,603,112 A | 7/1986 | Paoletti et al. |
| 4,751,180 A | 6/1988 | Cousens et al. |
| 4,769,330 A | 9/1988 | Paoletti et al. |
| 4,777,127 A | 10/1988 | Suni et al. |
| 4,935,233 A | 6/1990 | Bell et al. |
| 5,017,487 A | 5/1991 | Stunnenberg et al. |
| 5,151,254 A | 9/1992 | Arai et al. |
| 5,891,475 A | 4/1999 | Perrin et al. |
| 6,113,918 A | 9/2000 | Johnson et al. |
| 6,342,226 B1 | 1/2002 | Betbeder et al. |
| 8,741,871 B2 * | 6/2014 | Nishizawa ............ A61P 37/04 514/53 |
| 2011/0218171 A1 | 9/2011 | Nishizawa et al. |
| 2013/0331346 A1 | 12/2013 | Liu et al. |
| 2014/0112979 A1 | 4/2014 | Andreasen et al. |

FOREIGN PATENT DOCUMENTS

| | | |
|---|---|---|
| CN | 102260297 A | 11/2011 |
| EP | 0345242 A2 | 12/1989 |
| GB | 2200651 A | 8/1988 |
| JP | 2021-501791 A | 1/2021 |
| WO | 8901973 A2 | 3/1989 |
| WO | 9100904 A1 | 1/1991 |
| WO | 9102805 A2 | 3/1991 |
| WO | 9420078 A1 | 9/1994 |
| WO | 9423701 A1 | 10/1994 |
| WO | 9606638 A1 | 3/1996 |
| WO | 9724447 A1 | 7/1997 |
| WO | 9850399 A1 | 11/1998 |
| WO | 2019088854 A1 | 5/2019 |

OTHER PUBLICATIONS

Banchereau et al., "Dendritic cells and the control of immunity", Nature, vol. 392, 1998, pp. 245-251.
Berkner, "Development of adenovirus vectors for the expression of heterologous genes", Biotechniques, vol. 6, 1988, pp. 616-627.
Coombes et al., "Single dose, polymeric, microparticle-based vaccines: the influence of formulation conditions on the magnitude and duration of the immune response to a protein antigen", Vaccine, 1996, vol. 14, No. 15, pp. 1429-1438.
Dalsgaard, "A study of the Isolation and Characterization of the Saponin Quil A: Evaluation of its Adjuvant Activity, with a special reference to the application in the vaccination of cattle against foot-and-mouth disease", Acta Veterinaria Scandinavica, vol. 69, 1978, pp. 1-40.
Fischer-Hoch et al., "Protection of rhesus monkeys from fatal Lassa fever by vaccination with a recombinant vaccinia virus containing the Lass virus glycoprotein gene", Proc. Natl. Acad. Sci., vol. 86, 1989, pp. 317-321.
Moss et al., "Vaccinia Virus Expression Vectors", Ann. NY Acad Sci, vol. 569, 1989, pp. 86-103.
Flexner et al., "Attenuation and immmunogenicty in primates of vaccinia virus recombinants expressing human interleukin-2", Vaccine, vol. 8, 1990, pp. 17-21.
Foster et al., "Lipidated brartemicin analogues are potent Th1-stimulating vaccine adjuvants", Journal of Medicinal Chemistry, 2018, pp. 1045-1060.

(Continued)

*Primary Examiner* — Layla D Berry
(74) *Attorney, Agent, or Firm* — Michael Best & Friedrich LLP

(57) ABSTRACT

Disclosed herein are diaryl trehalose compounds and methods of use thereof, for example as vaccine adjuvants.

19 Claims, 21 Drawing Sheets

(56) References Cited

OTHER PUBLICATIONS

Guzman et al., "Efficient Gene Transfer Into Myocardium by Direct Injection of Adenovirus Vectors", Cir. Res, vol. 73, 1993, pp. 1202-1207.

Guzman et al., "Efficient and Selective Adenovirus-Mediated Gene Transfer Into Vascular Neointima", Circulation, vol. 88, 1993, pp. 2838-2848.

Kass-Eiseler et al., "Quantitative determination of adenovirus-mediated gene delivery to rat cardiac myocytes in vitro and in vivo", Proc. Natl. Acad. Sci., vol. 90, 1993, pp. 11498-11502.

Kolls et al., "Prolonged and effective blockade of tumor necrosis factor activity through adenovirus-mediated gene transfer", Proc. Natl. Acad. Sci., vol. 91, 1994, pp. 215-219.

Mahvi et al., "DNA cancer vaccines: A gene gun approach", Immunology and Cell Biology, vol. 75, 1997, pp. 456-460.

Maratea et al., "Deletion and fusion analysis of the phage phi-X174 lysis gene E", Gene, vol. 40, 1985, pp. 39-46.

Merrifield, "Solid Phase Peptide Synthesis. I. The Synthesis of a Tetrapeptide", J. Am. Chem. Soc. Vol. 85, 1963, pp. 2149-2154.

Mosmann et al., "TH1 and TH2 Cells: Different Patterns of Lymphokine Secretion Lead to Different Functional Properties", Ann. Rev. Immunol., vol. 7, 1989, pp. 145-173.

Rolland, "From Genes to Gene Medicines: Recent Advances in Nonviral Gene Delivery", Crit Rev Therap Drug Carrier Systems, vol. 15, No. 2, 1998, pp. 143-198.

Rosenfeld et al., "Adenovirus-Mediated Transfer of a Recombinant alpha1-Antitrypsin Gene to the Lung Epithelium in Vivo", Science, vol. 252, 1991, pp. 431-434.

Sela, "Antigenicity: Some Molecular Aspects", Science. vol. 166, 1969, pp. 1365-1374.

Timmerman et al., "Dendritic Cell Vaccines for Cancer Immunotherapy", Ann. Rev. Med., vol. 50, 1999, pp. 507-529.

Ulmer et al., "Heterologous Protection Against Influenza by Injection of DNA Encoding a Viral Protein", Science, vol. 259, 1993, pp. 1745-1749.

Zitvogel et al., "Eradication of established murine tumors using a novel cell-free vaccine: dendritic cell-derived exosomes", Nature Med., vol. 4, 1998, pp. 594-600.

International Search Report and Written Opinion for Application No. PCT/US2019/019012 dated Jun. 14, 2019 (13 pages).

Liu et al., "Effect of Displacer Chemistry on Displacer Efficacy for a Sguar Based Anion Exchange Displacer Library", Ind. Eng. Chem. Res., vol. 45, 2006, pp. 9107-9114.

Johnson et al., "An Efficient Synthesis of 6,6'-DI-O-Acylated alpha, alpha-Trehaloses", J. Carbohydrate Chemistry, 1998, vol. 17, No. 6, pp. 969-974.

PubChem SID 274998933, Dec. 2015, 4 pages.

Jacobsen et al., "The natural product brartemicin is a high affinity ligand for the carbohydrate-recognition domain of the macrophage receptor mincle", Med. Chem. Commun, vol. 6, 2015, pp. 647-652.

Jiang et al., "Synthesis and structure-activity relationships studies of brartemicin analogs as anti-invasive agents", The Journal of Antibiotics, 2013, vol. 66, pp. 531-537.

Jiang et al., "Synthesis and evaluation of trehalose-based compounds as anti-invasive agents", Bioorganic and Medicinal Chemistry Letters, vol. 21, 2011, pp. 1089-1091.

Jiang et al., "Synthesis and Evaluation of trehalose-based compounds as Novel Inhibitors of Cancer Cell Migration and Invasion", Chem Biol Drug Des, 2015, vol. 86, pp. 1017-1029.

European Patent Office Extended Search Report for Application No. 19787211.8 dated Oct. 27, 2021 (10 pages).

Ter Haar et al., "Proof of prinicple for the synthesis of hydroxy-aryl esters of glycosidic polyols and non-reducing oligosaccharides with subsequent enzymatic coupling to a tyrosine-containing tripeptide", Carbohydrate Research, 2011, vol. 346, pp. 1005-1012.

Gensler et al., "Synthesis and Immunomodulating Tumor Control Properties of Albumin Covalently Connected to Trehalose", Cancer Immunol. Immunother., 1980, vol. 9, pp. 101-109.

Joshi et al., "Simalin A and B: Two new aromatic compounds from the stem bark of Bombax ceiba", Phytochemistry etters, 2014, vol. 7, pp. 26-29.

Berndt et al., "Covalent linkage of N-methyl-6-oxyquinolinium betaine to trehalose", Carbohydrate Research, 2011, vol. 346, pp. 2960-2964.

Oliveri et al., "Soluble Sugar-Based Quinoline Derivatives as New Antioxidant Modulators of Metal-Induced Amyloid Aggregation", Inorganic Chemistry, 2015, vol. 54, pp. 2591-2602.

Igarashi et al., "Brartemicin, an Inhibitor of Tumor Cell Invasion from the Actinomycete *Nonomuraea* sp", J. Nat. Prod, 2009, vol. 72, pp. 980-982.

Li, S. et al. "Inhibitory effects of compound DMBT on hypoxia-induced vasculogenic mimicry in human breast cancer." Biomedicine & Pharmacotherapy 96 (2017): 982-992.

Liav, A. et al. "Synthesis of 6, 6'-di-O-acylated α, α-trehaloses via 2, 3, 4, 2', 3', 4'-hexa-O-benzyl-α, α-trehalose." Carbohydrate Research 81.1 (1980): c1-c3.

Liav, A. et al. "Diamide pseudo cord-factors: bis-N-acyl derivatives of 6, 6'-diamino-6, 6'-dideoxy-α, α-trehalose." Carbohydrate Research 94.2 (1981): 230-235.

Japanese Office Action for application 2020-544485, dated Nov. 30, 2022, 10 pages with translation.

* cited by examiner

DIARYL TREHALOSE COMPOUNDS AND USES THEREOF

CROSS-REFERENCE TO RELATED APPLICATIONS

This application is a U.S. national stage entry of International Patent Application No. PCT/US2019/019012, filed on Feb. 21, 2019, which claims priority to U.S. Provisional Patent Application No. 62/633,375, filed on Feb. 21, 2018, the entire contents of each of which are fully incorporated herein by reference.

STATEMENT OF GOVERNMENT INTEREST

This invention was made with government support under contract number HHSN272201400050C awarded by the National Institutes of Health. The government has certain rights in the invention.

TECHNICAL FIELD

The present disclosure relates to diaryl trehalose (DAT) compounds and methods of use thereof, for example as vaccine adjuvants.

BACKGROUND

Globally, there are a number of disease-causing pathogens for which limited to no prophylaxis is available. Among these diseases, many fall into a class of bacterial and fungal pathogens for which Th17 mediated immunity has been implicated in disease protection, including *Mycobacterium tuberculosis* (Mtb), *Staphylococcus aureus, Pseudomonas aeruginosa, Streptococcus pneumonia, Candida albicans, Aspergillus fumigatus*, and others. While antigens are available for some of these pathogens, the development of Th17-inducing adjuvants has lagged. Currently adjuvant systems available and approved for humans induce primarily either a Th2 (aluminum salts) or Th1 (MPL) type response.

Currently, the only adjuvant available for human use that promotes a Th17-mediated immune response is CAF01. This adjuvant is a cationic liposome that includes a synthetic Mincle receptor ligand (trehalose dibehenate) formulated with dimethyldioctadecylammonium. However, this adjuvant has not progressed beyond Phase I clinical trials.

Additional adjuvants with improved efficacy and safety attributes are needed to advance new vaccines and therapeutics in the areas of infectious disease, as well as autoimmunity and cancer.

SUMMARY

In one aspect, disclosed are compounds of formula (I):

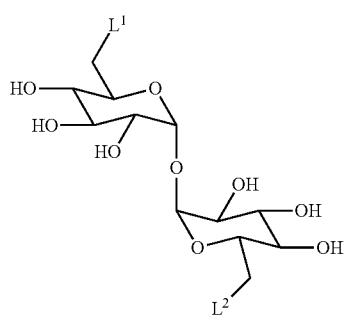

(I)

or a pharmaceutically acceptable salt thereof, wherein
$L^1$ is —OH or —X(CR$^{1a}$R$^{1a'}$)$_m$O$_p$Ar$^1$;
$L^2$ is —Y(CR$^{2a}$R$^{2a'}$)$_n$O$_q$Ar$^2$;
X and Y are each independently selected from —OC(O)—, —NR$^a$C(O)—, —NR$^b$C(S)—, —NR$^c$—, —SO$_2$NR$^c$—, —O—, and —OC(O)CH=CH—;
R$^a$, R$^b$, and R$^c$ are each independently selected from hydrogen and C$_1$-C$_4$ alkyl;
m is 0, 1 or 2;
n is 0, 1 or 2;
R$^{1a}$, R$^{1a'}$, R$^{2a}$, and R$^{2a'}$, when present, are each independently selected from hydrogen and C$_1$-C$_4$ alkyl;
p is 0 or 1;
q is 0 or 1;
Ar$^1$ and Ar$^2$ are each independently selected from aryl or heteroaryl, wherein each aryl or heteroaryl may be independently substituted or unsubstituted with 1, 2, 3, 4, or 5 substituents independently selected from hydrogen, C$_1$-C$_{12}$-alkyl, hydroxy, C$_1$-C$_{12}$-alkoxy, halo, C$_1$-C$_4$ haloalkyl, Ar$^3$, C$_1$-C$_8$-alkoxy-C$_1$-C$_8$-alkoxy, C$_1$-C$_8$-alkoxy-C$_1$-C$_8$-alkyl, hydroxy-C$_1$-C$_8$-alkyl, amino, nitro, —NH—Ar$^4$, C$_1$-C$_8$-alkoxy-Ar$^5$, C$_1$-C$_8$-alkylsulfonyl, and C$_1$-C$_8$-alkoxy-C$_1$-C$_8$-alkoxy-C$_1$-C$_8$-alkoxy, or the substituents, together with the atoms to which they are attached, are optionally taken together to form an aryl ring; wherein each heteroaryl may include 1, 2, 3, 4, or 5 heteroatoms selected from O, S or N;
Ar$^3$, Ar$^4$ and Ar$^5$ are each independently selected from aryl or heteroaryl independently unsubstituted or substituted with 1, 2, 3, or 4 substituents independently selected from C$_1$-C$_4$-alkyl, hydroxy, C$_1$-C$_4$-alkoxy, halo, C$_1$-C$_4$ haloalkyl, and C$_1$-C$_4$ hydroxyalkyl; and
wherein the compound is not:
6,6'-bis(2-methoxybenzoyl)-α,α-D-trehalose,
6,6'-bis(benzoylamino)-α,α-D-trehalose,
6,6'-bis(2-hydroxybenzoyl)-α,α-D-trehalose,
6,6'-bis(2-hydroxybenzoylamino)-α,α-D-trehalose,
6,6'-bis(2-methylbenzoyl)-α,α-D-trehalose,
6,6'-bis(2-methylbenzoylamino)-α,α-D-trehalose,
6,6'-bis(4-methoxybenzoyl)-α,α-D-trehalose,
6,6'-bis(4-methoxybenzoylamino)-α,α-D-trehalose,
6,6'-bis(4-hydroxybenzoyl)-α,α-D-trehalose,
6,6'-bis(4-hydroxybenzoylamino)-α,α-D-trehalose,
6,6'-bis(4-benzyloxybenzoyl)-α,α-D-trehalose,
6,6'-bis(2,3-dimethoxybenzoyl)-α,α-D-trehalose,
6,6'-bis(2,3-dimethoxybenzoylamino)-α,α-D-trehalose,
6,6'-bis(2,6-difluorobenzoyl)-α,α-D-trehalose,
6,6'-bis(2,6-difluorobenzoylamino)-α,α-D-trehalose,
6,6'-bis(2,6-dichlorobenzoyl)-α,α-D-trehalose,
6,6'-bis(2,3-dihydroxybenzoyl)-α,α-D-trehalose,
6,6'-bis(2,4-dihydroxybenzoyl)-α,α-D-trehalose,
6,6'-bis(2,4-dihydroxybenzoylamino)-α,α-D-trehalose,
6,6'-bis(2,3-dibenzyloxybenzoyl)-α,α-D-trehalose,
6,6'-bis(2-hydroxy-3-methoxybenzoyl)-α,α-D-trehalose,
6,6'-bis(2-benzyloxy-3-methoxybenzoyl)-α,α-D-trehalose,
6,6'-bis(2-methyl-6-aminobenzoyl)-α,α-D-trehalose,
6,6'-bis(3-methoxy-4-fluorobenzoyl)-α,α-D-trehalose,
6,6'-bis(3,4,5-trimethoxybenzoyl)-α,α-D-trehalose,
6,6'-bis(3,4,5-trimethoxybenzoylamino)-α,α-D-trehalose,
6,6'-bis(2,4-dihydroxy-6-methylbenzoyl)-α,α-D-trehalose,
6,6'-bis(2,4-dimethoxy-6-methylbenzoyl)-α,α-D-trehalose,
6,6'-bis(2-hydroxy-4-n-heptyloxybenzoyl)-α,α-D-trehalose,
6,6'-bis(2-hydroxy-4-n-pentyloxybenzoyl)-α,α-D-trehalose,
6,6'-bis(2-hydroxy-4-methoxybenzoyl)-α,α-D-trehalose,
6,6'-bis(4-n-pentyloxybenzoyl)-α,α-D-trehalose,
6,6'-bis(2,4-dihydroxy-6-methylbenzoyl)-α,α-D-trehalose, 6,6'-bis(cinnamoylamino)-α,α-D-trehalose,
6,6'-bis(3,4-dimethoxycinnamoylamino)-α,α-D-trehalose,
6,6'-bis(isonicotinoylamino)-α,α-D-trehalose, or
6,6'-bis(pyrazine-2-carbonylamino)-α,α-D-trehalose.

Also disclosed herein are compounds of formula (Ia), (Ib), compounds of formula (II) and pharmaceutically acceptable salts thereof, along with adjuvant compositions comprising the compounds, vaccine compositions comprising the compounds, methods for inducing an enhanced immune response in a subject using the compounds and compositions, and methods for inducing or enhancing immunogenicity of an antigen using the compounds and compositions.

Other aspects and embodiments of the disclosure will become apparent in light of the following description and drawings.

DETAILED DESCRIPTION

Figure 1A:
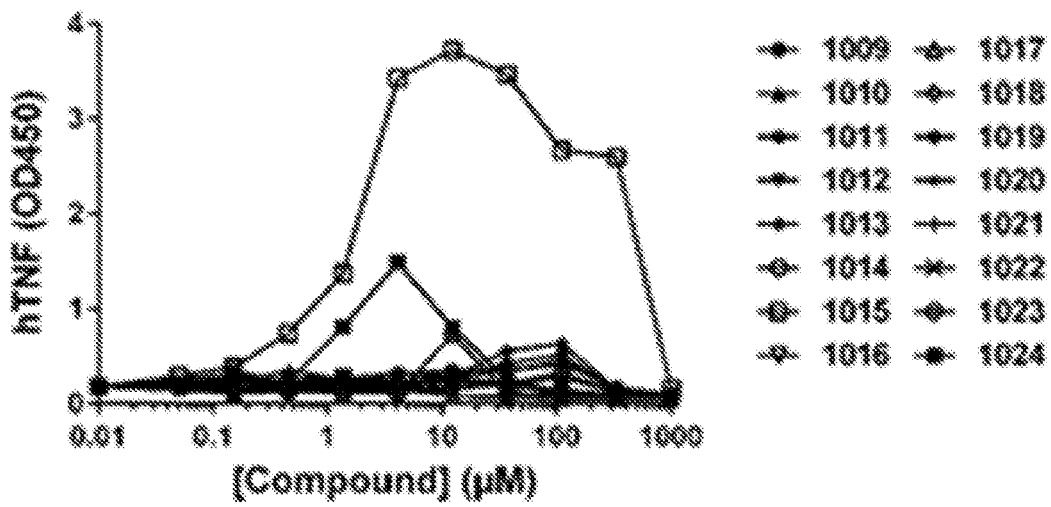
FIG. 1 shows the cytokine response from fresh peripheral blood mononuclear cells (PBMCs) cultured in the presence of a selection of DAT compounds at varying concentrations. The DAT compounds were delivered by drying to the bottom of the tissue culture plate after dissolving in IPA or by diluting in media after dissolving in DMSO. TNFα (FIG. 1A) and IL-6 (FIG. 1B) were measured after 18-24 hours after treatment.
Figure 1A:
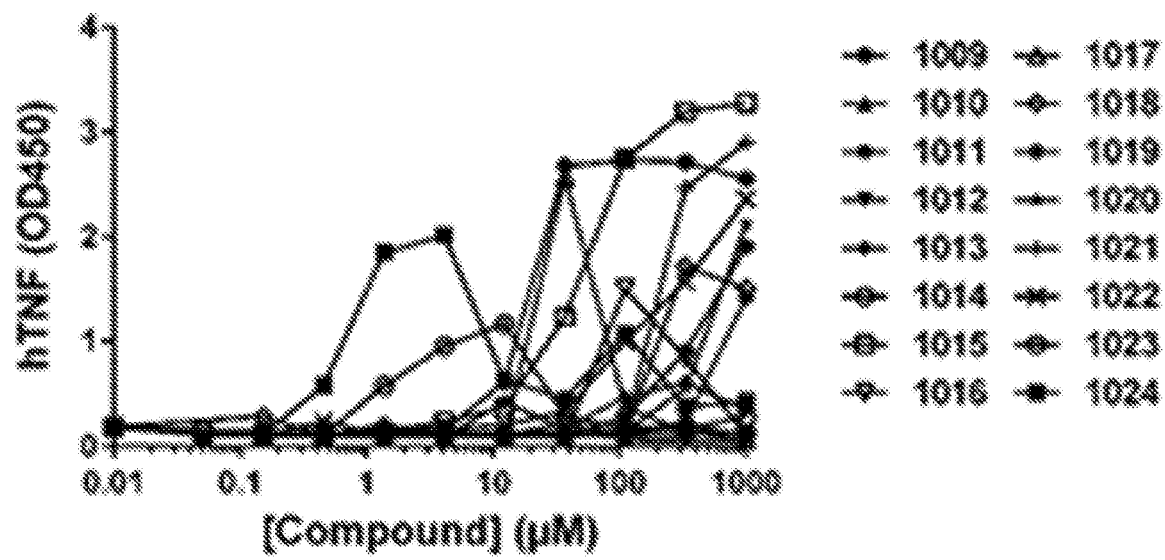

Described herein is a class of compounds that may act as Th17-inducing adjuvants, which may be useful for targeting diseases of significant medical burden for which no effective vaccine is available. The compounds may also be useful in the treatment of cancer.

The C-Type Lectin Receptor (CLR) family contains many diverse members that have different substrates, adaptor proteins, downstream signaling pathways, and cell type expression profiles. While some members of this family are purely phagocytic receptors, most are known to activate intracellular signaling networks that induce functional changes within the cell, such as modulation of transcription, endocytosis/phagocytosis, and/or cell adhesion and migration. One of the best characterized of these signaling cascade-inducing receptors is Mincle (CLEC4e).

Mincle must be coupled to an ITAM-containing adaptor molecule, FcRγ, to initiate downstream signaling, and ligand binding is $Ca^{2+}$-dependent. However, the ligands for the Mincle receptor are distinct from those for other CLR receptors such as Dectin-1 and Dectin-2, and include the mycobacterial glycolipid trehalose-6,6'-dimycolate (TDM), its synthetic analog trehalose dibehenate (TDB), and many α-mannose-containing lipids found in various fungi and Candida strains. These ligands can also be found in many pathogenic organisms including M. tuberculosis, S. mansoni, and T. rubrum. Additionally, the use of TDB and subsequent Mincle-induced signaling was shown to be necessary for the Th1/Th17 adjuvanting properties in some pre-clinical vaccine models.

Using an approach described herein for the identification of novel Th17-inducing CLR agonists as vaccine adjuvants, which can query single CLRs on the surface of myeloid cells using specifically designed molecules and follow their effects through signaling pathways and subsequent cytokine/biomarker induction downstream, new biologically active compounds have been identified that may serve as a basis for a new class of Th-17-inducing adjuvants. Furthermore, mechanism of action (MOA) studies with lead CLR agonists/antagonists in combination with Toll-Like Receptor (TLR) agonists can used to evaluate cross-talk between CLRs and TLRs through the evaluation of (1) intracellular signaling pathways, (2) biomarker upregulation, and (3) in vivo cytokine/biomarker induction.

Compounds described herein may represent a new class of Th17-inducing adjuvants for vaccines targeting bacterial and fungal pathogens causing a significant burden of disease in humans, certain cancers, and autoimmune diseases.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The term "immune response" includes any response associated with immunity including, but not limited to, increases or decreases in cytokine expression, production or secretion (e.g., IL-1, L-6, IL-17, TNFα expression, production or secretion), cytotoxicity, immune cell migration, antibody production and/or immune cellular responses.

The term "monotherapy," as used herein, means that only a single drug or therapeutic agent is administered.

The phrase "modulating an immune response" or "modulation of an immune response" or "modulate an immune response" includes upregulation, potentiating, stimulating, enhancing or increasing an immune response, as defined herein.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl," as used herein, means a straight or branched, saturated hydrocarbon chain containing from 1 to 10 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, 4,4-dimethylpentan-2-yl, n-heptyl, n-octyl, n-nonyl, and n-decyl.

The term "alkenyl," as used herein, means a straight or branched, hydrocarbon chain containing at least one carbon-carbon double bond and from 1 to 10 carbon atoms.

The term "alkoxyalkyl," as used herein, refers to an alkoxy group, as defined herein, appended to the parent molecular moiety through an alkyl group, as defined herein.

The term "alkoxyfluoroalkyl," as used herein, refers to an alkoxy group, as defined herein, appended to the parent molecular moiety through a fluoroalkyl group, as defined herein.

The term "alkylene," as used herein, refers to a divalent group derived from a straight or branched chain hydrocarbon of 1 to 10 carbon atoms, for example, of 2 to 5 carbon atoms. Representative examples of alkylene include, but are not limited to, —$CH_2CH_2$—, —$CH_2CH_2CH_2$—, —$CH_2CH(CH_3)CH_2$—, —$CH_2CH_2CH_2CH_2$—, —$CH_2CH(CH_3)CH_2CH_2$—, and —$CH_2CH_2CH_2CH_2CH_2$—.

The term "alkylamino," as used herein, means at least one alkyl group, as defined herein, is appended to the parent molecular moiety through an amino group, as defined herein.

The term "alkylsulfonyl," as used herein, means at least one alkyl group, as defined herein, is appended to the parent molecular moiety through an sulfonyl group, as defined herein.

The term "amide," as used herein, means —C(O)NR— or —NRC(O)—, wherein R may be hydrogen, alkyl, cycloalkyl, aryl, heteroaryl, heterocycle, alkenyl, or heteroalkyl.

The term "aminoalkyl," as used herein, means at least one amino group, as defined herein, is appended to the parent molecular moiety through an alkylene group, as defined herein.

The term "amino," as used herein, means —$NR_xR_y$, wherein $R_x$ and $R_y$ may be hydrogen, alkyl, cycloalkyl, aryl, heteroaryl, heterocycle, alkenyl, or heteroalkyl. In the case of an aminoalkyl group or any other moiety where amino appends together two other moieties, amino may be —$NR_x$—, wherein RX may be hydrogen, alkyl, cycloalkyl, aryl, heteroaryl, heterocycle, alkenyl, or heteroalkyl.

The term "aryl," as used herein, refers to a phenyl group, or a bicyclic or tricyclic fused ring system. Bicyclic fused ring systems are exemplified by a phenyl group appended to the parent molecular moiety and fused to a phenyl group, a cycloalkyl group as defined herein, a heteroaryl group as defined herein, or a heterocycle as defined herein. Tricyclic fused ring systems are exemplified by a phenyl group appended to the parent molecular moiety and fused to a bicyclic fused ring system as described herein. Representative examples of aryl include, but are not limited to, phenyl, naphthyl, anthracenyl, indolyl (e.g., 1H-indol-4-yl, 1H-indol-5-yl, 1H-indol-6-yl, and 1H-indol-7-yl), benzodioxolyl (e.g., benzo[d][1,3]dioxol-4-yl and benzo[d][1,3]dioxol-5-yl), chromanyl (e.g., chroman-5-yl, chroman-6-yl, chroman-7-yl, and chroman-8-yl), and tetrahydroquinolinyl (e.g., 1,2,3,4-tetrahydroquinolin-5-yl, 1,2,3,4-tetrahydroquinolin-6-yl, 1,2,3,4-tetrahydroquinolin-7-yl, and 1,2,3,4-tetrahydroquinolin-8-yl).

The term "arylamino," as used herein, means at least one aryl group, as defined herein, is appended to the parent molecular moiety through an amino group, as defined herein.

The term "cyanoalkyl," as used herein, means at least one —CN group, is appended to the parent molecular moiety through an alkylene group, as defined herein.

The term "cyanofluoroalkyl," as used herein, means at least one —CN group, is appended to the parent molecular moiety through a fluoroalkyl group, as defined herein.

The term "cycloalkoxy," as used herein, refers to a cycloalkyl group, as defined herein, appended to the parent molecular moiety through an oxygen atom.

The term "cycloalkyl," as used herein, refers to a carbocyclic ring system containing three to ten carbon atoms, zero heteroatoms and zero double bonds. The cycloalkyl may be monocyclic, bicyclic, bridged, fused, or spirocyclic. Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, and bicyclo[1.1.1]pentanyl. "Cycloalkyl" also includes carbocyclic ring systems in which a cycloalkyl group is appended to the parent molecular moiety and is fused to an aryl group as defined herein (e.g., a phenyl group), a heteroaryl group as defined herein, or a heterocycle as defined herein. Representative examples of such cycloalkyl groups include, but are not limited to, 2,3-dihydro-1H-indenyl (e.g., 2,3-dihydro-1H-inden-1-yl and 2,3-dihydro-1H-inden-2-yl), 6,7-dihydro-5H-cyclopenta[b]pyridinyl (e.g., 6,7-dihydro-5H-cyclopenta[b]pyridin-6-yl), oxaspiro[3.3]heptanyl (e.g., 2-oxaspiro[3.3]heptan-6-yl), and 5,6,7,8-tetrahydroquinolinyl (e.g., 5,6,7,8-tetrahydroquinolin-5-yl).

The term "cycloalkenyl," as used herein, means a non-aromatic monocyclic or multicyclic ring system containing at least one carbon-carbon double bond and preferably having from 5-10 carbon atoms per ring. The cycloalkenyl may be monocyclic, bicyclic, bridged, fused, or spirocyclic. Exemplary monocyclic cycloalkenyl rings include cyclopentenyl, cyclohexenyl, cycloheptenyl, and bicyclo[2.2.1]heptenyl.

The term "fluoroalkyl," as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "fluoroalkoxy," as used herein, means at least one fluoroalkyl group, as defined herein, is appended to the parent molecular moiety through an oxygen atom. Representative examples of fluoroalkoxy include, but are not limited to, difluoromethoxy, trifluoromethoxy and 2,2,2-trifluoroethoxy.

The term "halogen" or "halo," as used herein, means Cl, Br, I, or F.

The term "haloalkyl," as used herein, means an alkyl group, as defined herein, in which one, two, three, four, five, six, seven or eight hydrogen atoms are replaced by a halogen.

The term "haloalkoxy," as used herein, means at least one haloalkyl group, as defined herein, is appended to the parent molecular moiety through an oxygen atom.

The term "halocycloalkyl," as used herein, means a cycloalkyl group, as defined herein, in which one or more hydrogen atoms are replaced by a halogen.

The term "heteroalkyl," as used herein, means an alkyl group, as defined herein, in which one or more of the carbon atoms has been replaced by a heteroatom selected from S, O, P and N. Representative examples of heteroalkyls include, but are not limited to, alkyl ethers, secondary and tertiary alkyl amines, amides, and alkyl sulfides.

The term "heteroaryl," as used herein, refers to an aromatic monocyclic ring or an aromatic bicyclic ring system. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, indolyl, pyridinyl (including pyridin-2-yl, pyridin-3-yl, pyridin-4-yl), pyrimidinyl, pyrazinyl, pyridazinyl, pyrazolyl, pyrrolyl, benzopyrazolyl, 1,2,3-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, benzimidazolyl, benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl, quinazolinyl, 1,2,4-triazinyl, 1,3,5-triazinyl, isoquinolinyl, quinolinyl, 6,7-dihydro-1,3-benzothiazolyl, imidazo[1,2-a]pyridinyl, naphthyridinyl, pyridoimidazolyl, thiazolo[5,4-b]pyridin-2-yl, thiazolo[5,4-d]pyrimidin-2-yl.

The term "heterocycle" or "heterocyclic," as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, 2-oxo-3-piperidinyl, 2-oxoazepan-3-yl, oxadiazolinyl, oxadiazolidinyl, oxazolinyl, oxazolidinyl, oxetanyl, oxepanyl, oxocanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, 2-oxa-6-azaspiro[3.3]heptan-6-yl, azabicyclo[2.2.1]heptyl (including 2-azabicyclo[2.2.1]hept-2-yl), oxabicyclo[2.2.1]heptanyl (including 7-oxabicyclo[2.2.1]heptan-3-yl), azabicyclo[3.1.0]hexanyl (including 3-azabicyclo[3.1.0]hexan-3-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1 3,7]decane), and oxa-adamantane (2-oxatricyclo[3.3.1.1 3,7]decane). The monocyclic, bicyclic, and tricyclic heterocycles are connected to the parent molecular moiety through any carbon atom or any nitrogen atom contained within the rings, and can be unsubstituted or substituted.

The term "hydroxyl" or "hydroxy," as used herein, means an —OH group.

The term "hydroxyalkyl," as used herein, means at least one —OH group, is appended to the parent molecular moiety through an alkylene group, as defined herein.

The term "hydroxyfluoroalkyl," as used herein, means at least one —OH group, is appended to the parent molecular moiety through a fluoroalkyl group, as defined herein.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

The term "sulfonamide," as used herein, means —S(O)$_2$NR$^d$— or —NR$^d$S(O)—, wherein R$^d$ may be hydrogen, alkyl, cycloalkyl, aryl, heteroaryl, heterocycle, alkenyl, or heteroalkyl.

The term "sulfonyl" refers to the —S(O)2R' group wherein R' is alkoxy, alkyl, aryl, carbocyclic, heterocarbocyclic; heteroaryl, $C_1$-$C_4$ alkyl aryl or $C_1$-$C_4$ alkyl heteroaryl.

The term "substituents" refers to a group "substituted" on an aryl, heteroaryl, phenyl or pyridinyl group at any atom of that group. Any atom can be substituted.

The term "substituted" refers to a group that may be further substituted with one or more non-hydrogen substituent groups. Substituent groups include, but are not limited to, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl. For example, if a group is described as being "optionally substituted" (such as an alkyl, alkenyl, alkynyl, aryl, heteroaryl, cycloalkyl, heteroalkyl, heterocycle or other group such as an R group), it may have 0, 1, 2, 3, 4 or 5 substituents independently selected from halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

The term "═══" designates a single bond (—) or a double bond (═).

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

When substituent groups are specified by their conventional chemical formulae, written from left to right, such a formula also encompasses the same substituent that would result from writing the structure from right to left. For example, —CH$_2$NH— is also intended to encompass —NHCH$_2$—.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. COMPOUNDS

In one aspect, disclosed is a compound of formula (I):

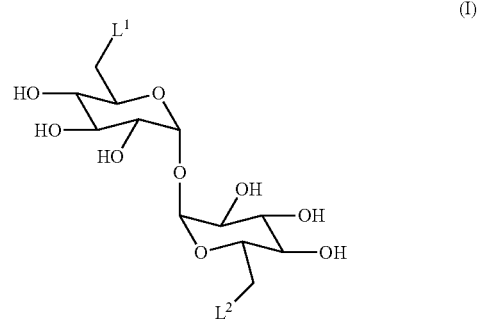

(I)

or a pharmaceutically acceptable salt thereof, wherein
L$^1$ is —OH or —X(CR$^{1a}$R$^{1a'}$)$_m$O$_p$Ar$^1$;
L$^2$ is —Y(CR$^{2a}$R$^{2a'}$)$_n$O$_q$Ar$^2$;
X and Y are each independently selected from —OC(O)—, —NR$^a$C(O)—, —NR$^b$C(S)—, —NR$^c$—, —SO$_2$NR$^c$—, —O—, and —OC(O)CH═CH—;

$R^a$, $R^b$, and $R^c$ are each independently selected from hydrogen and $C_1$-$C_4$alkyl;

m is 0, 1 or 2;

n is 0, 1 or 2;

$R^{1a}$, $R^{1a'}$, $R^{2a}$ and $R^{2a'}$, when present, are each independently selected from hydrogen and $C_1$-$C_4$ alkyl;

p is 0 or 1;

q is 0 or 1;

$Ar^1$ and $Ar^2$ are each independently selected from aryl or heteroaryl, wherein each aryl or heteroaryl may be independently substituted or unsubstituted with 1, 2, 3, 4, or 5 substituents independently selected from hydrogen, $C_1$-$C_{12}$alkyl, hydroxy, $C_1$-$C_{12}$alkoxy, halo, $C_1$-$C_4$haloalkyl, $Ar^3$, $C_1$-$C_8$alkoxy-$C_1$-$C_8$alkoxy, $C_1$-$C_8$alkoxy-$C_1$-$C_8$alkyl, hydroxy-$C_1$-$C_8$alkyl, amino, nitro, —NH—$Ar^4$, $C_1$-$C_8$alkoxy-$Ar^5$, $C_1$-$C_8$alkylsulfonyl, and $C_1$-$C_8$alkoxy-$C_1$-$C_8$alkoxy-$C_1$-$C_8$alkoxy, or the substituents, together with the atoms to which they are attached, are optionally taken together to form an aryl ring; wherein each heteroaryl may include 1, 2, 3, 4, or 5 heteroatoms selected from O, S or N;

$Ar^3$, $Ar^4$ and $Ar^5$ are each independently selected from aryl or heteroaryl independently unsubstituted or substituted with 1, 2, 3, or 4 substituents independently selected from $C_1$-$C_4$alkyl, hydroxy, $C_1$-$C_4$alkoxy, halo, $C_1$-$C_4$haloalkyl, and $C_1$-$C_4$hydroxyalkyl; and wherein the compound is not:

6,6'-bis(2-methoxybenzoyl)-α,α-D-trehalose,
6,6'-bis(benzoylamino)-α,α-D-trehalose,
6,6'-bis(2-hydroxybenzoyl)-α,α-D-trehalose,
6,6'-bis(2-hydroxybenzoylamino)-α,α-D-trehalose,
6,6'-bis(2-methylbenzoyl)-α,α-D-trehalose,
6,6'-bis(2-methylbenzoylamino)-α,α-D-trehalose,
6,6'-bis(4-methoxybenzoyl)-α,α-D-trehalose,
6,6'-bis(4-methoxybenzoylamino)-α,α-D-trehalose,
6,6'-bis(4-hydroxybenzoyl)-α,α-D-trehalose,
6,6'-bis(4-hydroxybenzoylamino)-α,α-D-trehalose,
6,6'-bis(4-benzyloxybenzoyl)-α,α-D-trehalose,
6,6'-bis(2,3-dimethoxybenzoyl)-α,α-D-trehalose,
6,6'-bis(2,3-dimethoxybenzoylamino)-α,α-D-trehalose,
6,6'-bis(2,6-difluorobenzoyl)-α,α-D-trehalose,
6,6'-bis(2,6-difluorobenzoylamino)-α,α-D-trehalose,
6,6'-bis(2,6-dichlorobenzoyl)-α,α-D-trehalose,
6,6'-bis(2,3-dihydroxybenzoyl)-α,α-D-trehalose,
6,6'-bis(2,4-dihydroxybenzoyl)-α,α-D-trehalose,
6,6'-bis(2,4-dihydroxybenzoylamino)-α,α-D-trehalose,
6,6'-bis(2,3-dibenzyloxybenzoyl)-α,α-D-trehalose,
6,6'-bis(2-hydroxy-3-methoxybenzoyl)-α,α-D-trehalose,
6,6'-bis(2-benzyloxy-3-methoxybenzoyl)-α,α-D-trehalose,
6,6'-bis(2-methyl-6-aminobenzoyl)-α,α-D-trehalose,
6,6'-bis(3-methoxy-4-fluorobenzoyl)-α,α-D-trehalose,
6,6'-bis(3,4,5-trimethoxybenzoyl)-α,α-D-trehalose,
6,6'-bis(3,4,5-trimethoxybenzoylamino)-α,α-D-trehalose,
6,6'-bis(2,4-dihydroxy-6-methylbenzoyl)-α,α-D-trehalose,
6,6'-bis(2,4-dimethoxy-6-methylbenzoyl)-α,α-D-trehalose,
6,6'-bis(2-hydroxy-4-n-heptyloxybenzoyl)-α,α-D-trehalose,
6,6'-bis(2-hydroxy-4-n-pentyloxybenzoyl)-α,α-D-trehalose,
6,6'-bis(2-hydroxy-4-methoxybenzoyl)-α,α-D-trehalose,
6,6'-bis(4-n-pentyloxybenzoyl)-α,α-D-trehalose,
6,6'-bis(2,4-dihydroxy-6-methylbenzoyl)-α,α-D-trehalose,
6,6'-bis(cinnamoylamino)-α,α-D-trehalose,
6,6'-bis(3,4-dimethoxycinnamoylamino)-α,α-D-trehalose,
6,6'-bis(isonicotinoylamino)-α,α-D-trehalose, or
6,6'-bis(pyrazine-2-carbonylamino)-α,α-D-trehalose.

In some embodiments, p and q are 0.

In some embodiments, $L^1$ is

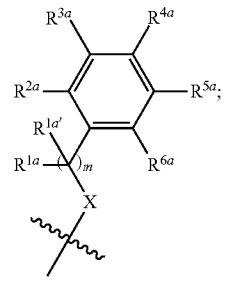

m is 0, 1 or 2;

$R^{1a}$ and $R^{1a'}$, when present, are each independently selected from hydrogen and $C_1$-$C_4$ alkyl; and $R^{2a}$, $R^{3a}$, $R^{4a}$, $R^{5a}$, and $R^{6a}$ are each independently selected from hydrogen, $C_1$-$C_{12}$alkyl, hydroxy, $C_1$-$C_{12}$alkoxy, halo, $C_1$-$C_4$haloalkyl, aryl, $C_1$-$C_8$alkoxy-$C_1$-$C_8$alkoxy, $C_1$-$C_8$alkoxy-$C_1$-$C_8$alkyl, hydroxy-$C_1$-$C_8$alkyl, amino, nitro, arylamino, $C_1$-$C_8$alkoxy-aryl, $C_1$-$C_8$alkylsulfonyl, and $C_1$-$C_8$alkoxy-$C_1$-$C_8$alkoxy-$C_1$-$C_8$alkoxy, or together with the atoms to which they are attached, are optionally taken together to form an aryl ring.

In some embodiments, $R^{1a'}$, when present, is hydrogen.

In some embodiments, $R^{2a}$, $R^{3a}$, $R^{4a}$, $R^{5a}$, and $R^{6a}$ are each independently selected from hydrogen, $C_1$-$C_{12}$alkyl, hydroxy, $C_1$-$C_{12}$alkoxy, halo, $C_1$-$C_4$haloalkyl, aryl, $C_1$-$C_8$alkoxy-$C_1$-$C_8$alkoxy, $C_1$-$C_8$alkoxy-$C_1$-$C_8$alkyl, hydroxy-$C_1$-$C_8$alkyl, amino, nitro, arylamino, $C_1$-$C_8$alkoxy-aryl, $C_1$-$C_8$alkylsulfonyl, and $C_1$-$C_8$alkoxy-$C_1$-$C_8$alkoxy-$C_1$-$C_8$alkoxy, or together with the atoms to which they are attached, are optionally taken together to form an aryl ring.

In some embodiments, $L^2$ is

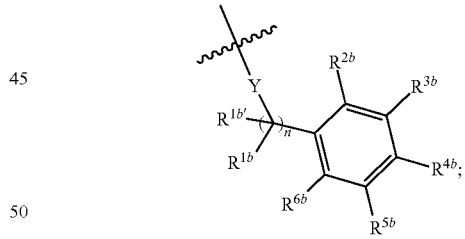

n is 0, 1 or 2;

$R^{1b}$ and $R^{1b'}$, when present, are each independently selected from hydrogen and $C_1$-$C_4$ alkyl; and $R^{2b}$, $R^{3b}$, $R^{4b}$, $R^{5b}$, and $R^{6b}$ are each independently selected from hydrogen, $C_1$-$C_{12}$alkyl, hydroxy, $C_1$-$C_{12}$alkoxy, halo, $C_1$-$C_4$haloalkyl, aryl, $C_1$-$C_8$alkoxy-$C_1$-$C_8$alkoxy, $C_1$-$C_8$alkoxy-$C_1$-$C_8$alkyl, hydroxy-$C_1$-$C_8$alkyl, amino, nitro, arylamino, $C_1$-$C_8$alkoxy-aryl, $C_1$-$C_8$alkylsulfonyl, and $C_1$-$C_8$alkoxy-$C_1$-$C_8$alkoxy-$C_1$-$C_8$alkoxy, or together with the atoms to which they are attached, are optionally taken together to form an aryl ring.

In some embodiments, $R^{1b'}$, when present, is hydrogen.

In some embodiments, $R^{2b}$, $R^{3b}$, $R^{4b}$, $R^{5b}$, and $R^{6b}$ are each independently selected from hydrogen, $C_1$-$C_8$alkyl, hydroxy, $C_1$-$C_8$alkoxy, halo, $C_1$-$C_4$haloalkyl, aryl, $C_1-C_8$alkoxy-$C_1-C_8$alkoxy, $C_1-C_8$alkoxy-$C_1-C_8$alkyl, and hydroxy-$C_1-C_8$alkyl. In some embodiments, $R^{3b}$ and $R^{4b}$, together with the carbon atoms to which they are attached, are optionally taken together to form an aryl ring.

In another aspect, disclosed is a compound of formula (Ia):

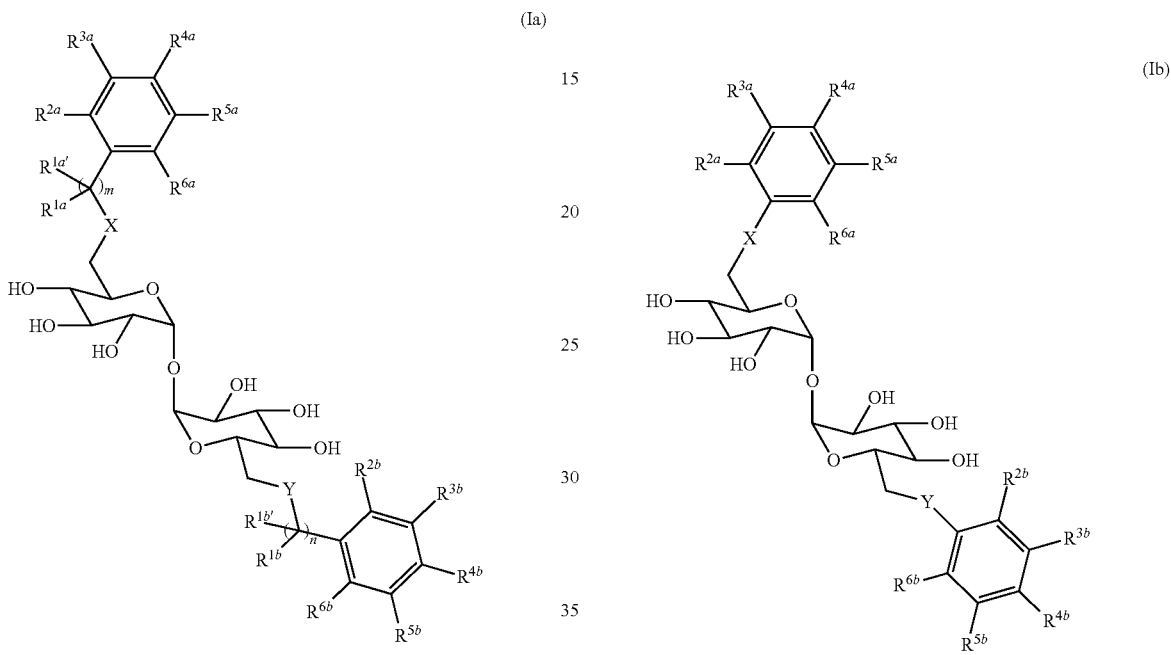

or a pharmaceutically acceptable salt thereof, wherein

X and Y are each independently selected from —OC(O)— and —NR$^a$C(O)—;

R$^a$ is independently selected from hydrogen and $C_1-C_4$ alkyl;

m is 0, 1 or 2;

n is 0, 1 or 2;

$R^{1a}$, $R^{1a'}$, $R^{1b}$ and $R^{1b'}$ when present, are each hydrogen; and $R^{2a}$, $R^{2b}$, $R^{3a}$, $R^{3b}$, $R^{4a}$, $R^{4b}$, $R^{5a}$, $R^{5b}$, $R^{6a}$, and $R^{6b}$ are each independently selected from hydrogen, $C_1-C_8$alkyl, and hydroxy.

In some embodiments, at least one of $R^{2a}$, $R^{3a}$, $R^{4a}$, $R^{5a}$, and $R^{6a}$ is $C_1-C_8$alkyl and at least one of $R^{2b}$, $R^{3b}$, $R^{4b}$, $R^{5b}$, and $R^{6b}$ is $C_1-C_8$alkyl. In some embodiments, each of $R^{3a}$, $R^{3b}$, $R^{5a}$, and $R^{5b}$ are $C_1-C_8$alkyl. In some embodiments, the $C_1-C_8$alkyl is isopropyl, tert-butyl, methyl or ethyl. In exemplary embodiments, the $C_1-C_8$alkyl is tert-butyl.

In some embodiments, $R^{2a}$, $R^{2b}$, $R^{4a}$, $R^{4b}$, $R^{6a}$, $R^{6b}$ are each independently hydroxy or hydrogen. In some embodiments, $R^{2a}$ and $R^{2b}$ are each hydroxy. In some embodiments, $R^{4a}$ and $R^{4b}$ are each hydroxy.

In some embodiments, $R^{2a}$, $R^{2b}$, $R^{6a}$, and $R^{6b}$ are methyl. In some embodiments, $R^{3a}$, $R^{3b}$, $R^{4a}$, $R^{4b}$, $R^{5a}$, and $R^{5b}$ are each independently hydrogen or $C_1-C_8$alkyl. In some embodiments, the $C_1-C_8$ alkyl is methyl or tert-butyl.

In some embodiments, m and n are 0.

In another aspect, disclosed is a compound of formula (Ib):

or a pharmaceutically acceptable salt thereof, wherein

X and Y are each independently selected from —OC(O)— and —NR$^a$C(O)—;

R$^a$ is independently selected from hydrogen and $C_1-C_4$alkyl;

$R^{2a}$, $R^{2b}$, $R^{3a}$, $R^{3b}$, $R^{4a}$, $R^{4b}$, $R^{5a}$, $R^{5b}$, $R^{6a}$, and $R^{6b}$ are each independently selected from hydrogen, $C_1-C_{12}$alkyl, hydroxy, $C_1-C_{12}$alkoxy, $C_1-C_4$haloalkyl, Ar$^3$ and, —NH—Ar$^4$ or together with the atoms to which they are attached, are optionally taken together to form an aryl ring;

Ar$^3$, Ar$^4$ and Ar$^5$ are each independently selected from aryl or heteroaryl independently unsubstituted or substituted with 1, 2, 3, or 4 substituents independently selected from $C_1-C_4$ alkyl, hydroxy, $C_1-C_4$alkoxy, halo, $C_1-C_4$haloalkyl, and $C_1-C_4$hydroxyalkyl.

In some embodiments, $R^{3a}$, $R^{3b}$, $R^{5a}$, and $R^{5b}$ are each $C_1-C_8$alkoxy. In some embodiments, wherein $R^{2a}$, $R^{2b}$, $R^{4a}$, $R^{4b}$, $R^{6a}$, and $R^{6b}$ are each hydrogen. In some embodiments, $R^{4a}$ and $R^{4b}$, are each $C_1-C_5$alkoxy. In some embodiments, $R^{3a}$, $R^{3b}$, $R^{4a}$, $R^{4b}$, $R^{5a}$, and $R^{5b}$ are each ethoxy. In some embodiments, $R^{2a}$, $R^{2b}$, $R^{6a}$ and $R^{6b}$ are each hydrogen.

In some embodiments, $R^{2a}$ and $R^{2b}$ are each $C_1-C_8$alkoxy or hydroxy. In some embodiments, at least one of $R^{3a}$, $R^{4a}$, $R^{5a}$, and $R^{6a}$ is $C_1-C_8$alkyl and at least one of $R^{3b}$, $R^{4b}$, $R^{5b}$, and $R^{6b}$ is $C_1-C_8$alkyl. In some embodiments, the $C_1-C_8$alkyl is tert-butyl.

In some embodiments, at least one of $R^{2a}$, $R^{3a}$, $R^{4a}$, $R^{5a}$, and $R^{6a}$ is $C_1$-$C_4$haloalkyl and at least one of $R^{2b}$, $R^{3b}$, $R^{4b}$, $R^{5b}$, and $R^{6b}$ is $C_1$-$C_4$haloalkyl. In some embodiments, $R^{2a}$ and $R^{2b}$ are each $C_1$-$C_4$haloalkyl. In some embodiments, $R^{3a}$, $R^{3b}$, $R^{5a}$, and $R^{5b}$ are each hydrogen. In some embodiments, $R^{6a}$ and $R^{6b}$ are each hydrogen or $C_1$-$C_4$haloalkyl. In some embodiments, $R^{4a}$ and $R^{4b}$ are each hydrogen or $C_1$-$C_4$alkoxy. In some embodiments, the $C_1$-$C_4$alkoxy is methoxy.

In some embodiments, $R^{3a}$ and $R^{3b}$ are each $C_1$-$C_4$haloalkyl. In some embodiments, $R^{5a}$ and $R^{5b}$ are each hydrogen or $C_1$-$C_4$haloalkyl. In some embodiments, $R^{2a}$ and $R^{2b}$ are each hydrogen or hydroxy. In some embodiments, $R^{4a}$, $R^{4b}$, $R^{6a}$, and $R^{6b}$ are each hydrogen.

In some embodiments, $R^{5a}$, and $R^{5b}$ are each $C_1$-$C_4$alkoxy. In some embodiments, the $C_1$-$C_4$alkoxy is methoxy. In some embodiments, $R^{3a}$, $R^{3b}$, $R^{4a}$, $R^{4b}$, $R^{6a}$, and $R^{6b}$ are hydrogen.

In some embodiments, the $C_1$-$C_4$haloalkyl is trifluoromethyl.

In some embodiments, $R^{6a}$ and $R^{6b}$ are each hydrogen, $R^{2a}$, $R^{2b}$, $R^{3a}$, $R^{3b}$, $R^{4a}$, $R^{4b}$, $R^{5a}$, and $R^{5b}$ are each independently selected from hydrogen, hydroxy, $Ar^3$ and, —NH—$Ar^4$, wherein at least one of $R^{2a}$, $R^{3a}$, $R^{4a}$, and $R^{5a}$ is $Ar^3$ or —NH—$Ar^4$ and at least one of $R^{2b}$, $R^{3b}$, $R^{4b}$, and $R^{5b}$ is $Ar^3$ or —NH—$Ar^4$; and $Ar^3$ and $Ar^4$ are each independently selected from aryl or heteroaryl independently unsubstituted or substituted with 1, 2, 3, or 4 substituents independently selected from $C_1$-$C_4$ alkyl, hydroxy, $C_1$-$C_4$alkoxy, halo, $C_1$-$C_4$haloalkyl, and $C_1$-$C_4$hydroxyalkyl.

In some embodiments, $Ar^3$ and $Ar^4$ are phenyl unsubstituted or substituted with 1, 2, or 3 substituents independently selected from the group consisting of hydroxy, alkoxy, $C_1$-$C_4$alkyl, and hydroxy-$C_1$-$C_4$alkyl. In some embodiments, the phenyl is substituted with one substituent selected from methyl, hydroxy, and hydroxymethyl. In some embodiments, at least one of $R^{2a}$, $R^{3a}$, $R^{4a}$, and $R^{5a}$ is hydroxy and at least one of $R^{2b}$, $R^{3b}$, $R^{4b}$, and $R^{5b}$ is hydroxy.

In some embodiments, at least two of $R^{3a}$, $R^{4a}$, and $R^{5a}$ are $C_5$-$C_{12}$alkoxy, at least two of $R^{3b}$, $R^{4b}$, and $R^{5b}$ are $C_5$-$C_{12}$alkoxy, and $R^{2a}$, $R^{2b}$, $R^{6a}$, and $R^{6b}$ are each hydrogen. In some embodiments, $R^{3a}$, $R^{3b}$, $R^{5a}$, and $R^{5b}$ are each $C_5$-$C_{12}$alkoxy. In some embodiments, $R^{4a}$ and $R^{4b}$ are each $C_5$-$C_{12}$alkoxy.

A compound selected from the group consisting of: 6,6'-bis(3,5-dimethoxybenzoyl)-α,α-D-trehalose, 6,6'-bis(2-hydroxy-3,5-di-tert-butylbenzoyl)-α,α-D-trehalose, 6,6'-bis(3,5-dipentyloxybenzoyl)-α,α-D-trehalose, 6,6'-bis(3,4,5-triethoxybenzoyl)-α,α-D-trehalose, 6,6'-bis(2-hydroxy-3,5-di-tert-butylbenzoylamino)-α,α-D-trehalose, 6,6'-bis(2,6-hydroxy-3,5-di-tert-butylbenzoylamino)-α,α-D-trehalose, or a pharmaceutically acceptable salt thereof.

In some embodiments, the compound is 6,6-bis(3,5-dimethoxybenzoyl)-α,α-D-trehalose, or a pharmaceutically acceptable salt thereof.

In some embodiments, the compound is 6,6-bis(2-hydroxy-3,5-di-tert-butylbenzoyl)-α,α-D-trehalose, or a pharmaceutical acceptable salt thereof.

In another aspect, disclosed is a compound of formula (II):

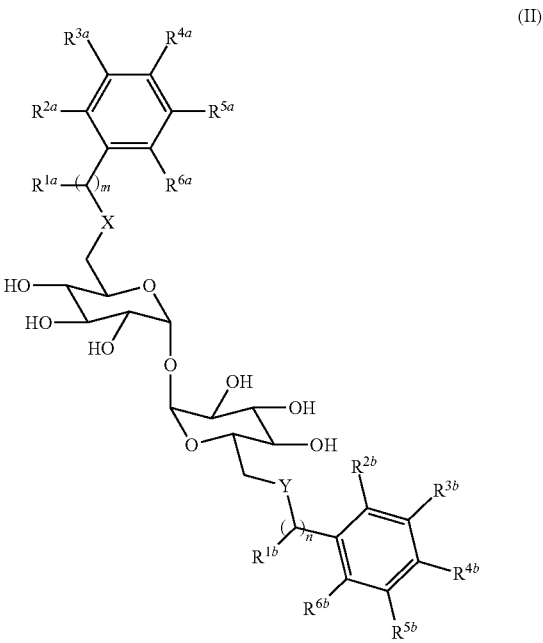

or a pharmaceutically acceptable salt thereof, wherein
m is 0, 1 or 2;
n is 0, 1 or 2;
X and Y are each independently selected from —C(O)O—, —C(O)NR$^a$—, —C(S)NR$^b$—, —NR$^c$—, and —O—;
R$^a$, R$^b$, and R$^c$ are each independently selected from hydrogen and $C_1$-$C_4$ alkyl;
$R^{1a}$ and $R^{1b}$, when present, are each independently selected from hydrogen and $C_1$-$C_4$ alkyl;
$R^{2a}$, $R^{2b}$, $R^{3a}$, $R^{3b}$, $R^{4a}$, $R^{4b}$, $R^{5a}$, $R^{5b}$, $R^{6a}$, and $R^{6b}$ are each independently selected from hydrogen, $C_1$-$C_8$-alkyl, hydroxy, $C_1$-$C_8$-alkoxy, halo, $C_1$-$C_4$ haloalkyl, aryl, $C_1$-$C_8$-alkoxy-$C_1$-$C_8$-alkoxy, $C_1$-$C_8$-alkoxy-$C_1$-$C_8$-alkyl, and hydroxy-$C_1$-$C_8$-alkyl;
wherein $R^{3a}$ and $R^{4a}$, together with the carbon atoms to which they are attached, are optionally taken together to form an aryl ring;
wherein $R^{3b}$ and $R^{4b}$, together with the carbon atoms to which they are attached, are optionally taken together to form an aryl ring;
wherein each aryl is independently unsubstituted or substituted with 1, 2, or 3 substituents independently selected from $C_1$-$C_4$-alkyl, hydroxy, $C_1$-$C_4$-alkoxy, halo, $C_1$-$C_4$ haloalkyl, and $C_1$-$C_4$ hydroxyalkyl; and
wherein the compound is not:
6,6'-bis(2-methoxybenzoyl)-α,α-D-trehalose,
6,6'-bis(2-hydroxybenzoyl)-α,α-D-trehalose,
6,6'-bis(2-methylbenzoyl)-α,α-D-trehalose,
6,6'-bis(4-methoxybenzoyl)-α,α-D-trehalose,
6,6'-bis(4-hydroxybenzoyl)-α,α-D-trehalose,
6,6'-bis(4-benzyloxybenzoyl)-α,α-D-trehalose,
6,6'-bis(2,3-dimethoxybenzoyl)-α,α-D-trehalose,
6,6'-bis(2,6-difluorobenzoyl)-α,α-D-trehalose,
6,6'-bis(2,6-dichlorobenzoyl)-α,α-D-trehalose,
6,6'-bis(2,3-dihydroxybenzoyl)-α,α-D-trehalose,
6,6'-bis(2,4-dihydroxybenzoyl)-α,α-D-trehalose,
6,6'-bis(2,3-dibenzyloxybenzoyl)-α,α-D-trehalose,
6,6'-bis(2-hydroxy-3-methoxybenzoyl)-α,α-D-trehalose,
6,6'-bis(2-benzyloxy-3-methoxybenzoyl)-α,α-D-trehalose,
6,6'-bis(2-methyl-6-aminobenzoyl)-α,α-D-trehalose, 6,6'-bis(3-methoxy-4-fluorobenzoyl)-α,α-D-trehalose,
6,6'-bis(3,4,5-trimethoxybenzoyl)-α,α-D-trehalose,
6,6'-bis(2,4-dihydroxy-6-methylbenzoyl)-α,α-D-trehalose,
6,6'-bis(2,4-dimethoxy-6-methylbenzoyl)-α,α-D-trehalose,
6,6'-bis(2-hydroxy-4-n-heptyloxybenzoyl)-α,α-D-trehalose,
6,6'-bis(2-hydroxy-4-n-pentyloxybenzoyl)-α,α-D-trehalose,
6,6'-bis(2-hydroxy-4-methoxybenzoyl)-α,α-D-trehalose,
6,6'-bis(4-n-pentyloxybenzoyl)-α,α-D-trehalose, or
6,6'-bis(2,4-dihydroxy-6-methylbenzoyl)-α,α-D-trehalose.

In some embodiments, $R^{3a}$, $R^{3b}$, $R^{5a}$, and $R^{5b}$ are each $C_2$-$C_8$ alkoxy. In some embodiments, $R^{3a}$, $R^{3b}$, $R^{5a}$, and $R^{5b}$ are each ethoxy.

In some embodiments, $R^{2a}$, $R^{2b}$, $R^{4a}$, $R^{4b}$, $R^{6a}$, and $R^{6b}$ are hydrogen. In some embodiments, at least one of $R^{2a}$, $R^{2b}$, $R^{3a}$, $R^{3b}$, $R^{4a}$, $R^{4b}$, $R^{5a}$, $R^{5b}$, and $R^{6a}$, and $R^{6b}$ is tert-butyl. In some embodiments, $R^{3a}$, $R^{3b}$, $R^{5a}$, and $R^{5b}$ are each tert-butyl. In some embodiments, $R^{2a}$ and $R^{2b}$ are each hydroxy. In some embodiments, $R^{4a}$, $R^{4b}$, $R^{6a}$, and $R^{6b}$ are each hydrogen.

In some embodiments, m is 0 and n is 0.
In some embodiments, X and Y are each —C(O)O—.
In another aspect, disclosed is a compound of formula (IIa):

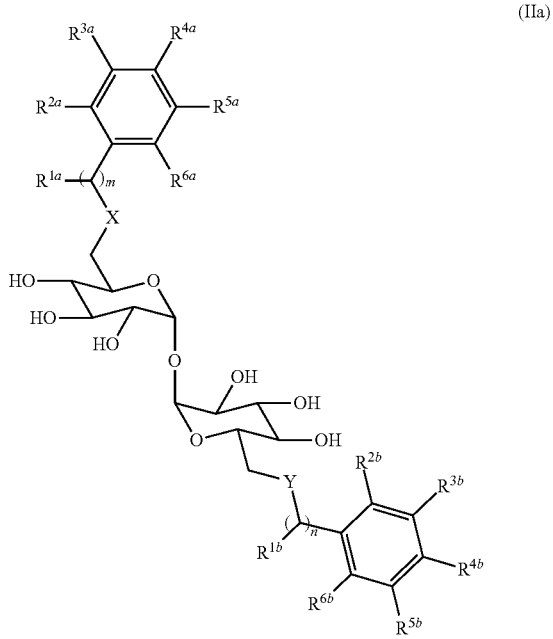

(IIa)

or a pharmaceutically acceptable salt thereof, wherein:
m is 0 or 1;
n is 0 or 1;
X and Y are each independently selected from —C(O)O—, —C(O)NR$^a$—, —C(S)NR$^b$—, —NR$^c$—, and —O—;
$R^a$, $R^b$, and $R^c$ are each independently selected from hydrogen and $C_1$-$C_4$alkyl;
$R^{1a}$ and $R^{1b}$, when present, are each independently selected from hydrogen and $C_1$-$C_4$alkyl;
$R^{2a}$, $R^{2b}$, $R^{6a}$, and $R^{6b}$ are each independently selected from hydrogen, $C_1$-$C_4$alkyl, hydroxy, and $C_1$-$C_4$alkoxy;
$R^{4a}$ and $R^{4b}$ are hydrogen;
$R^{3a}$, $R^{3b}$, $R^{5a}$, and $R^{5b}$ are each independently selected from $C_1$-$C_8$alkyl, hydroxy, $C_1$-$C_8$alkoxy, halo, $C_1$-$C_8$haloalkyl, aryl, $C_1$-$C_8$alkoxy-$C_1$-$C_8$alkoxy, $C_1$-$C_8$alkoxy-$C_1$-$C_8$alkyl, hydroxy-$C_1$-$C_8$alkyl; and
wherein each aryl is independently unsubstituted or substituted with 1, 2, or 3 substituents independently selected from $C_1$-$C_4$alkyl, hydroxy, $C_1$-$C_4$alkoxy, halo, $C_1$-$C_4$haloalkyl, and $C_1$-$C_4$hydroxyalkyl.

In some embodiments: each n is 0; $R^{2a}$ and $R^{2b}$ are each independently hydrogen or hydroxy; $R^{3a}$ and $R^{3b}$ are each independently selected from $C_1$-$C_8$alkyl, hydroxy, $C_2$-$C_8$alkoxy, $C_1$-$C_4$alkoxy-$C_1$-$C_4$alkoxy, and $C_1$-$C_4$haloalkyl; $R^{5a}$ and $R^{5b}$ are each independently selected from $C_1$-$C_8$alkyl, hydroxy, $C_2$-$C_8$alkoxy, $C_1$-$C_4$alkoxy-$C_1$-$C_4$alkoxy, and $C_1$-$C_4$haloalkyl; and $R^{6a}$ and $R^{6b}$ are each independently hydrogen or hydroxy.

In some embodiments, $R^{3a}$, $R^{3b}$, $R^{5a}$, and $R^{5b}$ are each $C_2$-$C_8$ alkoxy. In some embodiments, $R^{3a}$, $R^{3b}$, $R^{5a}$, and $R^{5b}$ are each ethoxy.

In some embodiments, $R^{2a}$, $R^{2b}$, $R^{6a}$, and $R^{6b}$ are each hydrogen.

In some embodiments, at least one of $R^{3a}$, $R^{3b}$, $R^{5a}$, and $R^{5b}$ is tert-butyl. In some embodiments, $R^{3a}$, $R^{3b}$, $R^{5a}$, and $R^{5b}$ are each tert-butyl.

In some embodiments, $R^{2a}$ and $R^{2b}$ are each hydroxy.
In some embodiments, $R^{6a}$ and $R^{6b}$ are each hydrogen.
In some embodiments, m is 0 and n is 0.
In some embodiments, X and Y are each —C(O)O—.
In another aspect, disclosed is a compound of formula (IIb):

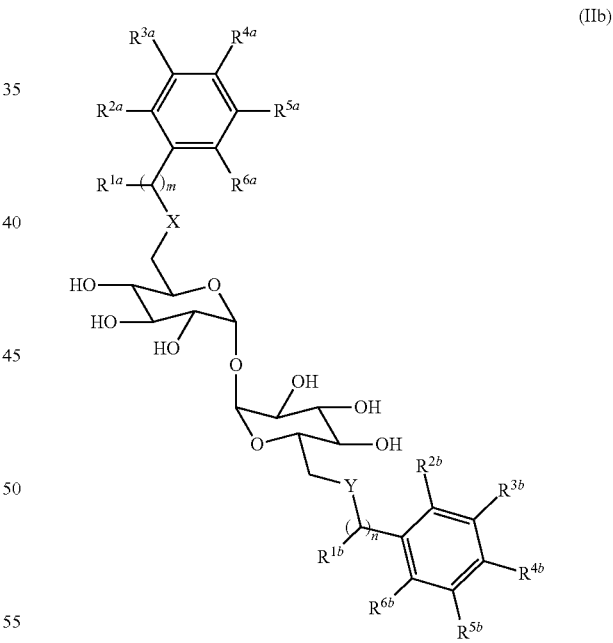

(IIb)

or a pharmaceutically acceptable salt thereof, wherein:
m is 0 or 1;
n is 0 or 1;
X and Y are each independently selected from —C(O)O—, —C(O)NR$^a$—, —C(S)NR$^b$—, —NR$^c$—, and —O—;
$R^a$, $R^b$, and $R^c$ are each independently selected from hydrogen and $C_1$-$C_4$ alkyl;
$R^{1a}$ and $R^{1b}$, when present, are each independently selected from hydrogen and $C_1$-$C_4$ alkyl;
$R^{6a}$ and $R^{6b}$ are each hydrogen; and $R^{2a}$, $R^{2b}$, $R^{3a}$, $R^{3b}$, $R^{4a}$, $R^{4b}$, $R^{5a}$, and $R^{5b}$ are each independently selected from hydrogen, hydroxy, and aryl, wherein at least one of $R^{2a}$, $R^{2b}$, $R^{3a}$, $R^{3b}$, $R^{4a}$, $R^{4b}$, $R^{5a}$, and $R^{5b}$ is aryl; or wherein $R^{3a}$ and $R^{4a}$, together with the carbon atoms to which they are attached, are optionally taken together to form an aryl ring; or wherein $R^{3b}$ and $R^{4b}$, together with the carbon atoms to which they are attached, are optionally taken together to form an aryl ring;

wherein each aryl is independently unsubstituted or substituted with 1, 2, or 3 substituents independently selected from $C_1$-$C_4$-alkyl, hydroxy, $C_1$-$C_4$-alkoxy, halo, $C_1$-$C_4$ haloalkyl, and $C_1$-$C_4$ hydroxyalkyl.

In some embodiments, m is 0 and n is 0.

In some embodiments, one of $R^{2a}$, $R^{2b}$, $R^{3a}$, $R^{3b}$, $R^{4a}$, $R^{4b}$, $R^{5a}$, and $R^{5b}$ is phenyl, and the phenyl is unsubstituted or substituted with 1, 2, or 3 substituents independently selected from the group consisting of hydroxy, alkoxy, $C_1$-$C_4$alkyl, and hydroxy-$C_1$-$C_4$alkyl. In some embodiments, the phenyl is substituted with one substituent selected from methyl, hydroxy, and hydroxymethyl.

In some embodiments, X and Y are each —C(O)O—.

In another aspect, disclosed is a compound of formula (IIc):

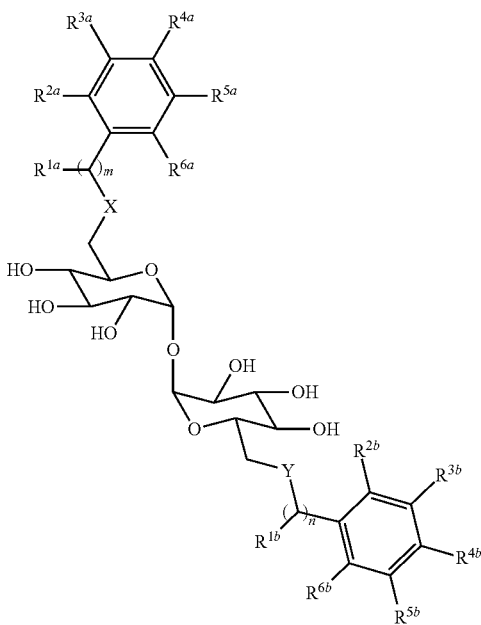

(IIc)

or a pharmaceutically acceptable salt thereof, wherein:
m is 0 or 1;
n is 0 or 1;
X and Y are each independently selected from —C(O)O—, —C(O)NR$^a$—, —C(S)NR$^b$—, —NR$^c$—, and —O—;
R$^a$, R$^b$, and R$^c$ are each independently selected from hydrogen and $C_1$-$C_4$ alkyl;
$R^{2a}$, $R^{2b}$, $R^{3a}$, $R^{3b}$, $R^{4a}$, $R^{4b}$, $R^{5a}$, $R^{5b}$, $R^{6a}$, and $R^{6b}$ are each independently selected from hydrogen, hydroxy, and $C_1$-$C_4$alkoxy, and $C_1$-$C_4$haloalkyl, wherein at least one of $R^{2a}$, $R^{2b}$, $R^{3a}$, $R^{3b}$, $R^{4a}$, $R^{4b}$, $R^{5a}$, $R^{5b}$, $R^{6a}$, and $R^{6b}$ is $C_1$-$C_4$haloalkyl.

In some embodiments: m is 0; n is 0; $R^{2a}$ and $R^{2b}$ are each independently selected from hydrogen, hydroxy, $C_1$-$C_4$alkoxy, and $C_1$-$C_4$haloalkyl; $R^{3a}$, $R^{3b}$, $R^{5a}$, $R^{5b}$, $R^{6a}$ and $R^{6b}$ are each independently selected from hydrogen and $C_1$-$C_4$haloalkyl; and $R^{4a}$ and $R^{4b}$ are each independently selected from hydrogen, hydroxy, and $C_1$-$C_4$haloalkyl.

In some embodiments, at least one of $R^{2a}$, $R^{2b}$, $R^{3a}$, $R^{3b}$, $R^{4a}$, $R^{4b}$, $R^{5a}$, $R^{5b}$, $R^{6a}$, and $R^{6b}$ is trifluoromethyl.

In some embodiments, X and Y are each —C(O)O—.

In another aspect, disclosed is a compound of formula (IId):

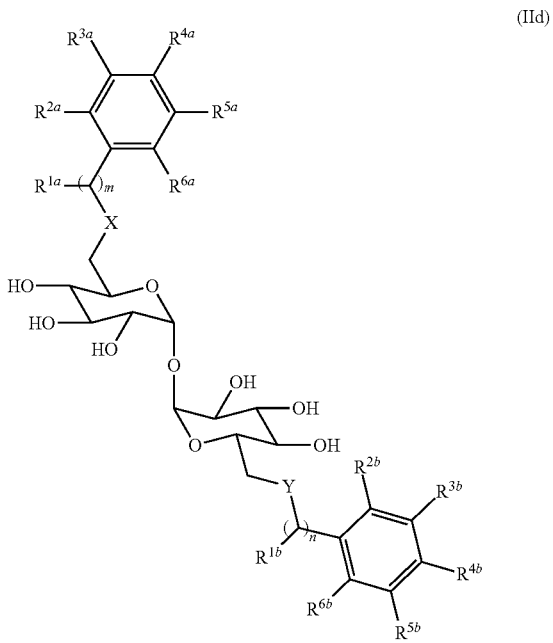

(IId)

or a pharmaceutically acceptable salt thereof, wherein:
m is 1;
n is 1;
X and Y are each independently selected from —C(O)O—, —C(O)NR$^a$—, —C(S)NR$^b$—, —NR$^c$—, and —O—;
R$^a$, R$^b$, and R$^c$ are each independently selected from hydrogen and $C_1$-$C_4$ alkyl;
$R^{1a}$ and $R^{1b}$, when present, are each independently selected from hydrogen and $C_1$-$C_4$ alkyl; and
$R^{2a}$, $R^{2b}$, $R^{3a}$, $R^{3b}$, $R^{4a}$, $R^{4b}$, $R^{5a}$, $R^{5b}$, $R^{6a}$, and $R^{6b}$ are each independently selected from hydrogen, $C_1$-$C_8$alkyl, hydroxy, $C_1$-$C_8$alkoxy, halo, $C_1$-$C_4$haloalkyl, aryl, $C_1$-$C_8$alkoxy-$C_1$-$C_8$alkoxy, $C_1$-$C_8$alkoxy-$C_1$-$C_8$alkyl, and hydroxy-$C_1$-$C_8$alkyl;

wherein each aryl is independently unsubstituted or substituted with 1, 2, or 3 substituents independently selected from $C_1$-$C_4$-alkyl, hydroxy, $C_1$-$C_4$alkoxy, halo, $C_1$-$C_4$haloalkyl, and $C_1$-$C_4$hydroxyalkyl.

In some embodiments, $R^{1a}$ and $R^{1b}$ are each hydrogen.

In some embodiments: $R^{2a}$, $R^{2b}$, $R^{4a}$, $R^{4b}$, $R^{6a}$, and $R^{6b}$ are each independently selected from hydrogen, hydroxy, and $C_1$-$C_4$alkoxy; and $R^{3a}$, $R^{3b}$, $R^{5a}$, and $R^{5b}$ are each independently selected from hydrogen and $C_1$-$C_8$alkoxy.

In some embodiments, X and Y are each —C(O)O—.

In another aspect, disclosed is a compound of formula (IIe):

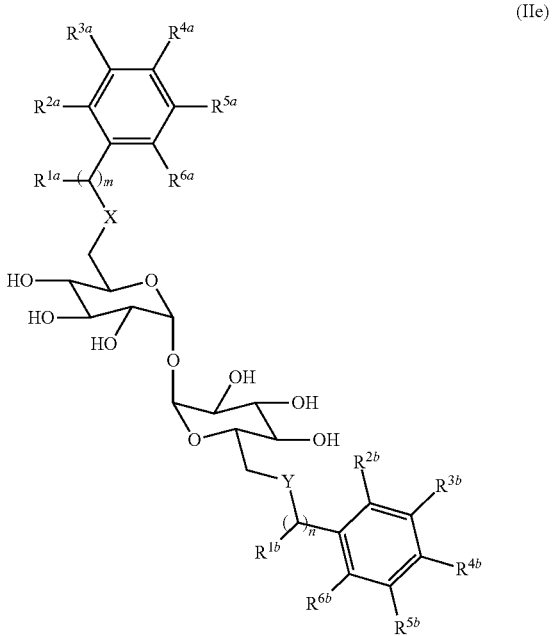

(IIe)

or a pharmaceutically acceptable salt thereof, wherein:

m is 0 or 1;

n is 0 or 1;

X and Y are each independently selected from —C(O)O—, —C(O)NR$^a$—, —C(S)NR$^b$—, —NR$^c$—, and —O—;

R$^a$, R$^b$, and R$^c$ are each independently selected from hydrogen and C$_1$-C$_4$ alkyl;

R$^{1a}$ and R$^{1b}$, when present, are each independently selected from hydrogen and C$_1$-C$_4$ alkyl;

R$^{2a}$, R$^{2b}$, R$^{5a}$, R$^{5b}$, R$^{6a}$, and R$^{6b}$ are each hydrogen; and R$^{3a}$, R$^{3b}$, R$^{4a}$, and R$^{4b}$ are each independently selected from C$_1$-C$_8$alkyl, hydroxy, C$_1$-C$_8$alkoxy, C$_1$-C$_8$alkoxy-C$_1$-C$_8$alkoxy, C$_1$-C$_8$alkoxy-C$_1$-C$_8$alkyl, and hydroxy-C$_1$-C$_8$alkyl.

In some embodiments, R$^{3a}$, R$^{3b}$, R$^{4a}$, and R$^{4b}$ are each independently selected from hydroxy and C$_1$-C$_8$alkoxy.

In some embodiments, m is 0 and n is 0.

In some embodiments, X and Y are each —C(O)O—.

In another aspect, disclosed is a compound selected from the group consisting of:

6,6'-bis(3,5-dimethoxybenzoyl)-α,α-D-trehalose, and 6,6'-bis(2-hydroxy-3,5-di-tert-butylbenzoyl)-α,α-D-trehalose, or a pharmaceutically acceptable salt thereof.

In another aspect, disclosed is a compound that is 6,6'-bis(3,5-dimethoxybenzoyl)-α,α-D-trehalose, or a pharmaceutically acceptable salt thereof.

In another aspect, disclosed is a compound that is 6,6'-bis(2-hydroxy-3,5-di-tert-butylbenzoyl)-α,α-D-trehalose, or a pharmaceutically acceptable salt thereof.

Figure 10:
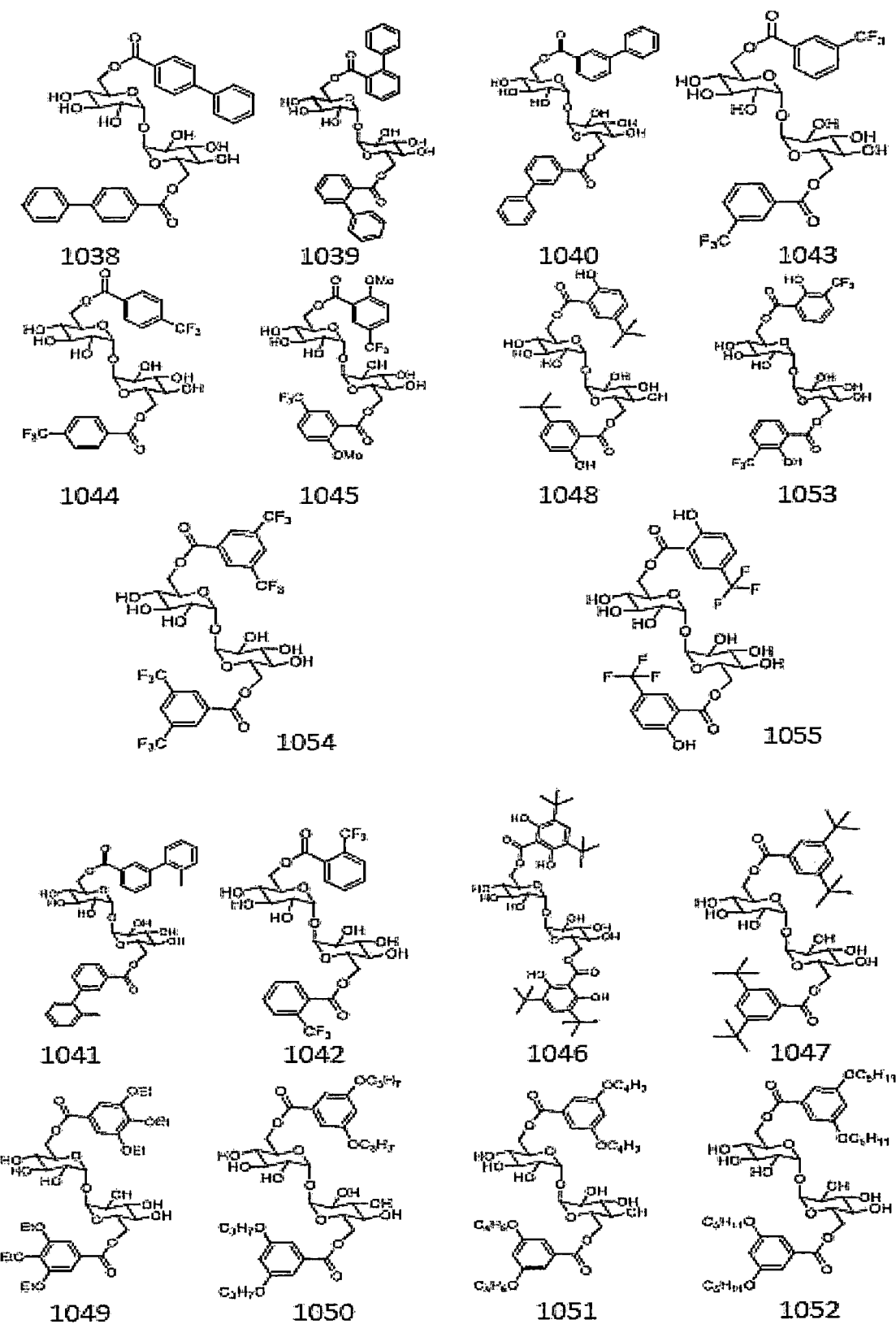
FIG. 10 shows structures of additional compounds of formula (I) or compounds of formula (II).
Figure 11:
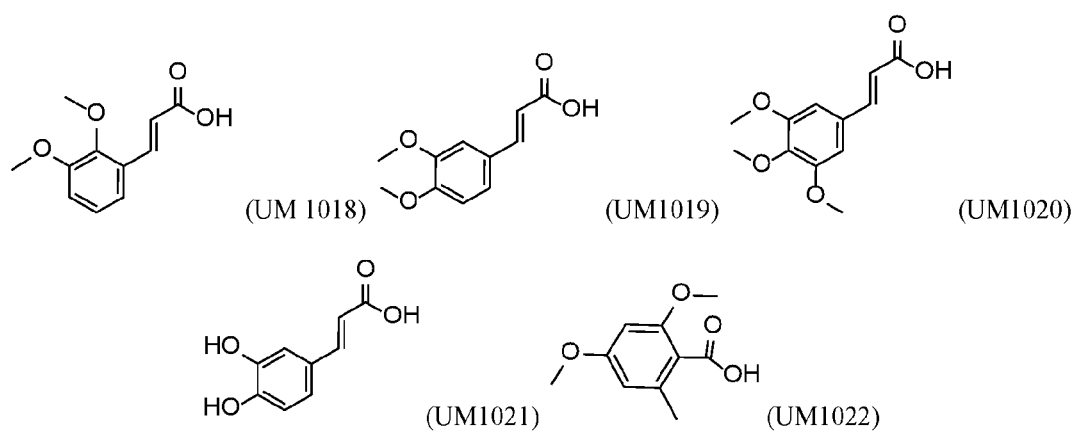
FIG. 11 shows other acids that have been used or are contemplated for use in the preparation of compounds of formula (I) or compounds of formula (II).
Figure 12:
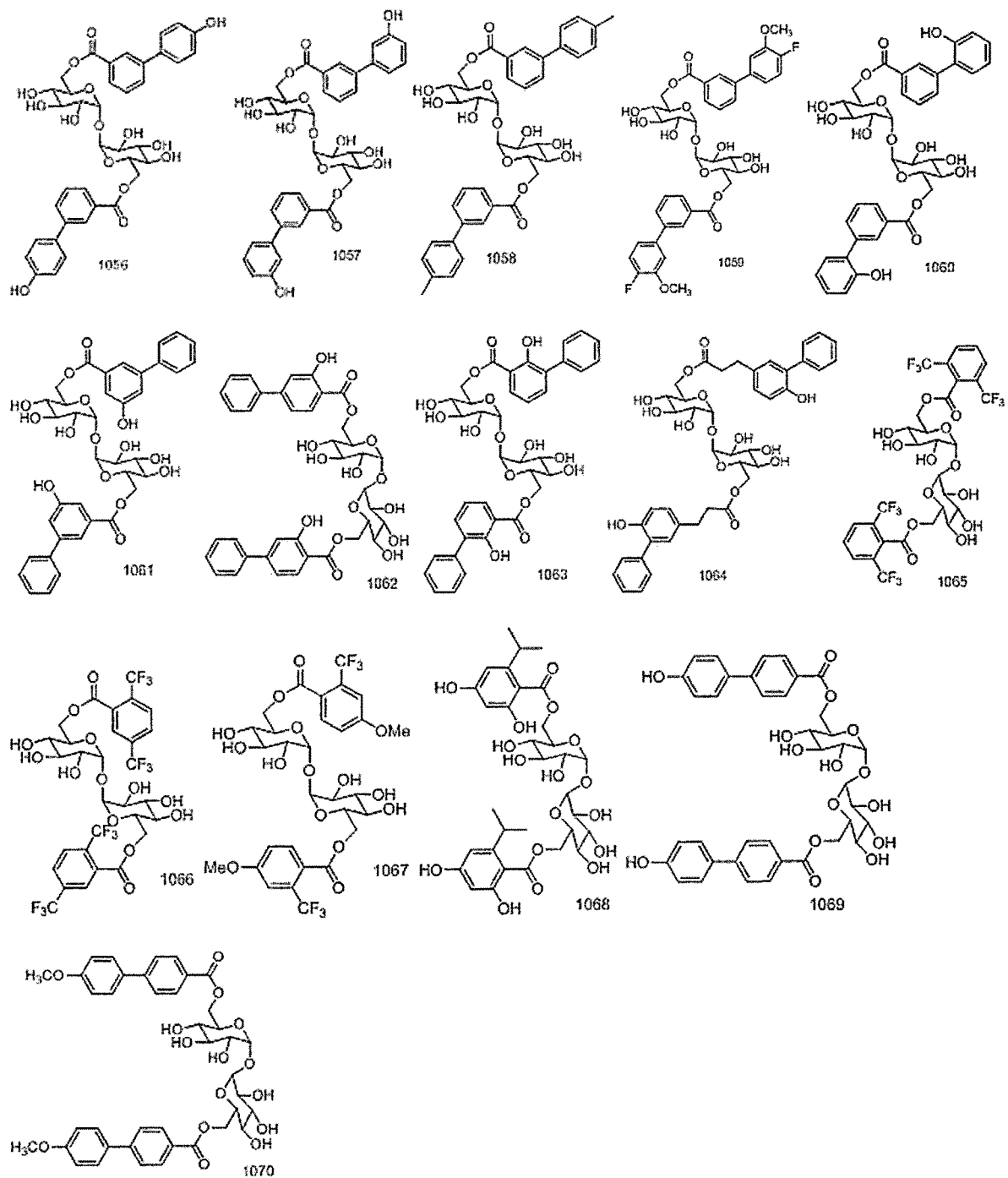
FIG. 12 shows structures of additional compounds of formula (I).
Figure 13:
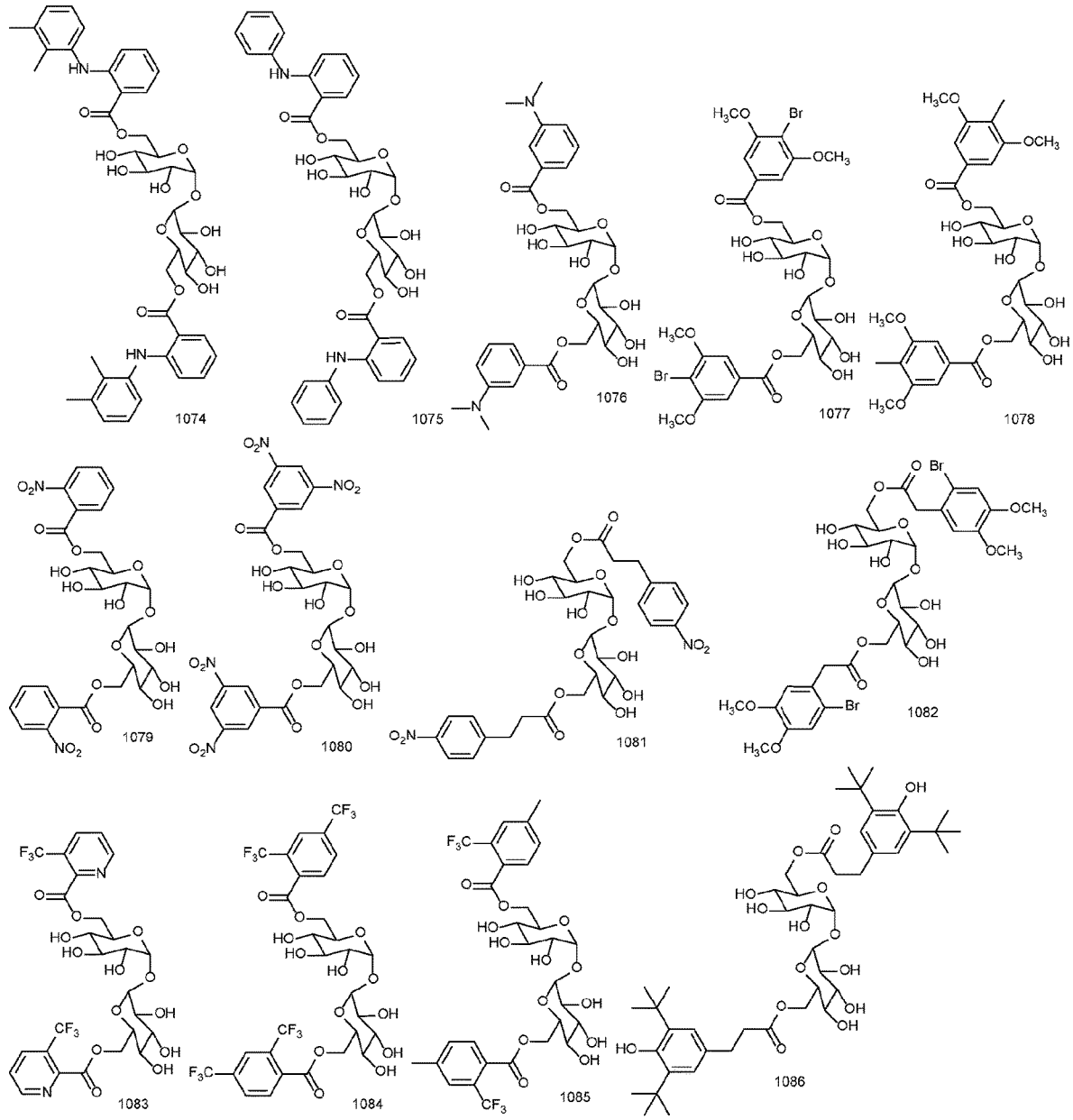
FIG. 13 shows structures of additional compounds of formula (I).
Figure 14:
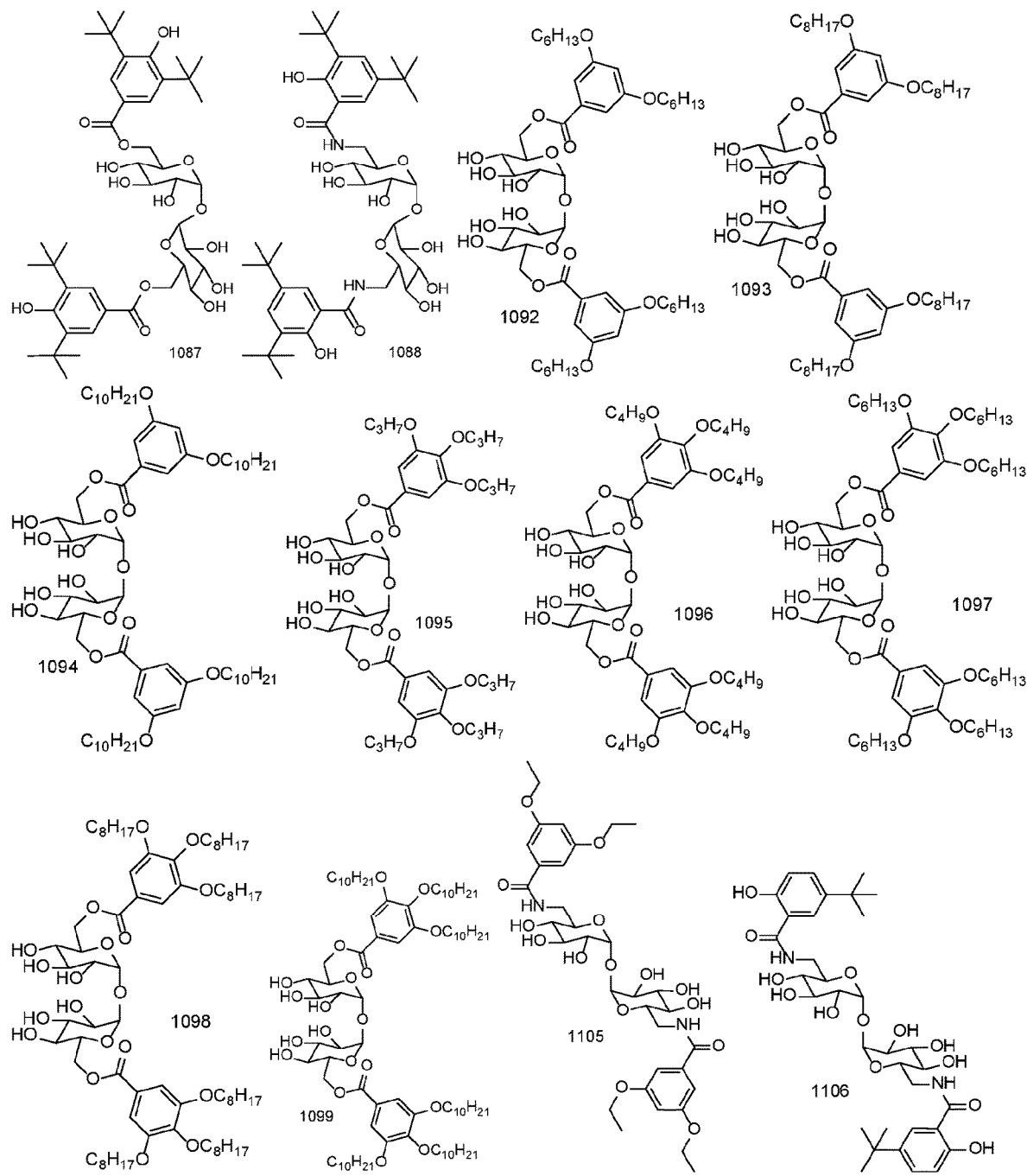
FIG. 14 shows structures of additional compounds of formula (I).
Figure 15:
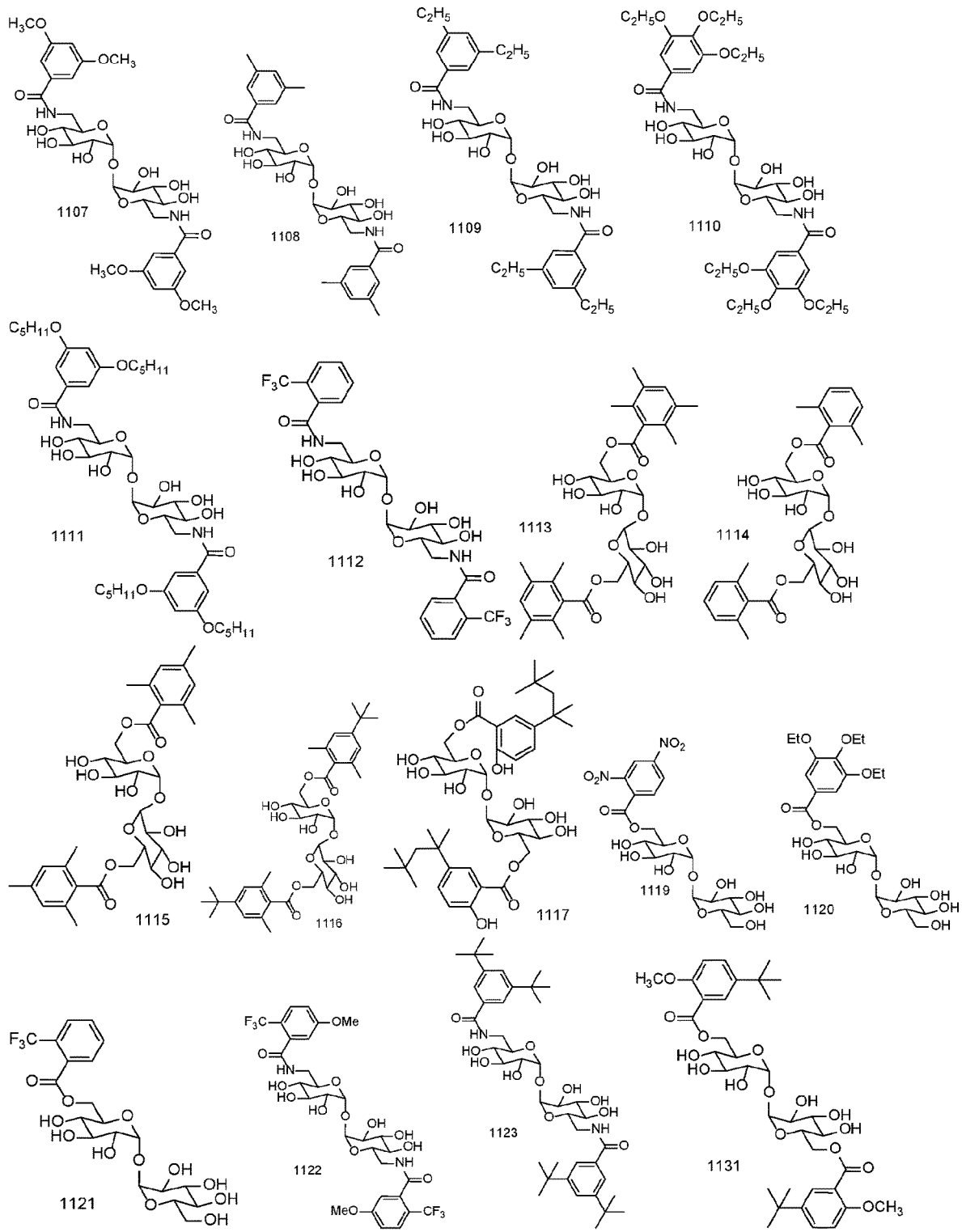
FIG. 15 shows structures of additional compounds of formula (I).
Figure 16:
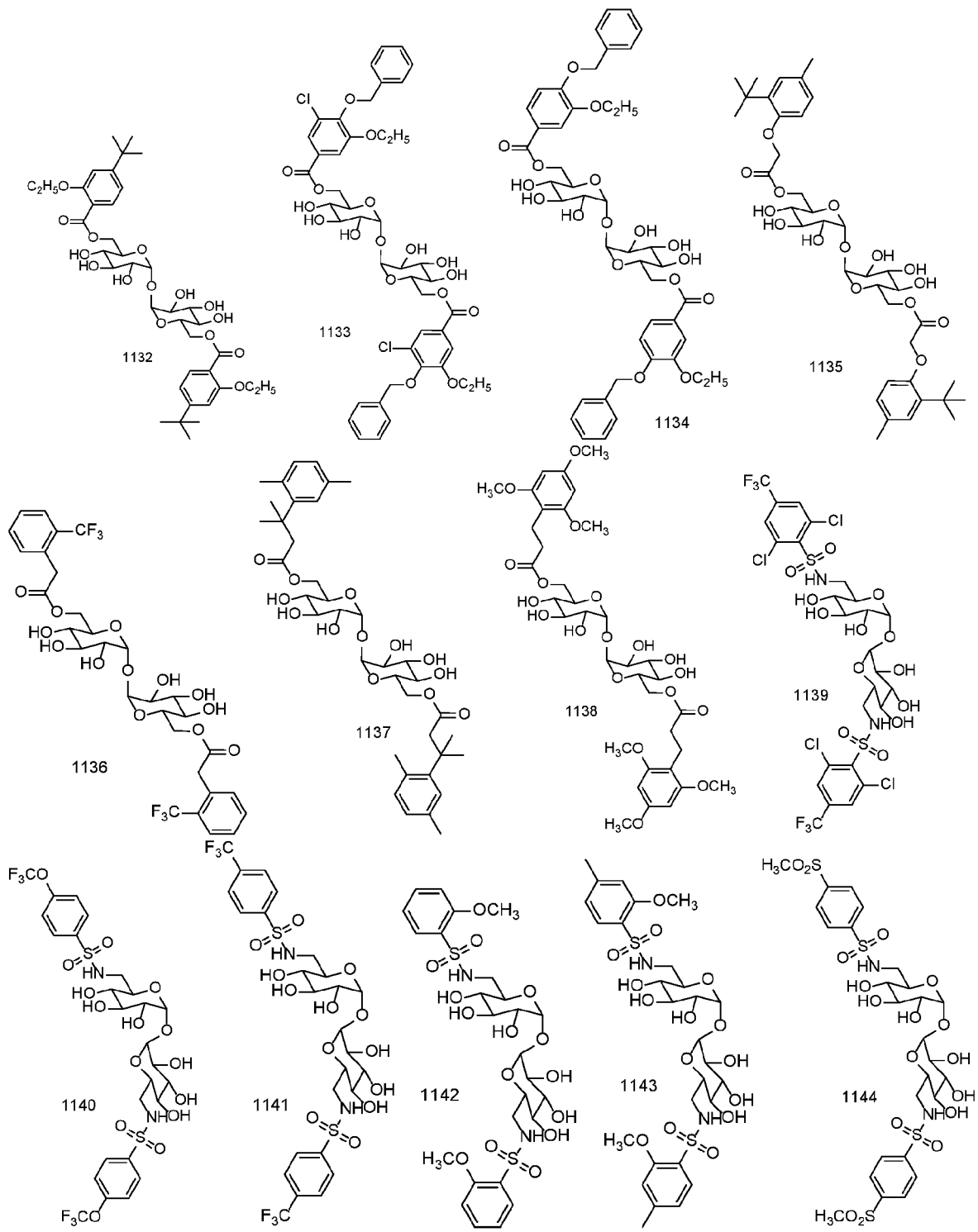
FIG. 16 shows structures of additional compounds of formula (I).
Figure 17:
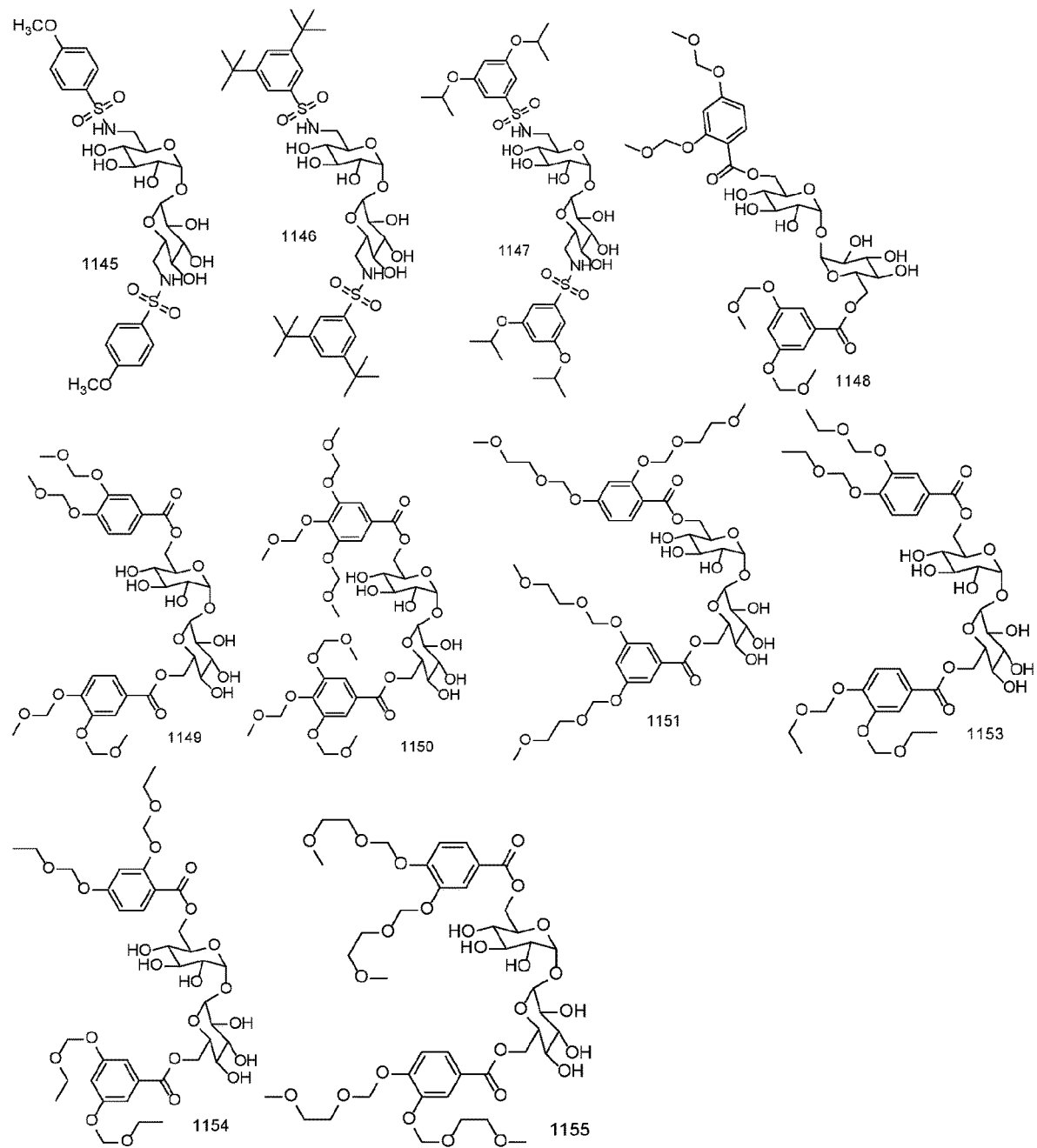
FIG. 17 shows structures of additional compounds of formula (I).

Other compounds according to the present disclosure are illustrated in FIG. 10.

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in *Pure Appl. Chem.*, 1976, 45: 13-30. The disclosure contemplates various stereoisomers and mixtures thereof and these are specifically included within the scope of this disclosure. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry," 5th edition (1989), Longman Scientific & Technical, Essex CM20 2JE, England (or more recent versions thereof), or (2) direct separation of the mixture of optical enantiomers on chiral chromatographic columns, or (3) fractional recrystallization methods.

It should be understood that the compound may possess tautomeric forms, as well as geometric isomers, and that these also constitute embodiments of the disclosure.

The present disclosure also includes an isotopically-labeled compound, which is identical to those recited in formula (I), but for the fact that one or more atoms are replaced by an atom having an atomic mass or mass number different from the atomic mass or mass number usually found in nature. Examples of isotopes suitable for inclusion in the compounds of the disclosure are hydrogen, carbon, nitrogen, oxygen, phosphorus, sulfur, fluorine, and chlorine, such as, but not limited to $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Substitution with heavier isotopes such as deuterium, i.e. $^2$H, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}$C, $^{13}$N, $^{15}$O, and $^{18}$F. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

a. Pharmaceutically Acceptable Salts

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

b. General Synthesis

Compounds of formula (I) may be prepared by synthetic processes or by metabolic processes. Preparation of the compounds by metabolic processes includes those occurring in the human or animal body (in vivo) or processes occurring in vitro.

Abbreviations used in the Schemes and descriptions that follow include the following: DCC is N,N'-dicyclohexylcarbodiimide; EDC is 1-ethyl-3-(3-dimethylaminopropyl)carbodiimide; TBTU is O-(benzotriazol-1-yl)-N,N,N',N'-tetramethyluronium tetrafluoroborate; and TMS is tetramethylsilyl.

Compounds of formula (I) may be synthesized as shown in Scheme 1.

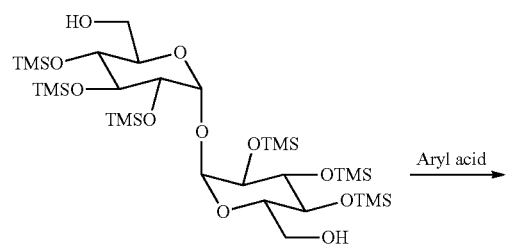

Scheme 1

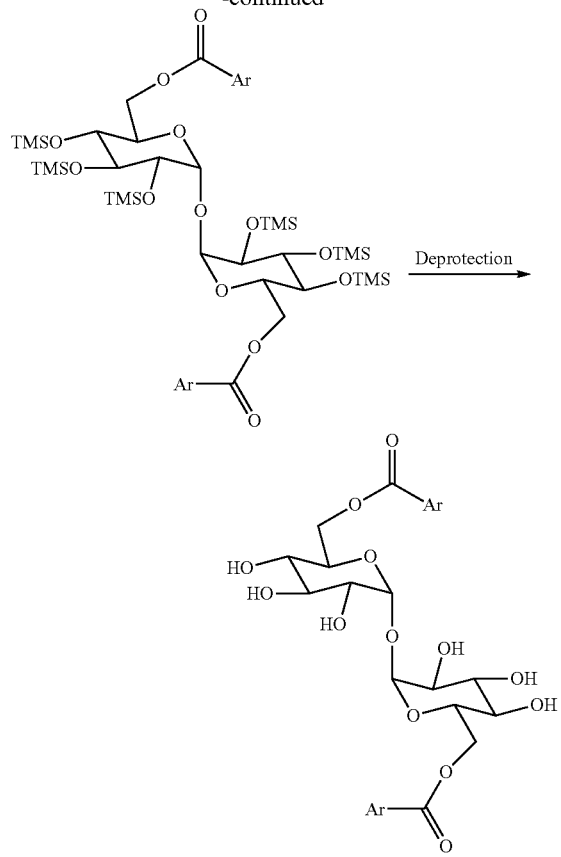

As shown in Scheme 1, the compound 2,3,4,2',3',4'-hexakis-O-trimethylsilyl-α,α-trehalose (prepared as described in Johnson et al. J. Carbohydr. Chem. 17(6), 969-974 (1998)) can be coupled with an appropriate aryl acid. This may be accomplished using a coupling agent (e.g., DCC, EDC, TBTU, or the like). Alternatively, the aryl acid may be coupled under Mitsunobu conditions, or via SN2 displacement of the corresponding 6,6'-triflate compound. More specific exemplary syntheses can be found in the Examples.

Figure 7:
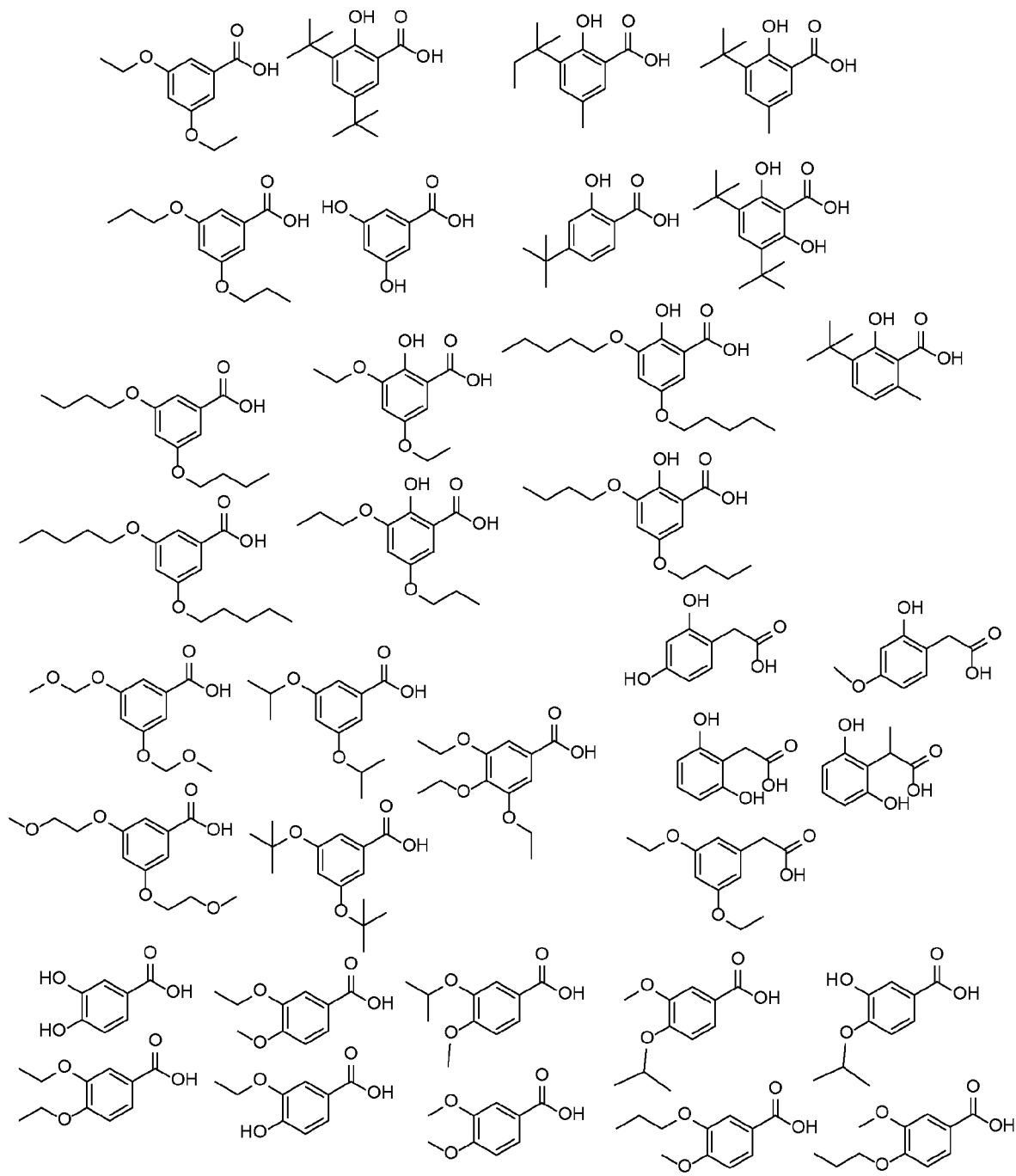
FIG. 7 shows substituted benzoic acids that have been used or are contemplated for use in the preparation of compounds of formula (I) or compounds of formula (II).
Figure 8:
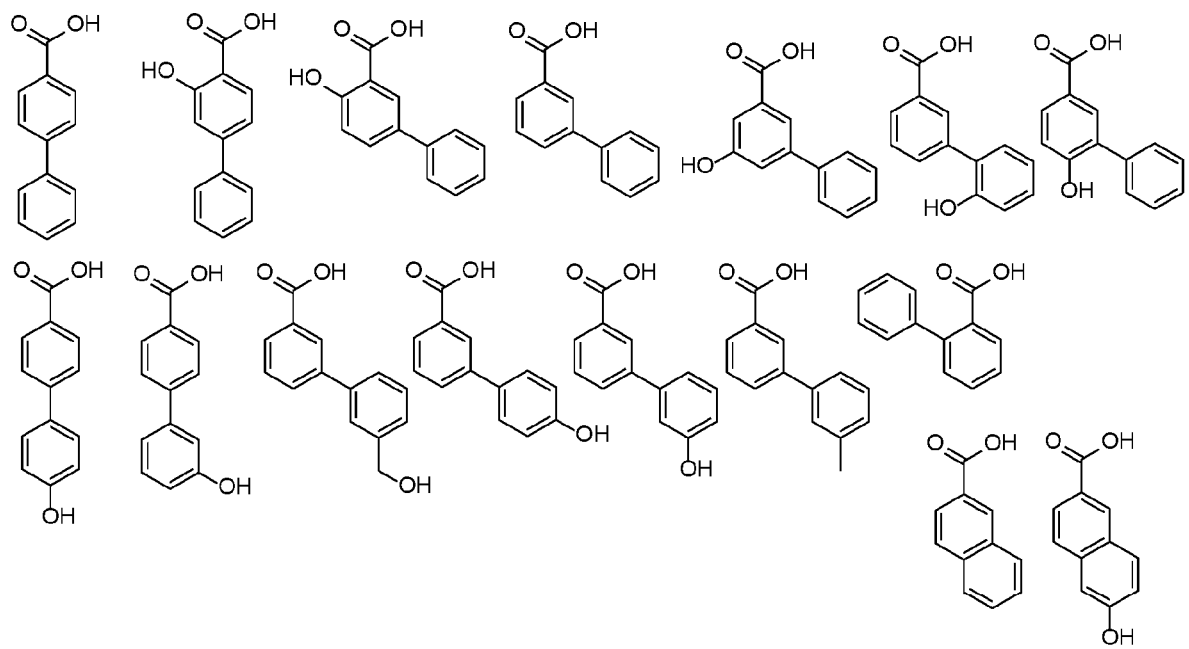
FIG. 8 shows certain diaryl substituted benzoic acids that have been used or are contemplated for use in the preparation of compounds of formula (I) or compounds of formula (II).
Figure 9:
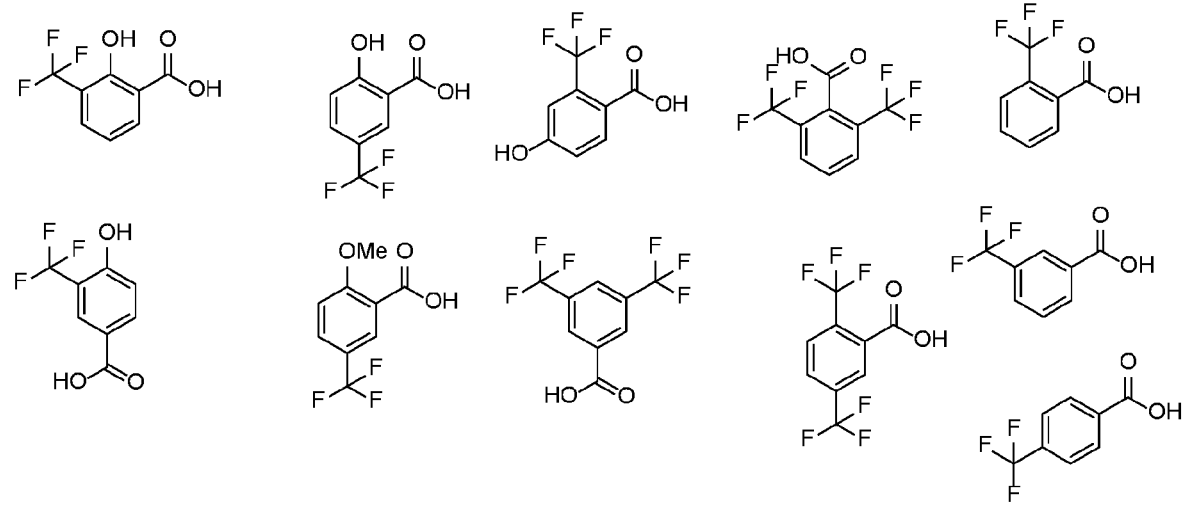
FIG. 9 shows certain trifluoromethyl-substituted benzoic acid derivatives that have been used or are contemplated for use in the preparation of compounds of formula (I) or compounds of formula (II).

Certain aryl acids, such as benzoic acids, may be commercially available. Others may be synthesized according to known methods. Benzoic acids that have been used to prepare exemplary compounds, or which are contemplated for use in preparing future compounds, include those illustrated in FIGS. 7-9.

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry," 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the disclosure. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis (4$^{th}$ ed.), John Wiley & Sons, NY (2006), which is incorporated herein by reference in its entirety. Synthesis of the compounds of the disclosure can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the disclosure as it is defined in the appended claims. All alternatives, modifications, and equivalents of the synthetic methods and specific examples are included within the scope of the claims.

c. Biological Activity

The compounds disclosed herein, including compounds of formula (I) (including compounds of formula (I), (Ia), and (Ib)) and compounds of formula (II) (including compounds of formula (II), (IIa), (IIb), (IIc), (IId), and (IIe)) may have biological activity that makes them useful as immunologic adjuvants or immunomodulators. For example, the compounds may stimulate the immune system's response to a co-administered antigen. In some embodiments, the compounds may modulate the immune response when administered as a monotherapy. In some embodiments, the compounds may have activity as Th-17 stimulating adjuvants.

In some embodiments, the compounds may simulate the production of cytokines in a sample or when administered to a subject. The compounds may stimulate the production of Th17-type cytokines. Exemplary cytokines include IL-6, IL-1β, IL-23, and TNFα. Such activity may be tested according to established methods. For example, the levels of such cytokines may be measured in samples of peripheral blood mononuclear cells (PBMCs) after exposure to the compounds.

The compounds disclosed herein, including compounds of formula (I) (including compounds of formula (I), (Ia), and (Ib)) and compounds of formula (II) (including compounds of formula (II), (IIa), (IIb), (IIc), (IId), and (IIe)) may also have biological activity that makes them useful as cytotoxic compounds, for example for treatment of cancer. In some embodiments, the compounds may inhibit or reduce the growth or proliferation of cancer cells. Such activity can be determined according to established methods.

3. COMPOSITIONS

The disclosed compounds may be incorporated into pharmaceutical compositions, adjuvant compositions, and vaccine compositions that may be suitable for administration to a subject (such as a patient, which may be a human or non-human).

a. Pharmaceutical Compositions

The disclosed compounds may be incorporated into pharmaceutical compositions. The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention (e.g., a compound of formula (I)) are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of formula (I), may be about 0.001 mg/kg to about 1000 mg/kg, 0.01 mg/kg to about 1000 mg/kg, 0.1 mg/kg to about 1000 mg/kg, 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions and formulations may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts may be formulated for administration by, for example, solid dosing, eye drop, in a topical oil-based formulation, injection, inhalation (either through the mouth or the nose), implants, or oral, buccal, sublingual, parenteral, or rectal administration. Techniques and formulations may generally be found in "Remington's Pharmaceutical Sciences," (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of *theobroma*. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, Pa.) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of an active compound (e.g., a compound of formula (I)) and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound (e.g., a compound of formula (I)), and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT® coatings (available from Evonik Industries of Essen, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound (e.g., a compound of formula (I) of formula (II)), and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the compound. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, *arachis* oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

b. Adjuvant Compositions and Vaccine Compositions

The compounds may also be incorporated in to adjuvant compositions and vaccine compositions. The vaccine compositions may further include an antigen. Suitable antigens include microbial pathogens, bacteria, viruses, proteins, glycoproteins lipoproteins, peptides, glycopeptides, lipopeptides, toxoids, carbohydrates, and tumor-specific antigens. Mixtures of two or more antigens may be employed.

The adjuvant and vaccine compositions may include an "effective amount" of the disclosed compound. In the context of an adjuvant or vaccine composition, an "effective amount" refers to an amount effective, at dosages and for periods of time necessary, to achieve the desired result (e.g., to potentiate an immune response to one or more antigens). The immune response can be measured, for example, by measuring antibody titers against an antigen, assessing the ability of a vaccine containing the compound to immunize a host in response to a disease or antigen challenge, etc. For example, administering an "effective amount" of a compound or composition to a subject increases one or more antibody titers by 10% or more over a nonimmune control, by 20% or more over a nonimmune control, by 30% or more over a nonimmune control, by 40% or more over a nonimmune control, by 50% or more over a nonimmune control, by 60% or more over a nonimmune control, by 70% or more over a nonimmune control, by 80% or more over a nonimmune control, by 90% or more over a nonimmune control, or by 100% or more over a nonimmune control.

Vaccine preparation is a well-developed art and general guidance in the preparation and formulation of vaccines is readily available from any of a variety of sources. One such example is New Trends and Developments in Vaccines, edited by Voller et al., University Park Press, Baltimore, Md., U.S.A. 1978.

The vaccine compositions of the present disclosure may also contain other compounds, which may be biologically active or inactive. For example, one or more immunogenic portions of other tumor antigens may be present, either incorporated into a fusion polypeptide or as a separate compound, within the vaccine composition. Polypeptides may, but need not, be conjugated to other macromolecules as described, for example, within U.S. Pat. Nos. 4,372,945 and 4,474,757. Vaccine compositions may generally be used for prophylactic and therapeutic purposes.

In one embodiment, the antigen in a vaccine composition is a peptide, polypeptide, or immunogenic portion thereof. An "immunogenic portion," as used herein is a portion of a protein that is recognized (i.e., specifically bound) by a B cell and/or T cell surface antigen receptor. Such immunogenic portions generally comprise at least 5 amino acid residues, more preferably at least 10, and still more preferably at least 20 amino acid residues of an antigenic protein or a variant thereof.

Immunogenic portions of antigen polypeptides may generally be identified using well known techniques, such as those summarized in Paul, *Fundamental Immunology*, 3rd ed., 243-247 (Raven Press, 1993) and references cited therein. Such techniques include screening polypeptides for the ability to react with antigen-specific antibodies, antisera and/or T cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well known techniques. An immunogenic portion of a protein is a portion that reacts with such antisera and/or T cells at a level that is not substantially less than the reactivity of the full length polypeptide (e.g., in an ELISA and/or T cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, *Antibodies: A Laboratory Manual*, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

Peptide and polypeptide antigens may be prepared using any of a variety of well-known techniques. Recombinant polypeptides encoded by DNA sequences may be readily prepared from isolated DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast, and higher eukaryotic cells, such as mammalian cells and plant cells. Preferably, the host cells employed are *E. coli*, yeast or a mammalian cell line such as COS or CHO.

Portions and other variants of a protein antigen having less than about 100 amino acids, and generally less than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See, Merrifield, *J. Am. Chem. Soc.* 85:2149-2146, 1963. Equipment for automated synthesis of polypeptides is commercially available from suppliers such as Perkin Elmer/Applied BioSystems Division (Foster City, Calif.), and may be operated according to the manufacturer's instructions.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. Nos. 4,935,233 and 4,751,180. The linker sequence may generally be from 1 to about 50 amino acids in length. Linker sequences are not required when the first and second polypeptides have nonessential N-terminal amino acid regions that can be used to separate the functional domains and prevent steric interference.

In another embodiment, a compound or adjuvant composition described herein may be used in the preparation of DNA-based vaccine compositions. Illustrative vaccines of this type contain DNA encoding one or more polypeptide antigens, such that the antigen is generated in situ. The DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143-198, 1998, and references cited therein. Appropriate nucleic acid expression systems contain the necessary DNA sequences for expression in the patient (such as a suitable promoter and terminating signal). Bacterial delivery systems involve the administration of a bacterium (such as *Bacillus*-Calmette-Guerrin) that expresses an immunogenic portion of the polypeptide on its cell surface or secretes such an epitope. In one preferred embodiment, the DNA is introduced using a viral expression system (e.g., vaccinia or other pox virus, retrovirus, or adenovirus), which typically involves the use of a non-pathogenic (defective), replication competent virus. Illustrative systems are disclosed, for example, in Fisher-Hoch et al., *Proc. Natl. Acad. Sci. USA* 86:317-321, 1989; Flexner et al., *Ann. N.Y. Acad. Sci.* 569:86-103, 1989; Flexner et al., *Vaccine* 8:17-21, 1990; U.S. Pat. Nos. 4,603, 112, 4,769,330, and 5,017,487; WO 89/01973; U.S. Pat. No. 4,777,127; GB 2,200,651; EP 0,345,242; WO 91/02805; Berkner, *Biotechniques* 6:616-627, 1988; Rosenfeld et al., *Science* 252:431-434, 1991; Kolls et al., *Proc. Natl. Acad. Sci. USA* 91:215-219, 1994; Kass-Eisler et al., *Proc. Natl. Acad. Sci. USA* 90:11498-11502, 1993; Guzman et al., *Circulation* 88:2838-2848, 1993; and Guzman et al., *Cir. Res.* 73:1202-1207, 1993. Techniques for incorporating DNA into such expression systems are well known to those of ordinary skill in the art.

Alternatively, the DNA may be "naked," as described, for example, in Ulmer et al., *Science* 259:1745-1749, 1993 and reviewed by Cohen, *Science* 259:1691-1692, 1993. The uptake of naked DNA may be increased by coating the DNA onto biodegradable beads that are efficiently transported into the cells. It will be apparent that a vaccine may comprise both a polynucleotide and a polypeptide component if desired.

Moreover, it will be apparent that a vaccine may contain pharmaceutically acceptable salts of the desired polynucleotide, polypeptide and/or carbohydrate antigens. For example, such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

The adjuvant system may exhibit strong adjuvant effects when administered over a wide range of dosages and a wide range of ratios.

The amount of antigen in each vaccine dose is generally selected as an amount which induces an immunoprotective response without significant adverse side effects in typical vaccines. Such amount will vary depending upon which specific immunogen is employed and how it is presented. Generally, it is expected that each dose will comprise about 1-1000 μg of protein, most typically about 2-100 μg, preferably about 5-50 μg. Of course, the dosage administered may be dependent upon the age, weight, kind of concurrent treatment, if any, and nature of the antigen administered.

The immunogenic activity of a given amount of a vaccine composition can be readily determined, for example by monitoring the increase in titer of antibody against the antigen used in the vaccine composition (Dalsgaard, K. *Acta Veterinia Scandinavica* 69:1-40 (1978)). Another common method involves injecting CD-1 mice intradermally with various amounts of a vaccine composition, later harvesting sera from the mice and testing for anti-immunogen antibody, e.g., by ELISA. These and other similar approaches will be apparent to the skilled artisan.

The antigen can be derived and/or isolated from essentially any desired source depending on the infectious disease, autoimmune disease, condition, cancer, pathogen, or a disease that is to be treated with a given vaccine composition. By way of illustration, the antigens can be derived from viral sources, such as influenza virus, feline leukemia virus, feline immunodeficiency virus, Human HIV-1, HIV-2, Herpes Simplex virus type 2, Human cytomegalovirus, Hepatitis A, B, C or E, Respiratory Syncytial virus, human papilloma virus rabies, measles, or hoof and mouth disease viruses. Illustrative antigens can also be derived from bacterial sources, such as anthrax, diphtheria, Lyme disease, malaria, tuberculosis, Leishmaniasis, *T. cruzi, Ehrlichia, Candida*, etc., or from protozoans such as *Babeosis bovis* or *Plasmodium*. The antigen(s) will typically be comprised of natural or synthetic amino acids, e.g., in the form of peptides, polypeptides, or proteins, can be comprised of polysaccharides, or can be mixtures thereof. Illustrative antigens can be isolated from natural sources, synthesized by means of solid phase synthesis, or can be obtained by way of recombinant DNA techniques.

In another embodiment, tumor antigens may be used in the vaccine compositions for the prophylaxis and/or therapy of cancer. Tumor antigens are surface molecules that are differentially expressed in tumor cells relative to non-tumor tissues. Tumor antigens make tumor cells immunologically distinct from normal cells and provide diagnostic and therapeutic targets for human cancers. Tumor antigens have been characterized either as membrane proteins or as altered carbohydrate molecules of glycoproteins or glycolipids on the cell surface. Cancer cells often have distinctive tumor antigens on their surfaces, such as truncated epidermal growth factor, folate binding protein, epithelial mucins, melanoferrin, carcinoembryonic antigen, prostate-specific membrane antigen, $HER^2$-neu, which are candidates for use in therapeutic cancer vaccines. Because tumor antigens are normal or related to normal components of the body, the immune system often fails to mount an effective immune response against those antigens to destroy the tumor cells. To achieve such a response, the adjuvant systems described herein can be utilized. As a result, exogenous proteins can enter the pathway for processing endogenous antigens, leading to the production of cytolytic or cytotoxic T cells (CTL). This adjuvant effect facilitates the production of antigen specific CTLs which seek and destroy those tumor cells carrying on their surface the tumor antigen(s) used for immunization. Illustrative cancer types for which this approach can be used include prostate, colon, breast, ovarian, pancreatic, brain, head and neck, melanoma, leukemia, lymphoma, etc.

In one embodiment, the antigen present in the vaccine composition is not a foreign antigen, but a self-antigen, i.e., the vaccine composition is directed toward an autoimmune disease. Examples of autoimmune diseases include type 1 diabetes, conventional organ specific autoimmunity, neurological disease, rheumatic diseases/connective tissue disease, autoimmune cytopenias, and related autoimmune diseases. Such conventional organ specific autoimmunity may include thyroiditis (Graves+Hashimoto's), gastritis, adrenalitis (Addison's), ovaritis, primary biliary cirrhosis, myasthenia gravis, gonadal failure, hypoparathyroidism, alopecia, malabsorption syndrome, pernicious anemia, hepatitis, anti-receptor antibody diseases and vitiligo. Such neurological diseases may include schizophrenia, Alzheimer's disease, depression, hypopituitarism, diabetes insipidus, sicca syndrome and multiple sclerosis. Such rheumatic diseases/connective tissue diseases may include rheumatoid arthritis, systemic lupus erythematous (SLE) or Lupus, scleroderma, polymyositis, inflammatory bowel disease, dermatomyositis, ulcerative colitis, Crohn's disease, vasculitis, psoriatic arthritis, exfoliative psoriatic dermatitis, pemphigus vulgaris, Sjögren's syndrome. Other autoimmune related diseases may include autoimmune uvoretinitis, glomerulonephritis, post myocardial infarction cardiotomy syndrome, pulmonary hemosiderosis, amyloidosis, sarcoidosis, aphthous stomatitis, and other immune related diseases, as presented herein and known in the related arts.

In one embodiment, the antigen may be covalently bonded to an adjuvant such as the compound of formula I to produce a discrete molecule which may exhibit an enhanced adjuvanting effect on the antigen, which may be greater than the adjuvanting effect attainable in the absence of such covalent bonding, as in a mixture of components (i.e., the antigen and a compound of formula (I)). The covalent bonding can be achieved by reaction through functional groups; for example in the case of the compound of formula I through a carboxylic acid group, a hydroxyl group or an aldehyde functionality. A further enhanced adjuvanting effect may be attained for such covalently-bonded antigen by incorporating a mineral salt adjuvant with such compounds. The mineral salt adjuvant preferably comprises aluminum hydroxide or aluminum phosphate, although other known mineral salt adjuvants, such as calcium phosphate, zinc hydroxide or calcium hydroxide, may be used.

The adjuvant may include other polynucleotides and/or polypeptides. It will be apparent that a vaccine may contain pharmaceutically acceptable salts of the polynucleotides and polypeptides provided herein. Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

The vaccine compositions may be formulated for any appropriate manner of administration, and thus administered, including for example, topical, oral, nasal, intravenous, intravaginal, epicutaneous, sublingual, intracranial, intradermal, intraperitoneal, subcutaneous, intramuscular administration, or via inhalation. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed.

In one illustrative embodiment, the vaccine formulations are administered to the mucosae, in particular to the oral cavity, and preferably to a sublingual site, for eliciting an immune response. Oral cavity administration may be preferred in many instances over traditional parenteral delivery due to the ease and convenience offered by noninvasive administration techniques. Moreover, this approach further provides a means for eliciting mucosal immunity, which can often be difficult to achieve with traditional parenteral delivery, and which can provide protection from airborne pathogens and/or allergens. An additional advantage of oral cavity administration is that patient compliance may be improved with sublingual vaccine delivery, especially for pediatric applications, or for applications traditionally requiring numerous injections over a prolonged period of time, such as with allergy desensitization therapies.

The vaccine compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, vaccine compositions may be formulated as a lyophilisate. Compounds may also be encapsulated within liposomes using well known technology.

The vaccine compositions may also comprise other adjuvants or immunoeffectors. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham); mineral salts (for example, aluminum, silica, kaolin, and carbon); aluminum salts such as aluminum hydroxide gel (alum), AlK$(SO_4)_2$, AlNa$(SO_4)_2$, AlNH$_4$(SO$_4$), and Al(OH)$_3$; salts of calcium (e.g., Ca$_3$(PO$_4$)$_2$), iron or zinc; an insoluble suspension of acylated tyrosine; acylated sugars; cationically or anionically derivatized polysaccharides; polynucleotides (for example, poly IC and poly AU acids); polyphosphazenes; cyanoacrylates; polymerase-(DL-lactide-co-glycoside); biodegradable microspheres; liposomes; lipid A and its derivatives; monophosphoryl lipid A; wax D from *Myco-* bacterium tuberculosis, as well as substances found in *Corynebacterium parvum, Bordetella pertussis*, and members of the genus *Brucella*); bovine serum albumin; diphtheria toxoid; edestin; keyhole-limpet hemocyanin; Pseudomonal Toxin A; choleragenoid; cholera toxin; pertussis toxin; viral proteins; and Quil A. Aminoalkyl glucosamine phosphate compounds can also be used (see, e.g., WO 98/50399, U.S. Pat. No. 6,113,918 (which issued from U.S. Ser. No. 08/853,826), and U.S. Ser. No. 09/074,720). In addition, adjuvants such as cytokines (e.g., GM-CSF or interleukin-2, -7, or -12), interferons, or tumor necrosis factor, may also be used as adjuvants. Protein and polypeptide adjuvants may be obtained from natural or recombinant sources according to methods well known to those skilled in the art. When obtained from recombinant sources, the adjuvant may comprise a protein fragment comprising at least the immunostimulatory portion of the molecule. Other known immunostimulatory macromolecules which can be used include, but are not limited to, polysaccharides, tRNA, non-metabolizable synthetic polymers such as polyvinylamine, polymethacrylic acid, polyvinylpyrrolidone, mixed polycondensates (with relatively high molecular weight) of 4',4-diaminodiphenylmethane-3,3'-dicarboxylic acid and 4-nitro-2-aminobenzoic acid (See, Sela, M., *Science* 166: 1365-1374 (1969)) or glycolipids, lipids or carbohydrates.

Within the vaccine compositions provided herein, the adjuvant composition is preferably designed to induce an immune response predominantly of the Th17 type. High levels of Th17-type cytokines (e.g., IL-6, IL-1β, IL-23, and TNFα) may favor the induction of cell mediated immune responses to an administered antigen. Following administration of a vaccine as provided herein, a patient may support an immune response that includes Th17-type responses. In some embodiments, in which a response is predominantly Th17-type, the level of Th17-type cytokines will increase to a greater extent than the level other cytokines. The levels of these cytokines may be readily assessed using standard assays. For a review of the families of cytokines, see, Mosmann and Coffman, *Ann. Rev. Immunol.* 1989, 7: 145-173.

The compositions described herein may be administered as part of a sustained release formulation (i.e., a formulation such as a capsule, sponge or gel (composed of polysaccharides, for example) that effects a slow release of compound following administration). Such formulations may generally be prepared using well known technology (see, e.g., Coombes et al., *Vaccine* 14:1429-1438, 1996) and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. Such carriers include microparticles of poly(lactide-co-glycolide), polyacrylate, latex, starch, cellulose, dextran and the like. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see, e.g., U.S. Pat. No. 5,151,254 and PCT applications WO 94/20078, WO/94/23701 and WO 96/06638). The amount of active compound contained within a sustained release formulation will vary depending upon the site of implantation, the rate and expected duration of release and the nature of the condition to be treated or prevented.

Any of a variety of known delivery vehicles may be employed within pharmaceutical compositions and vaccines to facilitate production of an antigen-specific immune response that targets cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-target effects per se and/or to be immunologically compatible with the receiver (i.e., matched HLA haplotype). APCs nay generally be isolated from any of a variety of biological fluids and organs, including tumor and peritumoral tissues, and may be autologous, allogeneic, syngeneic or xenogeneic cells.

Certain embodiments may use dendritic cells or progenitors thereof as antigen-presenting cells. Dendritic cells are highly potent APCs (Banchereau and Steinman, *Nature* 392:245-251, 1998) and have been shown to be effective as a physiological adjuvant for eliciting prophylactic or therapeutic antitumor immunity (see, Timmerman and Levy, Ann. Rev. Med. 50:507-529, 1999). In general, dendritic cells may be identified based on their typical shape (stellate in situ, with marked cytoplasmic processes (dendrites) visible in vitro), their ability to take up, process and present antigens with high efficiency and their ability to activate naive T cell responses. Dendritic cells may, of course, be engineered to express specific cell-surface receptors or ligands that are not commonly found on dendritic cells in vivo or ex vivo, and such modified dendritic cells are contemplated. As an alternative to dendritic cells, secreted vesicles antigen-loaded dendritic cells (called exosomes) may be used within a vaccine (see, Zitvogel et al., *Nature Med.* 4:594-600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1B).

APCs may generally be transfected with a polynucleotide encoding an antigen polypeptide (or portion or other variant thereof) such that the antigen polypeptide, or an immunogenic portion thereof, is expressed on the cell surface. Such transfection may take place ex vivo, and a composition or vaccine comprising such transfected cells, and the adjuvants described herein, may then be used for therapeutic purposes. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and Cell Biology* 75:456-460, 1997. Antigen loading of dendritic cells may be achieved by incubating dendritic cells or progenitor cells with the antigen polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

In one embodiment, the vaccine composition may comprise a liposome vesicle comprising the compound of formula I. Liposomes are generally produced from phospholipids or other lipid substances. Procedures for the preparation of liposomes are well known to those of skill in the art. Any lipid capable of forming vesicles that comprises the compound of formula I can be employed. For clinical application, it is desirable that the lipid be non-toxic, physiologically acceptable, and metabolizable. Common bilayer forming lipids having clinical potential are phospholipids, fatty acids, sphingolipids, glycosphingolipids, and steroids. Glycerol containing phospholipids are the most commonly used component of liposome formulations having clinical utility. One commonly used example is phosphatidylcholine or lecithin. The steroid cholesterol and its derivatives are often included as components of liposomal membranes. The tendency of liposomes to aggregate and fuse can be controlled by the inclusion of small amounts of acidic or basic lipids in the formulation. The properties of liposomes containing phospholipids are determined by the chemistry of the phospholipid. Important considerations are the hydrocarbon chain length, degree of unsaturation of the hydrocarbon chain, degree of branching of the hydrocarbon chain, and temperature of the system.

Multilamellar liposomes can be created by depositing a mixture of lipids as a thin film by evaporation under reduced pressure followed by dispersion with an excess volume of aqueous buffer containing the antigen with or without organic solvents. Another method is to mix the aqueous phase containing the antigen with small unilamellar liposomes followed by lyophilization. The multilamellar liposomes are formed when the lyophilized product is rehydrated, usually with a small amount of distilled water. The small unilamellar liposomes to be used in this process are produced by dispersing the lipids in an aqueous medium followed by a mechanical means of dispersion such as sonication, use of a high pressure device, or a solvent injection method. Large and intermediate sized unilamellar liposomes can also be produced by conventional techniques including detergent dialysis, extrusion through small pore size membranes under high pressure, freeze thawing followed by slow swelling, dehydration followed by rehydration and dilution, or dialysis of lipids in the presence of chaotropic ions. The size of the liposomes can be made more uniform by fractionation procedures such as centrifugation or size exclusion chromatography, homogenization, or capillary pore membrane extrusion.

4. METHODS OF USE

The disclosed compounds and compositions may be used in various methods, including methods for modulating an immune response in a subject, methods of inducing or enhancing immunogenicity of an antigen in a subject, and related methods. The disclosed compounds and compositions may also be used in methods of treating cancer and related methods. The disclosed compounds and compositions may also be used in methods of treatment and prevention of an autoimmune disorder or an infectious disease.

a. Modulating Immune Response

The disclosed compounds and compositions may be used in methods of modulating the immune response in a subject, comprising administering to the subject an effective amount of a compound described herein, an adjuvant composition described herein, or an immunomodulatory composition described herein.

In some embodiments, disclosed compounds and compositions may be used in a method of inducing an enhanced immune response in a subject. In some embodiments, the enhanced immune response is an immune response of a Th17-type. In some embodiments, administration of the compound or composition may induce a Th17-type immune response and not a Th1-type or Th2-type immune response.

The enhanced immune response may be induced by co-administering the compound or composition with an antigen. Suitable antigens include microbial pathogens, bacteria, viruses, proteins, glycoproteins lipoproteins, peptides, glycopeptides, lipopeptides, toxoids, carbohydrates, and tumor-specific antigens. Mixtures of two or more antigens may be employed.

In some embodiments, the disclosed compounds and compositions may be administered as a monotherapy.

b. Inducing or Enhancing Immunogenicity of an Antigen

The disclosed compounds and compositions may be used in methods of inducing or enhancing immunogenicity of an antigen in a subject, comprising administering to the subject a vaccine composition comprising the antigen and an adjuvant composition comprising an effective amount of a compound or composition described herein.

Suitable antigens include microbial pathogens, bacteria, viruses, proteins, glycoproteins lipoproteins, peptides, glycopeptides, lipopeptides, toxoids, carbohydrates, and tumor-specific antigens. Mixtures of two or more antigens may be employed.

c. Treatment of Cancer and Related Methods

The disclosed compounds and compositions may be used in methods of treating cancer, or in methods of reducing or inhibiting the proliferation of cancer cells, the methods comprising administering to a subject in need thereof a therapeutically effective amount of a compound or a composition described herein.

The methods can be used with any cancer cell or in a subject having any type of cancer, for example those described by the National Cancer Institute. Exemplary cancers may include the following:

digestive/gastrointestinal cancers such as anal cancer; bile duct cancer; extrahepatic bile duct cancer; appendix cancer; carcinoid tumor, gastrointestinal cancer; colon cancer; colorectal cancer including childhood colorectal cancer; esophageal cancer including childhood esophageal cancer; gallbladder cancer; gastric (stomach) cancer including childhood gastric (stomach) cancer; hepatocellular (liver) cancer including adult (primary) hepatocellular (liver) cancer and childhood (primary) hepatocellular (liver) cancer; pancreatic cancer including childhood pancreatic cancer; sarcoma, rhabdomyosarcoma; islet cell pancreatic cancer; rectal cancer; and small intestine cancer;

endocrine cancers such as islet cell carcinoma (endocrine pancreas); adrenocortical carcinoma including childhood adrenocortical carcinoma; gastrointestinal carcinoid tumor; parathyroid cancer; pheochromocytoma; pituitary tumor; thyroid cancer including childhood thyroid cancer; childhood multiple endocrine neoplasia syndrome; and childhood carcinoid tumor;

eye cancers such as intraocular melanoma; and retinoblastoma;

musculoskeletal cancers such as Ewing's family of tumors; osteosarcoma/malignant fibrous histiocytoma of the bone; childhood rhabdomyosarcoma; soft tissue sarcoma including adult and childhood soft tissue sarcoma; clear cell sarcoma of tendon sheaths; and uterine sarcoma;

breast cancer such as breast cancer including childhood and male breast cancer and breast cancer in pregnancy;

neurologic cancers such as childhood brain stem glioma; brain tumor; childhood cerebellar astrocytoma; childhood cerebral astrocytoma/malignant glioma; childhood ependymoma; childhood medulloblastoma; childhood pineal and supratentorial primitive neuroectodermal tumors; childhood visual pathway and hypothalamic glioma; other childhood brain cancers; adrenocortical carcinoma; central nervous system lymphoma, primary; childhood cerebellar astrocytoma; neuroblastoma; craniopharyngioma; spinal cord tumors; central nervous system atypical teratoid/rhabdoid tumor; central nervous system embryonal tumors; and childhood supratentorial primitive neuroectodermal tumors and pituitary tumor;

genitourinary cancers such as bladder cancer including childhood bladder cancer; renal cell (kidney) cancer; ovarian cancer including childhood ovarian cancer; ovarian epithelial cancer; ovarian low malignant potential tumor; penile cancer; prostate cancer; renal cell cancer including childhood renal cell cancer; renal pelvis and ureter, transitional cell cancer; testicular cancer; urethral cancer; vaginal cancer; vulvar cancer; cervical cancer; Wilms tumor and other childhood kidney tumors; endometrial cancer; and gestational trophoblastic tumor; Germ cell cancers such as childhood extracranial germ cell tumor; extragonadal germ cell tumor; ovarian germ cell tumor;

head and neck cancers such as lip and oral cavity cancer; oral cancer including childhood oral cancer; hypopharyngeal cancer; laryngeal cancer including childhood laryngeal cancer; metastatic squamous neck cancer with occult primary; mouth cancer; nasal cavity and paranasal sinus cancer; nasopharyngeal cancer including childhood nasopharyngeal cancer; oropharyngeal cancer; parathyroid cancer; pharyngeal cancer; salivary gland cancer including childhood salivary gland cancer; throat cancer; and thyroid cancer;

hematologic/blood cell cancers such as a leukemia (e.g., acute lymphoblastic leukemia including adult and childhood acute lymphoblastic leukemia; acute myeloid leukemia including adult and childhood acute myeloid leukemia; chronic lymphocytic leukemia; chronic myelogenous leukemia; and hairy cell leukemia); a lymphoma (e.g., AIDS-related lymphoma; cutaneous T cell lymphoma; Hodgkin's lymphoma including adult and childhood Hodgkin's lymphoma and Hodgkin's lymphoma during pregnancy; non-Hodgkin's lymphoma including adult and childhood non-Hodgkin's lymphoma and non-Hodgkin's lymphoma during pregnancy; mycosis fungoides; Sezary syndrome; Waldenstrom's macroglobulinemia; and primary central nervous system lymphoma); and other hematologic cancers (e.g., chronic myeloproliferative disorders; multiple myeloma/plasma cell neoplasm; myelodysplastic syndromes; and myelodysplastic/myeloproliferative disorders);

lung cancer such as non-small cell lung cancer; and small cell lung cancer;

respiratory cancers such as adult malignant mesothelioma; childhood malignant mesothelioma; malignant thymoma; childhood thymoma; thymic carcinoma; bronchial adenomas/carcinoids including childhood bronchial adenomas/carcinoids; pleuropulmonary blastoma; non-small cell lung cancer; and small cell lung cancer;

skin cancers such as Kaposi's sarcoma; Merkel cell carcinoma; melanoma; and childhood skin cancer;

AIDS-related malignancies;

other childhood cancers, unusual cancers of childhood and cancers of unknown primary site; and metastases of the aforementioned cancers.

5. KITS

In one aspect, the disclosure provides kits comprising at least one disclosed compound or a pharmaceutically acceptable salt thereof, or a composition comprising the compound or a pharmaceutically acceptable salt thereof, and one or more of:

(a) at least one antigen; and (b) instructions for administering the compound or composition.

In some embodiments, the at least one disclosed compound and the at least one antigen are co-formulated. In some embodiments, the at least one disclosed compound and the at least one antigen are co-packaged. The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

The disclosed kits can be employed in connection with disclosed methods of use.

The kits may further include information, instructions, or both that use of the kit will provide increased immunity against certain pathogens in mammals (particularly humans). The information and instructions may be in the form of words, pictures, or both, and the like. In addition or in the alternative, the kit may include the compound, a composition, or both; and information, instructions, or both, regarding methods of administration of compound, or of the composition, preferably with the benefit of treating or preventing medical conditions in mammals (e.g., humans).

The compounds and processes of the disclosure may be better understood by reference to the following examples, which are intended as an illustration of and not a limitation upon the scope of the disclosure.

6. EXAMPLES

Abbreviations used in the schemes and examples that follow are: Ar is aryl; Bu is butyl; DBU is 1,8-diazabicyclo (5.4.0)undec-7-ene; DCC is N,N'-dicyclohexylcarbodiimide; DIAD is diisopropyl azodicarboxylate; DMSO is dimethyl sulfoxide; EDC is 1-Ethyl-3-(3-dimethylaminopropyl) carbodiimide; Et is ethyl; EtOH is ethanol; IPA is isopropyl alcohol; i-Pro is isopropyl; Me is methyl; MeOH is methanol; MTBE is methyl tert-butyl ether; PPh$_3$ is triphenylphosphine; PPTS is pyridinium p-toluenesulfonate; TBAF is tetra-n-butylammonium fluoride; TBS is tert-butyldimethylsilyl or tert-butyldimethylsilane; TBSCl is tert-butyldimethylsilyl chloride; TBTU is O-(Benzotriazol-1-yl)-N,N,N',N'-tetramethyluronium tetrafluoroborate; tBu is tert-butyl; tBuOH is tert-butanol; THF is tetrahydrofuran; TLC is thin-layer chromatography; and TMS is tetramethylsilyl or tetramethylsilane.

Example 1. Exemplary Benzoic Acid Syntheses

While certain benzoic acids are commercially available, others may be synthesized using an esterification, etherification, and deprotection sequence as shown below.

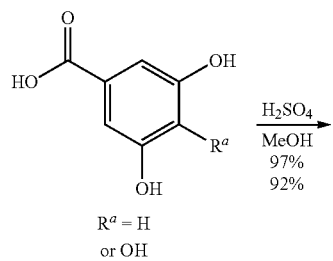

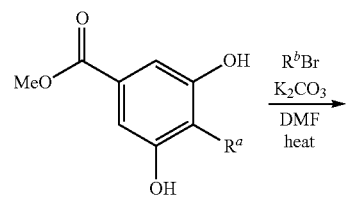

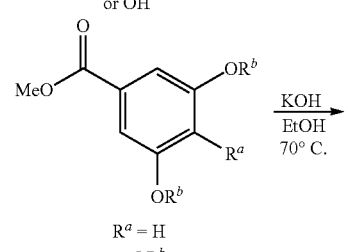

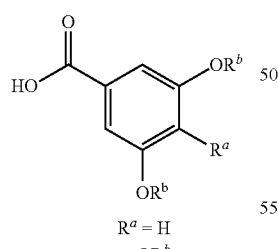

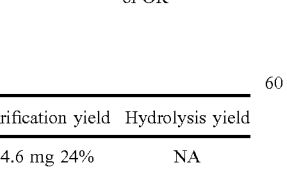

| R$^a$ = | R$^b$ = | Etherification temp | Etherification yield | Hydrolysis yield |
|---|---|---|---|---|
| OH | Et | 30° C. | 144.6 mg 24% | NA |
| OH | Et | 35° C. | 742.5 mg 99% | 482.2 mg 73% |
| H | Bu | 70° C. | 701.5 mg 85% | 494.7 mg 90% |
| H | C$_5$H$_{11}$ | 70° C. | 848.8 mg 93% | 675.4 mg 92% |

Another highly functionalized benzoic acid was prepared through an acid-catalyzed dehydrative alkylation of t-butanol with 2,6-dihydroxybenzoic acid as shown below.

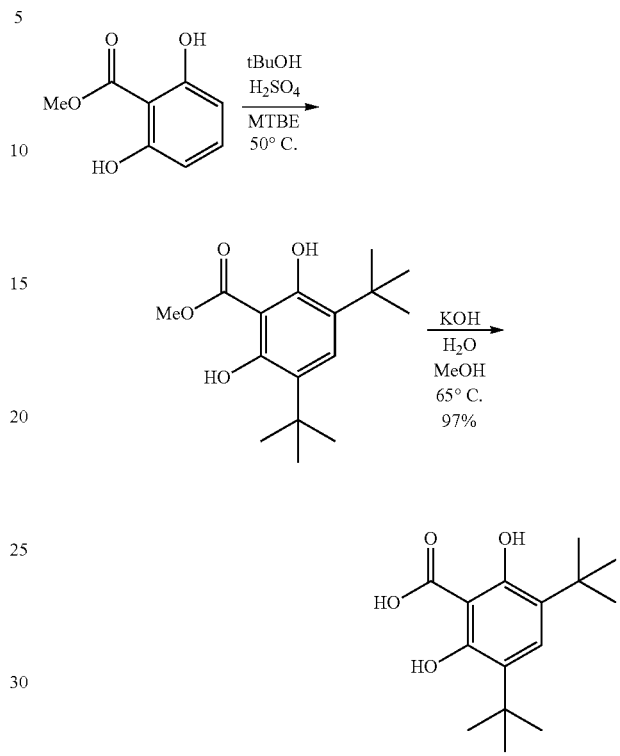

Example 2. Synthesis of Compound UM1024 Under Mitsunobu Conditions

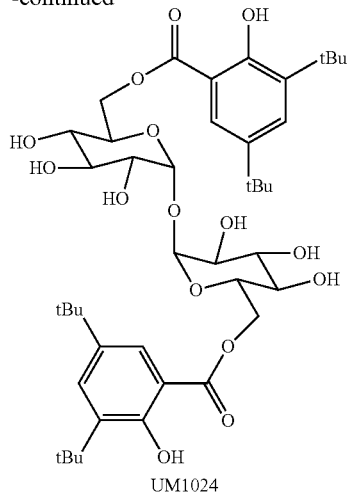

UM1024

2,3,4,2',3',4'-Hexakis-O-trimethylsilyl-α,α-trehalose (prepared as described in Johnson et al. *J. Carbohydr. Chem.* 17(6), 969-974 (1998)) (230 mg, 0.39 mmol) and triphenylphosphine (276 mg, 1.05 mmol) were dissolved in methylene chloride (10 mL) under a nitrogen atmosphere with magnetic stirring, and the solution was cooled to 0-5° C. in an ice bath. Diisopropyl azodicarboxylate (0.19 mL, 0.947 mmol) was added and the reaction stirred 10 minutes. 3,5-di-tert-butylsalicylic acid (167 mg, 0.648 mmol) was added and the reaction was monitored by TLC. After 2 hours the reaction was quenched with cold water, extracted with methylene chloride. The combined organics were dried over sodium sulfate, filtered, concentrated and the product isolated by chromatography on silica gel with a heptane to ethyl acetate gradient yielding 33.9 g (9%) 2,3,4,2',3',4'-hexakis-O-trimethylsilyl-6,6'-bis-(3,5-di-tert-butylsalisate)-α,α-trehalose. 1H NMR spectral data were recorded on an Agilent 400 MHz instrument and high resolution mass spectra were obtained on either an Agilent 6220 time of flight mass spectrometer (TOF-MS) or an Agilent 6520 time of flight quadrupole mass spectrometer (QTOF-MS)

2,3,4,2',3',4'-hexakis-O-trimethylsilyl-6,6'-bis-(3,5-di-tert-butylsalisate)-α,α-trehalose was dissolved in methylene chloride (10 mL) and methanol (10 mL) and treated with Dowex 50w X8 resin with magnetic stirring for 20 minutes. The resin was removed by filtration, the filtrate was concentrated and the product isolated by chromatography on silica gel with a chloroform to methanol gradient yielding 146 mg (48%) 6,6'-bis-(3,5-di-tert-butylsalisate)-α,α-trehalose (UM1024).

The compound 6,6'-bis-(3,5-di-iso-propylsalisate)-α,α-trehalose (UM1023) was prepared in an analogous manner (coupling yield 74.3 mg, 16).

Example 3. Synthesis of UM1024 Via SN2 Displacement

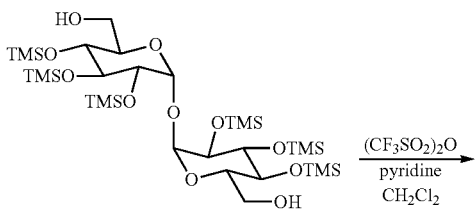

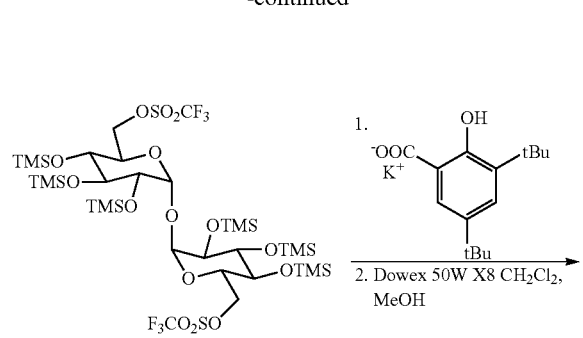

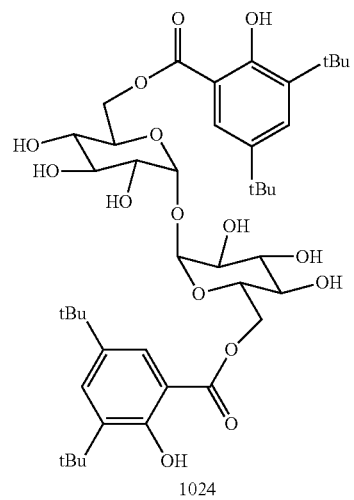

1024

2,3,4,2',3',4'-Hexakis-O-trimethylsilyl-α,α-trehalose (prepared as described in Johnson et al. *J. Carbohydr. Chem.* 17(6), 969-974 (1998)) (385 mg, 0.50 mmol) was dissolved in methylene chloride (10 mL). Pyridine (0.25 mL, 3.1 mmol) was added under nitrogen atmosphere with magnetic stirring and the solution cooled to 0-5° C. in an ice bath. Trifluoromethanesulfonic anhydride was added and the reaction was stirred for 1.5 hours. The reaction was washed with dilute hydrochloric acid, aqueous sodium bicarbonate, dried over sodium sulfate, filtered and concentrated. 3,5-di-tert-butylsalicylic acid (363 mg, 1.26 mmol) was treated with potassium trimethylsilanolate and the potassium salt was precipitated with ether and dried. The crude trehalose intermediate was dissolved in toluene (15 mL) and combined with the aryl potassium salt, 18-crown-6 (132 mg, 0.50 mmol) and the reaction was heated to 80° C. and the reaction was monitored by TLC until consumption of the starting trehalose intermediate was confirmed. The reaction was washed with aqueous sodium bicarbonate, dried over sodium sulfate, concentrated, and the product isolated by chromatography on silica gel with a heptane to ethyl acetate gradient yielding 524 mg (85%) 2,3,4,2',3',4'-hexakis-O-trimethylsilyl-6,6'-bis-(3,5-di-t-butylsalisate)-α,α-trehalose. This product was deprotected as described in Example 2 to provide 6,6'-bis-(3,5-di-tert-butylsalisate)-α,α-trehalose (UM1024).

Example 4. Synthesis of UM1015 Via Coupling Reaction

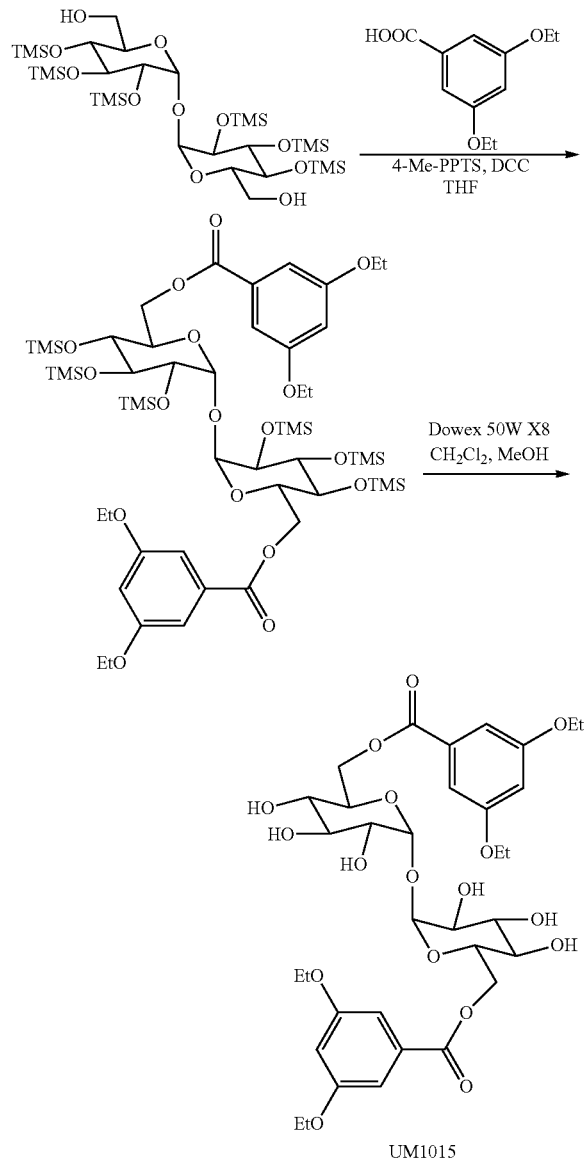

UM1015

2,3,4,2',3',4'-Hexakis-O-trimethylsilyl-α,α-trehalose (prepared as described in Johnson et al. *J. Carbohydr. Chem.* 17(6), 969-974 (1998)) (412 mg, 0.53 mmol), 3,5-diethoxybenzoic acid (276 mg, 1.31 mmol) and 4-(dimethylamino)pyridinium 4-toluenesulfonate (77 mg, 0.26 mmol) were dissolved in THE (10 mL) with magnetic stirring and the solution cooled to 0-5° C. in an ice bath. DCC was added and the reaction was allowed to warm to ambient temperature and stirred until the starting trehalose intermediate was consumed as determined by TLC. The crude reaction mixture was purified by chromatography on silica gel with a heptane to ethyl acetate gradient yielding 366 mg (60%) 2,3,4,2',3',4'-Hexakis-O-trimethylsilyl-6,6'-bis-(3,5-dimethoxybenzoate)-α,α-trehalose. This product was deprotected in a similar manner to the deprotection described in Example 2 to provide 6,6'-bis-(3,5-dimethoxybenzoate)-α,α-trehalose (Compound UM1015).

The compounds in Table 1 were prepared in a similar manner to UM1015 using appropriate phenols in the coupling reaction.

TABLE 1

| Ar | Coupling yield | Deprotection yield | Compound Ref. No. |
|---|---|---|---|
| 2-OMe, 4-OMe, 6-Me phenyl | 469.4 mg 87% | 5.5 mg 2% | UM1022 |
| 2,3-diOMe phenyl | 384.9 mg 51% | 39.2 mg 18% | UM1013 |
| 3,5-diOMe phenyl | 524.5 mg 93% | 72.7 mg 46% | UM1014 |
| 3,5-diOEt phenyl | 366.9 mg 60% | 93.5 mg 49% | UM1015 |
| 3,5-diMe phenyl | 138.1 mg 25% | 45.6 mg 70% | UM1016 |
| 3,5-diEt phenyl | 573.5 mg 98% | 172.5 mg 69% | UM1017 |

Example 5. Synthesis of Compounds Containing Lipidated Benzoic Acids

Similarly as described in Example 1, lipidated benzoic acids may be synthesized using an esterification, etherification, and deprotection sequence as shown below.

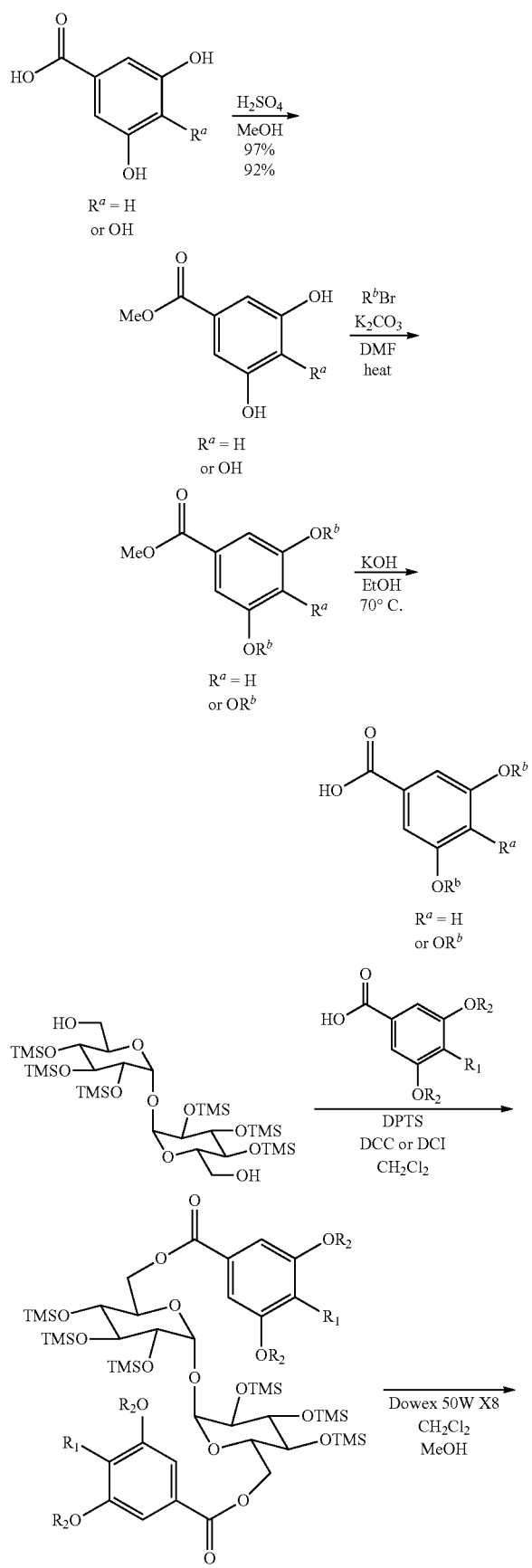

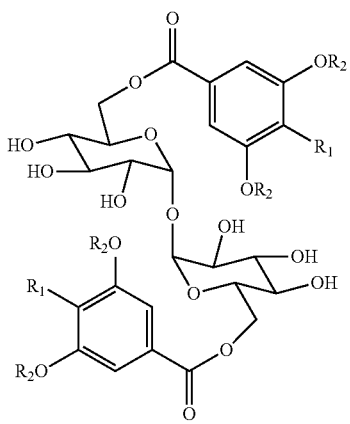

To a solution of silylated trehalose (1 mmol, 1 equiv.) in dichloromethane was added acid (3 mmol, 3 equiv.), EDCI-MeI (4 mmol, 4 equiv.), and DMAP (0.15 mmol, 0.15 equiv.). The reaction was stirred at room temperature overnight, and filtered. The filtrate was washed with cold dichloromethane. The combined layer was then washed with water and then brine, and dried over sodium sulfate and concentrated in vacuo. The crude product was purified with column chromatography (eluent:heptane:EtOAc 2:8-3:7).

Other coupling reactants were also used for the esterification: DCC (3.5 equiv)/PPTS (0.4 equiv) and DCC (3 equiv.)/DMAP (0.4 equiv.). These have been optimized and it was found that by increasing the DMAP the reaction yield increased significantly. The products were deprotected in a similar manner to the deprotection described in Example 2.

| $R^a$ | $R^b$ | Esterification yield | Deprotection | Compound Ref. No. |
|---|---|---|---|---|
| H | $CH_3$ | 333 mg, 56% | 160 mg, 71% | UM 1014 |
| H | $C_2H_5$ | 160 mg, 69% | 154 mg, 93% | UM 1015 |
| H | $C_3H_7$ | 333 mg, 56% | 160 mg, 71% | UM 1050 |
| H | $C_4H_9$ | 416 mg 69% | 201 mg 72% | UM 1051 |
| H | $C_5H_{11}$ | 538 mg 79% | 287 mg 83% | UM 1052 |
| H | $C_6H_{13}$ | 380 mg 54% | 91 mg, 37% | UM 1092 |
| H | $C_8H_{17}$ | 427 mg 56% | 60 mg, 21% | UM 1093 |
| H | $C_{10}H_{21}$ | 469 g 56% | 91 mg 29% | UM 1094 |
| $OC_2H_5$ | $C_2H_5$ | 501 mg, 59% | 74 mg, 25% | UM 1049 |
| $OC_3H_7$ | $C_3H_7$ | 347 mg 51% | 105.3 mg 50% | UM 1095 |
| $OC_4H_9$ | $C_4H_9$ | 347 mg. 48% | 33 mg, 14% | UM 1096 |
| $OC_6H_{13}$ | $C_6H_{13}$ | 462 mg, 56% | 59 mg, 18% | UM 1097 |
| $OC_8H_{17}$ | $C_8H_{17}$ | 695 mg, 75% | 208 mg, 43% | UM 1098 |
| $OC_{10}H_{21}$ | $C_{10}H_{21}$ | 583 mg, 58% | 192 mg, 70% | UM 1099 |

Example 6. Synthesis of Amide Linked Aryl and Alkyl Trehalose Compounds
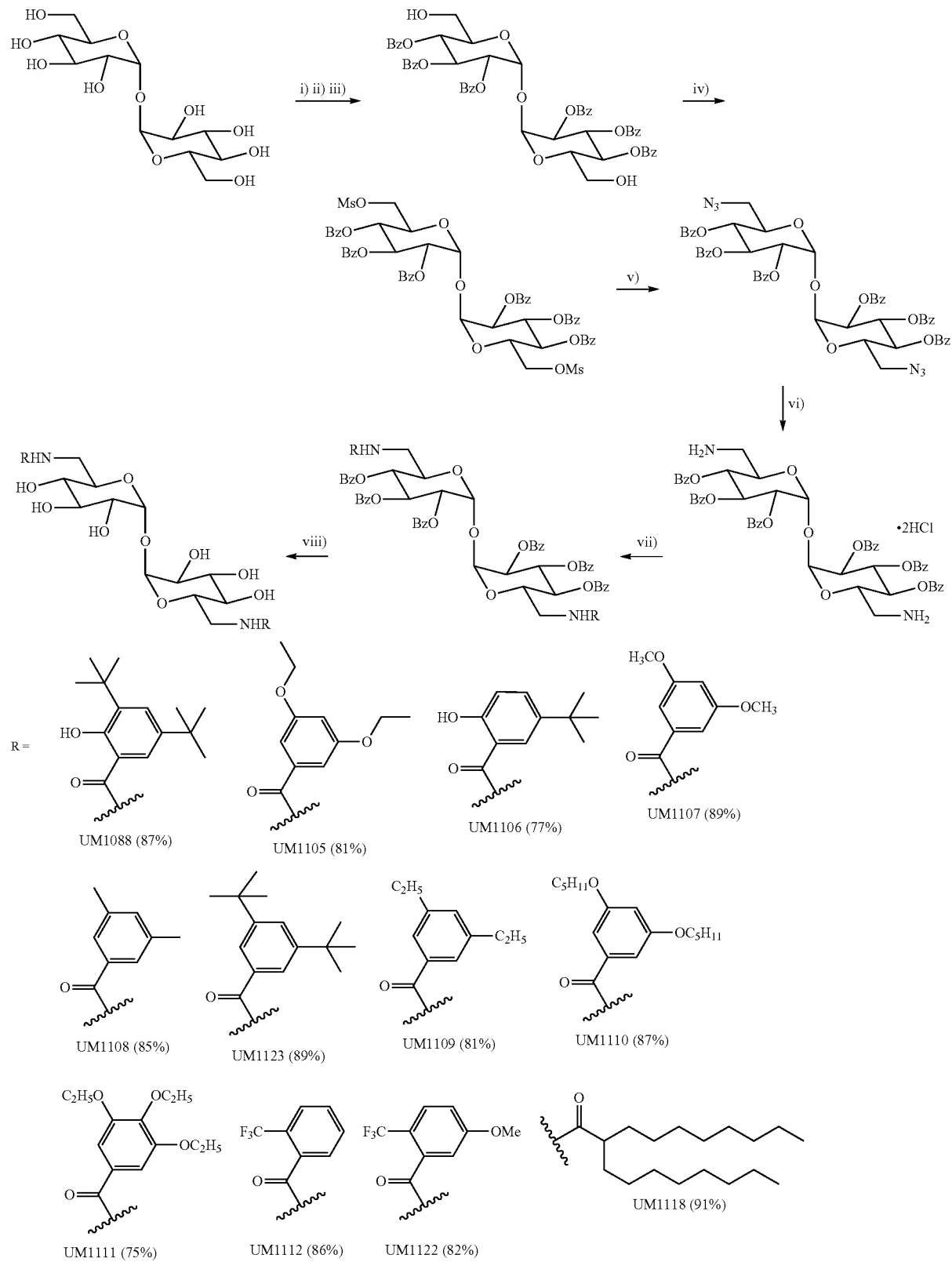

i) TrCl, Py, 40° C., 16 hr; ii) PhCOCl, 0° C. to rt, 10 hr; iii) TsOH—H$_2$O, CH$_2$Cl$_2$/MeOH (1:1), rt, 12 hr; iv) MsCl, Et$_3$N, CH$_2$Cl$_2$, 0° C., 2 hr; v) NaN$_3$, DMF, 65° C., 14 hr; vi) H2, Pd—C, EtOH/AcOH (1/2), 1 M HCl, rt, 28 hr; vii); acid, HATU, Et$_3$N, CH$_2$Cl$_2$; 0° C., 4 hr; viii) 30% MeONa/MeOH, rt, 5 hr.

2,3,4,2',3',4'-Hexakis-O-benzoyl-α,α-trehalose (prepared as described in *Chem Biol Drug Des* 2015, 86 (5), 1017-29) was combined with acid (3 equiv.), 1-[bis(dimethylamino) methylene]-1H-1,2,3-triazolo[4,5-b]pyridinium 3-oxide hexafluorophosphate (HATU, 3 equiv.) in anhydrous dichloromethane and triethylamine (3 equiv.) at 0° C. The reaction was stirred at 0° C. for 2 hrs and then diluted with dichloromethane. The organic layer was washed with water and then with brine and dried over magnesium sulfate. The crude product was purified by column chromatography (Heptane:EtOAc 2:8-1:1).

Example 7. Synthesis of Amide Linked Aryl and Alkyl Trehalose Compounds

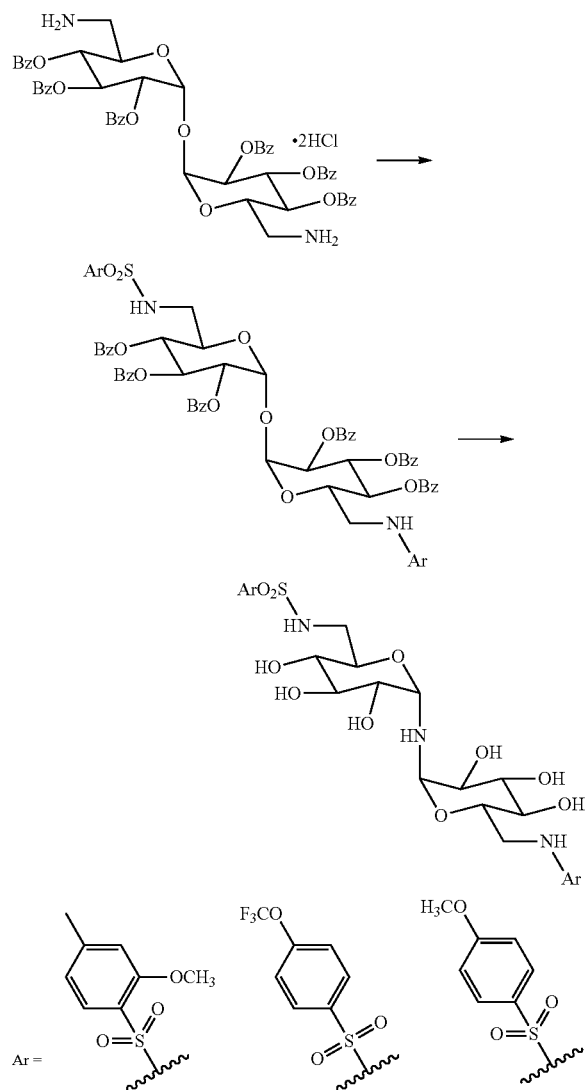

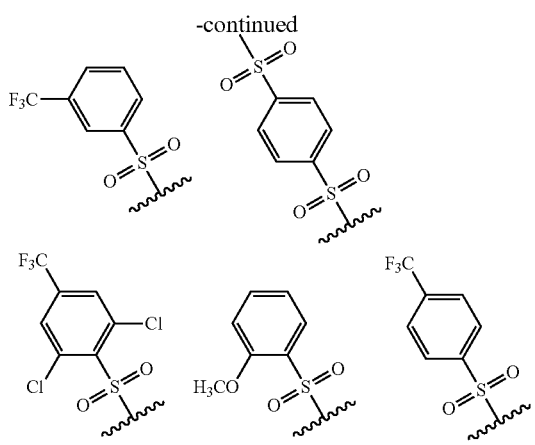

Solid sodium bicarbonate (2 equiv.) was added to a solution of the trehalose amine dihydrochloride (1 equiv.) in methanol. After stirring for 5 min, dichloromethane was added, and the mixture was evaporated at rt. dichloromethane was added and evaporated to aid complete removal of methanol. A solution of the residue in dry dichloromethane was treated with triethyl amine (3.0 equiv.) followed by substituted sulfonyl chloride (2.4 equiv.) and stirred at room temperature under nitrogen for 24 hrs. The reaction mixture was diluted with dichloromethane and washed with water, satd. sodium bicarbonate, and then again with water. The organic layer was concentrated in vacuo and purified by chromatography with (99:1) dichloromethane-methanol as eluent gave the desired product.

Example 8. Biological Activity

Figure 1B:
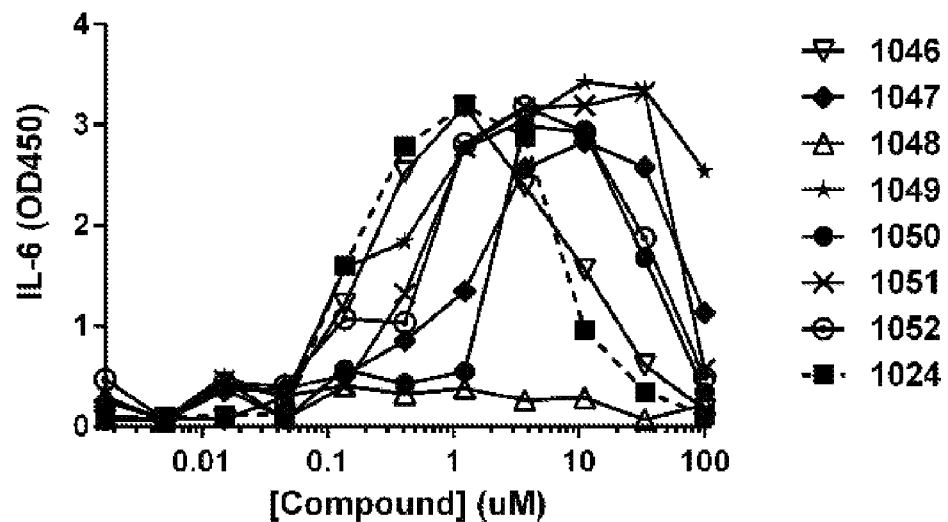
Figure 1B:
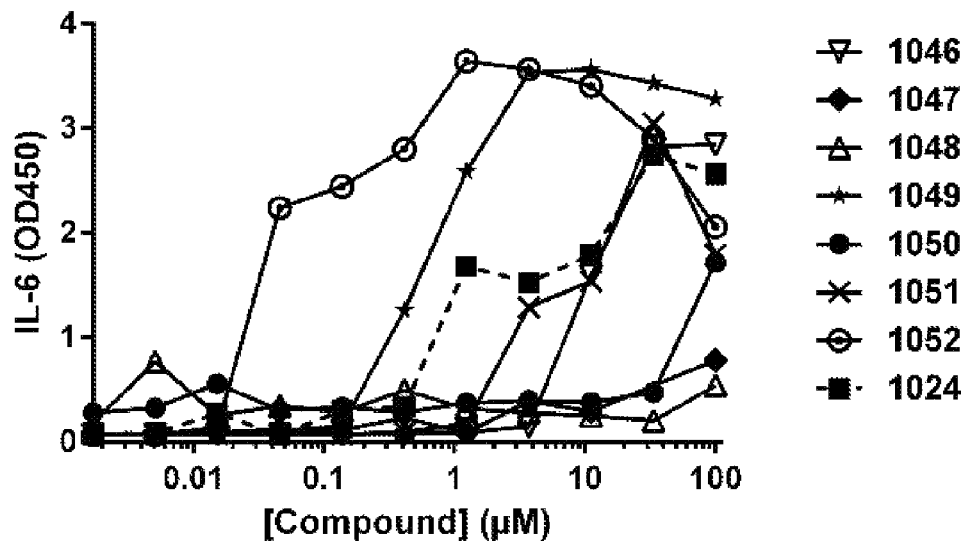

A. Cytokine Response of Peripheral Blood Mononuclear Cells (PBMCs) Treated with Compounds Tumor necrosis factor alpha (TNFα) and IL-6 production in peripheral blood mononuclear cells (PBMCs) was measured after exposure to various concentrations of the DAT compounds synthesized as shown above. Initial studies focused on two different methods of delivery of the DAT compounds to PBMC cultures. In the first delivery method, the indicated derivative compound was dissolved in isopropanol, serially diluted, and then dried to the bottom of a tissue culture plate. In the second delivery method, the indicated derivative compound was dissolved in DMSO and serially diluted into tissue culture media. In each method, PBMCs were added to the compounds and incubated at 37° C. TNFα (FIG. 1A) and IL-6 (FIG. 1B) were measured after 18-24 hours after treatment by ELISA assay.

B. Cytokine Analysis of the Supernatants of Stimulated, Freshly Prepared PBMCs

Figure 2:
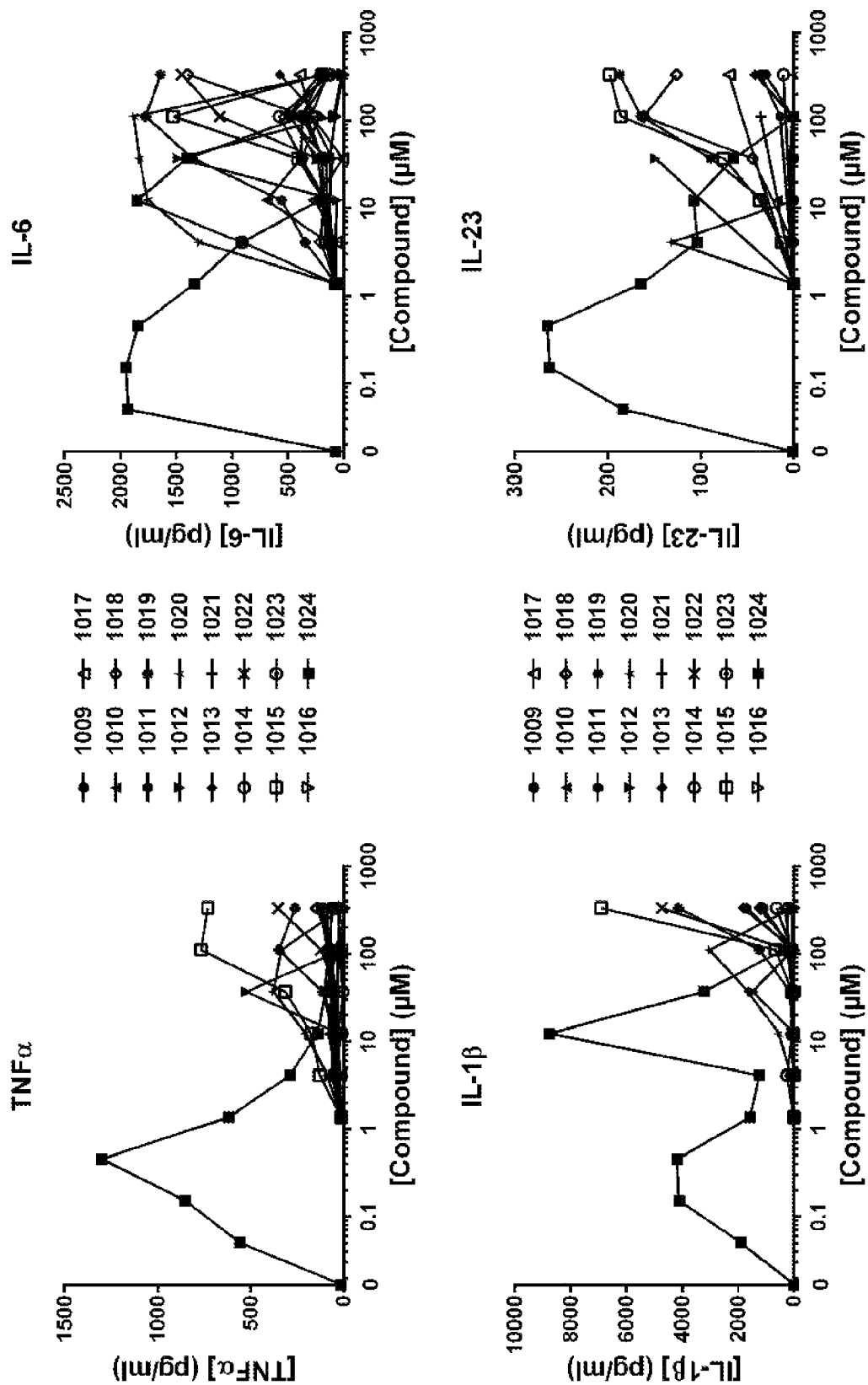
FIG. 2 shows the cytokine response in the supernatants from freshly prepared PBMCs stimulated with varying concentrations of select DAT compounds solubilized in DMSO and diluted into media.

Supernatants from the freshly prepared PBMCs stimulated with DAT compounds solubilized in DMSO (Example 5A) were analyzed for the cytokines that help drive Th1 cell or Th17 cell adaptive immune responses; IFNγ, IL-12 p70, IL-6, IL-1β, and IL-23. Immunoassay results for IL-6, IL-1β, IL-23, and TNFα are shown in FIG. 2. Minimal amounts of IL-12p70 were detected and IFNγ was undetectable. Therefore, both are not reported. TNFα responses from Example 5A were validated for the higher responding compounds (UM1009, UM1015, UM1017, UM1019, UM1020, UM1021, UM1022, UM1023 and UM1024).

C. IL-6 Induction in Fresh Human PBMCs

The most active compounds were screened for IL-6 levels in fresh PBMCs from multiple donors as indicated in FIG.

Figure 3:
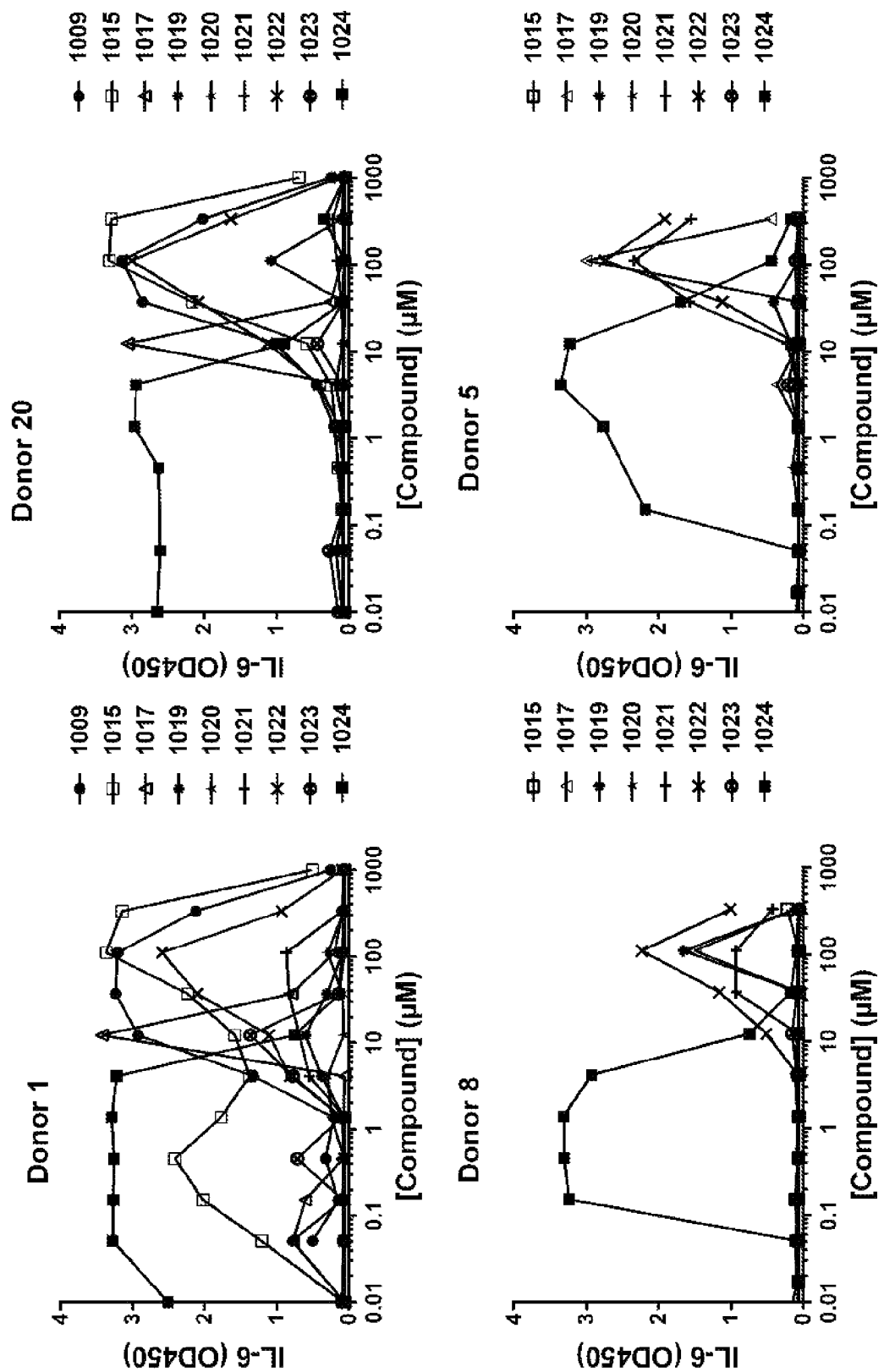
FIG. 3 shows the IL-6 response in the supernatants from freshly prepared PBMCs stimulated with varying concentrations of select DAT compounds solubilized in DMSO and diluted into media.

3. The isolated PBMCs were exposed to increasing concentrations of the indicated compounds resuspended in DMSO and serially diluted in media. IL-6 levels were determined from supernatants eighteen hours after treatment (FIG. 3).

Compound UM1024 was the most potent compound for induction of cytokines from human PBMCs demonstrating over 1000× increased potency (EC50) relative to other compounds. Compound 1023, which has an isopropyl group, exhibited lower activity suggesting the tert-butyl side chain off the aryl group may be largely responsible for the potency in UM1024. Compound UM1015 demonstrated potent, robust activity in only 3 of 5 donors (1, 20 and 15) suggesting high donor-to-donor variability with this compound. Similar structures, such as 1014 the dimethyl aryl ether, were inactive. These data show that the length or number of carbons and aryl substitution pattern at this position are important for biological activity.

Compound UM1022, the dimethoxy derivative, reproducibly induced potent, robust IL-6 production. Compound UM1021 contains a linker between the trehalose and the aryl group and while it induced some cytokine production it was quite diminished in terms of absolute level. This suggests that pi-pi interactions of a requisite phenylalanine proximal to the proposed binding site may be important for the observed activity.

D. Signaling Response of HEK-Blue™ Mincle Reporter Cells to the Compounds

Figure 4A:
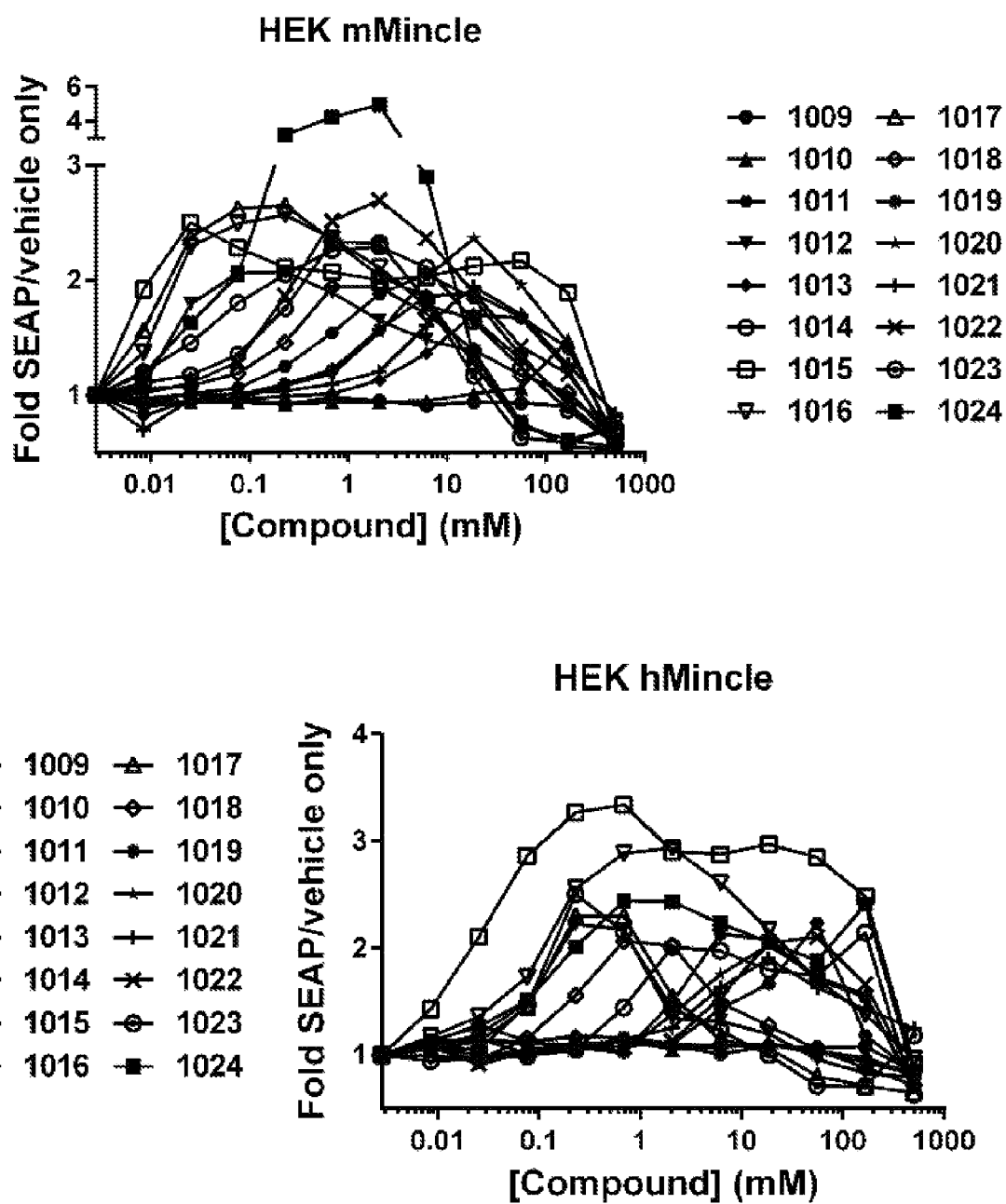
FIG. 4 shows the NF-κB secreted embryonic alkaline phosphatase (SEAP) production in the supernatants of HEK-Blue Mincle Mouse or Human reporter cells (FIG. 4A) and TNFα cytokine production in a murine macrophage cell line (FIG. 4A) stimulated with varying concentrations of select DAT compounds.

Compounds were also tested in the commercial reporter Hek-Blue™ cell lines. Hek-Blue™ cells were treated with increasing concentrations of the indicated compound for 18 to 24 hours. Isolated supernatants were measured for NF-κB secreted embryonic alkaline phosphatase (SEAP) production with QUANTI-Blue™ reagent (FIG. 4A). SEAP production was robust for both the mouse and human reporter lines (FIG. 4A), indicating strong signaling through the Mincle receptor in both human and murine systems.

In the mouse reporter cell line, UM1024 displayed a distinct very high peak at low concentration of compound (FIG. 4A). Unlike the cytokine profiles observed in PBMCs, UM1024 did not display a large leftward potency shift in comparison with other compounds.

E. TNFα Induction in Mouse Macrophage Cells

Figure 4B:
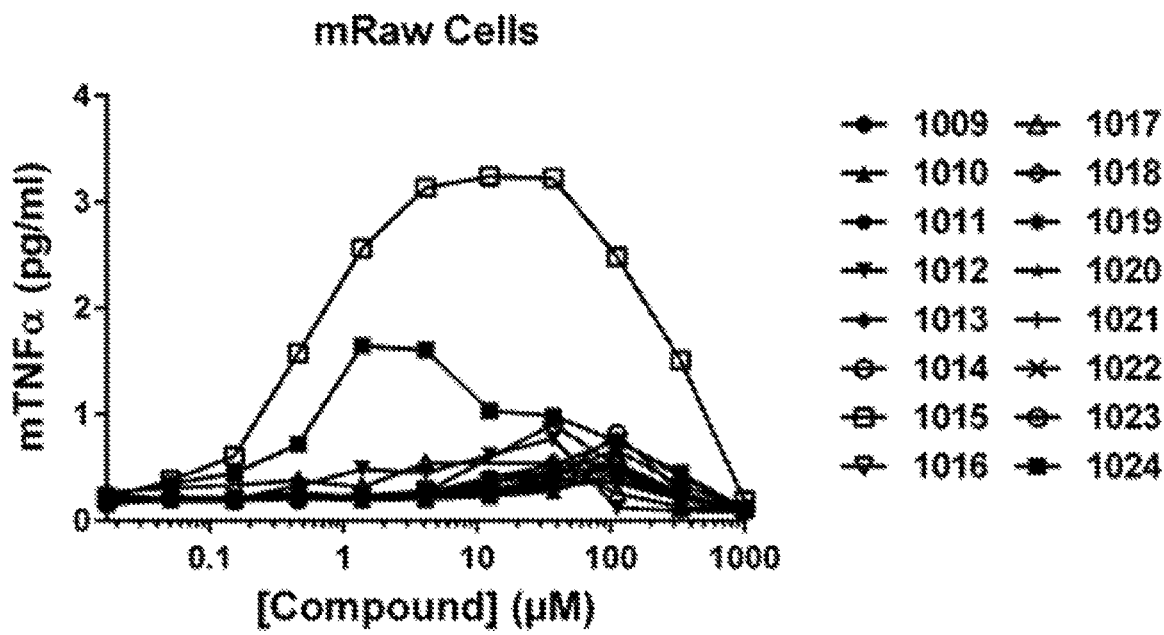
Figure 4B:
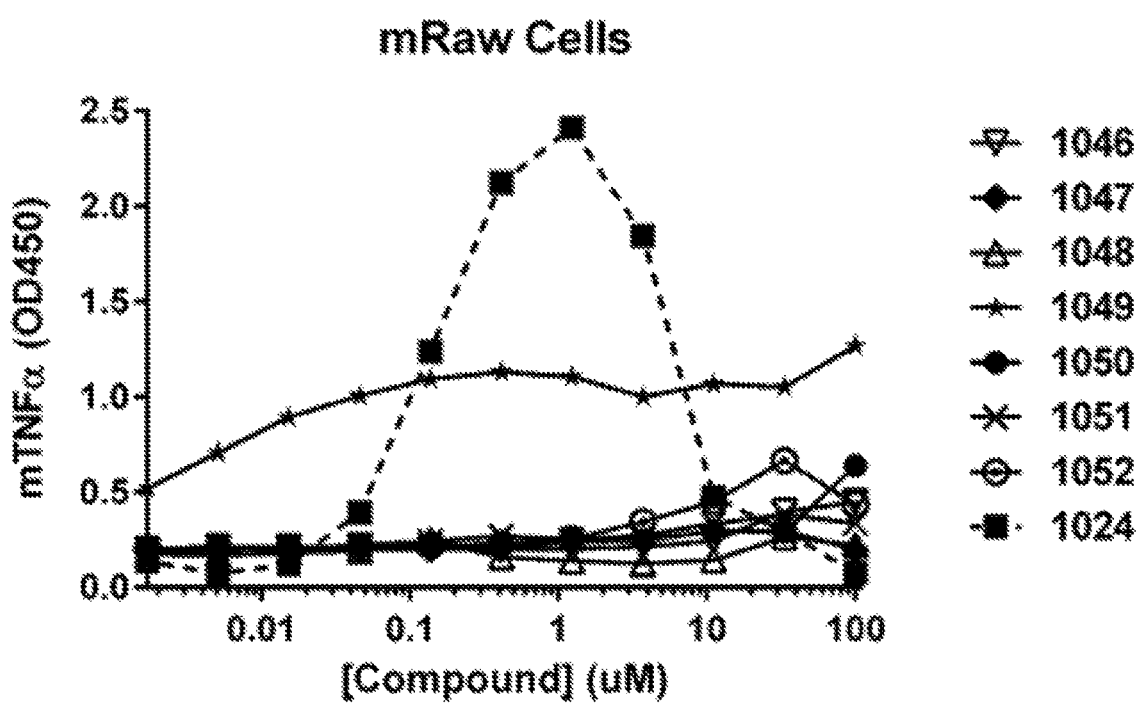

Compounds were also tested in a mouse macrophage cell line (FIG. 4B). RAW264.7 cells were subjected to increasing concentrations of the compounds and assessed for production of the cytokine TNFα. Many compounds were able to stimulation cytokine production from the mouse cells, suggesting they are active in this species, but the overall levels and potency were greatly diminished vs. human cells.

TABLE 2

Summary of Cytokine Response

| UM# | Maximum cytokine response Murine | Minimal Effective Concentration Murine (μM) | Maximum cytokine response h-IL-6 (OD) | Minimal Effective Concentration h-IL-6 (μM) |
| --- | --- | --- | --- | --- |
| 1013 | 3 | 37 | NR | NR |
| 1014 | 3.3 | 37 | NR | NR |
| 1015 | 3.5 | 12.3 | 3.6 | 111 |
| 1016 | 3 | 4.1 | 1.5 | 1000 |
| 1017 | 2.5 | 4.1 | NR | NR |
| 1018 | 3.5 | 37 | 1.3 | 333 |
| 1019 | 2.3 | 111 | 2 | 333 |
| 1020 | 3.2 | 33.3 | 1.5 | 333 |
| 1021 | 3 | 333 | 2 | 333 |
| 1022 | 3.3 | 37 | 3 | 333 |
| 1023 | 2.5 | 0.45 | NR | NR |
| 1024 | 3 | 0.45 | 3.5 | 1 |
| 1038 | NR | NR | NR | NR |
| 1039 | 0.9 | 33 | NR | NR |
| 1040 | 0.9 | 100 | NR | NR |
| 1041 | 1.2 | 33 | 1.3 | 5 |
| 1042 | 0.9 | 11 | 2 | 50 |
| 1043 | NR | NR | NR | NR |
| 1044 | NR | NR | NR | NR |
| 1045 | 1.3 | 0.05 | NR | NR |
| 1046 | 0.8 | 0.4 | 3 | 20 |
| 1047 | 0.9 | 1.2 | 1 | 11 |
| 1048 | NR | NR | NR | NR |
| 1049 | 1.3 | 0.13 | 3.3 | 2 |
| 1050 | NR | NR | 3.3 | 9 |
| 1051 | 1.3 | 0.13 | 2.5 | 6 |
| 1052 | 1.3 | 0.13 | 3.3 | 0.08 |
| 1053 | NR | NR | 0.5 | 100 |
| 1054 | NR | NR | 1.5 | 100 |
| 1055 | NR | NR | NR | NR |
| 1056 | NR | NR | NR | NR |
| 1057 | 1.8 | 33 | NR | NR |
| 1058 | 2.5 | 33 | NR | NR |
| 1059 | 1.8 | 33 | NR | NR |
| 1060 | NR | NR | 3.3 | 33.3 |
| 1061 | 3 | 100 | NR | NR |
| 1062 | 3 | 100 | 3 | 100 |
| 1063 | 2.5 | 100 | NR | NR |
| 1064 | 2.5 | 100 | NR | NR |
| 1065 | 2.5 | 100 | 3 | 3.7 |
| 1066 | 3 | 100 | 2.6 | 33.3 |
| 1067 | 1.5 | 100 | NR | NR |
| 1068 | NR | NR | NR | NR |
| 1069 | NR | NR | NR | NR |
| 1070 | 2 | 100 | 3 | 33.3 |
| 1074 | 2 | 1.2 | 3.5 | 33.3 |
| 1075 | 2.2 | 3.7 | 3.5 | 20 |
| 1076 | 1.3 | 3.7 | NR | NR |
| 1077 | NR | NR | 2.5 | 100 |
| 1078 | NR | NR | NR | NR |
| 1079 | NR | NR | NR | NR |
| 1080 | 1 | 33 | 2 | 100 |
| 1081 | NR | NR | NR | NR |
| 1082 | 1.7 | 33 | 0.5 | 100 |
| 1083 | NR | NR | NR | NR |
| 1084 | 2.9 | 33 | 3 | 100 |
| 1085 | 2.2 | 33 | 3 | 100 |
| 1086 | 3 | 0.13 | 3 | 33.3 |
| 1087 | 3 | 0.13 | 3 | 33.3 |
| 1088 | 1.3 | 0.4 | 3.5 | 2.5 |
| 1092 | <.001 | 3.4 | 3.3 | 3.7 |
| 1093 | <.001 | 3.4 | 3.4 | 1.2 |
| 1094 | <.001 | 3.4 | 3.4 | 1.2 |
| 1095 | 0.001 | 3.4 | 3.3 | 3.7 |
| 1096 | 0.005 | 3 | 3.2 | 2.5 |
| 1097 | 0.005 | 3.4 | 3.3 | 3.7 |
| 1098 | 0.04 | 3.4 | 3.4 | 11 |
| 1099 | 0.005 | 3.4 | 3.2 | 11 |
| 1105 | 11 | 3 | NR | NR |
| 1106 | 11 | 3 | NR | NR |
| 1107 | NR | NR | NR | NR |
| 1108 | 33 | 3 | NR | NR |
| 1109 | 0.4 | 3.2 | NR | NR |
| 1110 | 11 | 2.5 | 1 | 100 |
| 1111 | 0.13 | 3.3 | 2.5 | 33.3 |
| 1112 | 2 | 100 | NR | NR |
| 1113 | 11 | 2.5 | NR | NR |
| 1114 | 11 | 2.5 | NR | NR |
| 1115 | 11 | 3.3 | NR | NR |
| 1116 | 0.005 | 3 | 2.3 | 100 |
| 1117 | 11 | 3 | 9 | 33.3 |
| 1119 | 11 | 2.2 | NR | NR |
| 1120 | 11 | 2.5 | 0.3 | 100 |

TABLE 2-continued

Summary of Cytokine Response

| UM# | Maximum cytokine response Murine | Minimal Effective Concentration Murine (μM) | Maximum cytokine response h-IL-6 (OD) | Minimal Effective Concentration h-IL-6 (μM) |
|---|---|---|---|---|
| 1121 | 11 | 2.5 | NR | NR |
| 1122 | NR | NR | NR | NR |
| 1123 | 0.13 | 3.3 | 2.7 | 33.3 |
| 1131 | NT | NT | NR | NR |
| 1132 | NT | NT | 2.6 | 100 |
| 1133 | NT | NT | NR | NR |
| 1134 | NT | NT | 0.5 | 100 |
| 1135 | NT | NT | NR | NR |
| 1136 | NT | NT | NR | NR |
| 1137 | NT | NT | 1 | 100 |
| 1138 | NT | NT | NR | NR |
| 1139 | NT | NT | NR | NR |
| 1140 | NT | NT | NR | NR |
| 1141 | NT | NT | NR | NR |
| 1142 | NT | NT | NR | NR |
| 1143 | NT | NT | NR | NR |
| 1144 | NT | NT | NR | NR |
| 1145 | NT | NT | NR | NR |
| 1146 | NT | NT | NR | NR |
| 1147 | NT | NT | NR | NR |
| 1148 | NT | NT | NR | NR |
| 1149 | NT | NT | NR | NR |
| 1150 | NT | NT | NR | NR |
| 1151 | NT | NT | NR | NR |
| 1152 | NT | NT | NR | NR |
| 1153 | NT | NT | NR | NR |
| 1154 | NT | NT | NR | NR |
| 1155 | NT | NT | NR | NR |

NT—not tested;
NR—no response

F. Formulations and Immunological Response

Liposomal formulations were created for in vitro and in vivo evaluation of the compounds. In these formulations, the lipid to adjuvant molar ratio was held constant at 89:11, respectively, wherein the lipid concentration was 11.174 μmol/mL. Lipid films were rehydrated in 10 mM Tris buffer at pH=7.4. Liposomal formulations were prepared with 1 mole percent of a fluorescent-lipid dye, (N-(7-Nitrobenz-2-Oxa-1,3-Diazol-4-yl)-1,2-Dihexadecanoyl-sn-Glycero-3-Phosphoethanolamine (NBD-PE), which incorporates in the lipid bilayer of the liposomes and allows for visualization of cell-types by flow cell cytometry. Final formulations were sterile filtered using a two stage 0.8/0.2 μm PES syringe filter.

The formulations were characterized by dynamic light scattering (DLS) for particle size analysis and adjuvant concentrations were quantified by UV absorption for UM1024. DDA containing liposomal formulations required brief sonication at 50° C. for 10-15 minutes to achieve a homogeneous suspension. No significant impact on particle size, zeta potential or PDI values was seen in formulations containing adjuvants when compared with their blank formulations at neutral pH A second set of liposomal formulations were made to compare UM1024 and TDB at a molar ratio of DDA:DSPC:adjuvant of 22:67:11. Lipid concentrations in these formulations was 8.38 mg/mL while adjuvant concentration varied proportional to its molecular weight.

Compound UM1024 in liposomal formulations was tested in vivo to determine their ability to promote humoral and cell-mediated immune responses against a *Mycobacteria tuberculosis* (Mtb) vaccine antigen, M72. M72 is a recombinant protein that combines sequences from two mycobacterial proteins Mtb32a and Mtb39a which are expressed in BCG and *M. tuberculosis* strains, contain human $CD4^+$ and $CD8^+$ T cell epitopes, and are highly conserved in over 45 *Mycobacteria* strains, including multi- and extreme-drug resistant strains and covering all lineages tested so far.

Figure 5A:
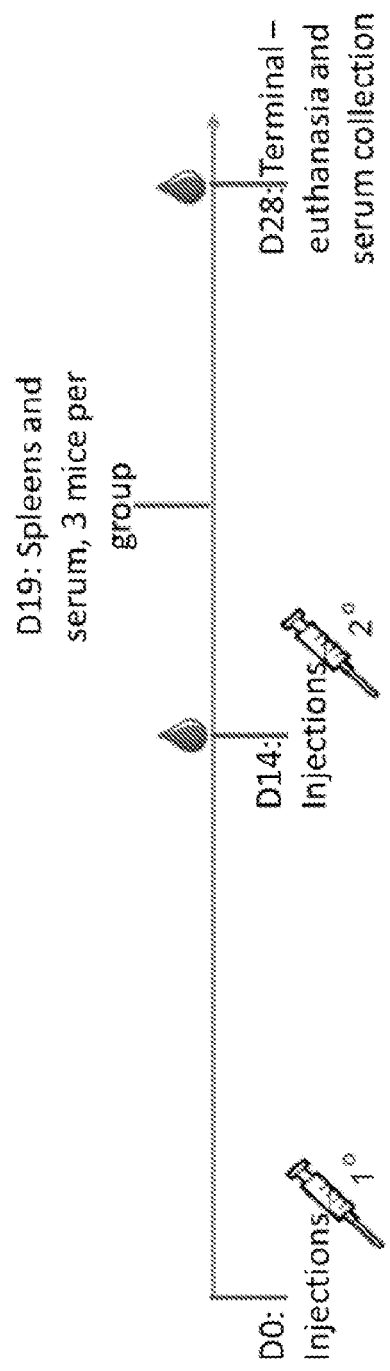
FIG. 5 shows the anti-M72 antibody response in mouse splenocytes (FIG. 5B) following two rounds of immunization (FIG. 5A).

Balb/c mice were immunized intramuscularly (i.m.) with 0.125 μg M72 and varying doses of different CLR adjuvant candidates (Table 3) in liposomal formulations. The vaccination timeline was as shown in FIG. 5A. At day 19 (5 days post-secondary immunization), 3 mice per group were euthanized. Spleens were used for T cell restimulation assays and intracellular cytokine staining to delineate antigen-specific CD4 and CD8 effector T cells, as defined by their production of IFNγ (Th1), IL-5 (Th2) or IL-17 (Th17).

TABLE 3

Antigen and adjuvant formulations used to assess the immune response to mice to i.m. vaccinations with Mtb antigen M72 in combination with various CLR adjuvant candidates. M72 antigen was used at a dose of 0.125 μg per mouse.

| Group | Description | Nmol (CLR ligand) | mice # |
|---|---|---|---|
| A | Naïve |  | 3 |
| B | M72 Alone Control |  | 10 |
| C | M72 + Vehicle (DDA:DSPC liposome) | (matched [DDA] from 2 nmol) | 10 |
| D | M72 + Vehicle (DDA:DSPC liposome) | (matched [DDA] from 10 nmol) | 10 |
| E | M72 + Vehicle (DDA:DSPC liposome) | (matched [DDA] from 50 nmol) | 10 |
| F | M72 + TDB:DDA:DSPC | 2.0 | 10 |
| G | M72 + TDB:DDA:DSPC | 10.0 | 10 |
| H | M72 + TDB:DDA:DSPC | 50.0 | 10 |
| O | M72 + UM-1024:DDA:DSPC | 2.0 | 10 |
| P | M72 + UM-1024:DDA:DSPC | 10.0 | 10 |
| Q | M72 + UM-1024:DDA:DSPC | 50.0 | 10 |

Figure 5B:
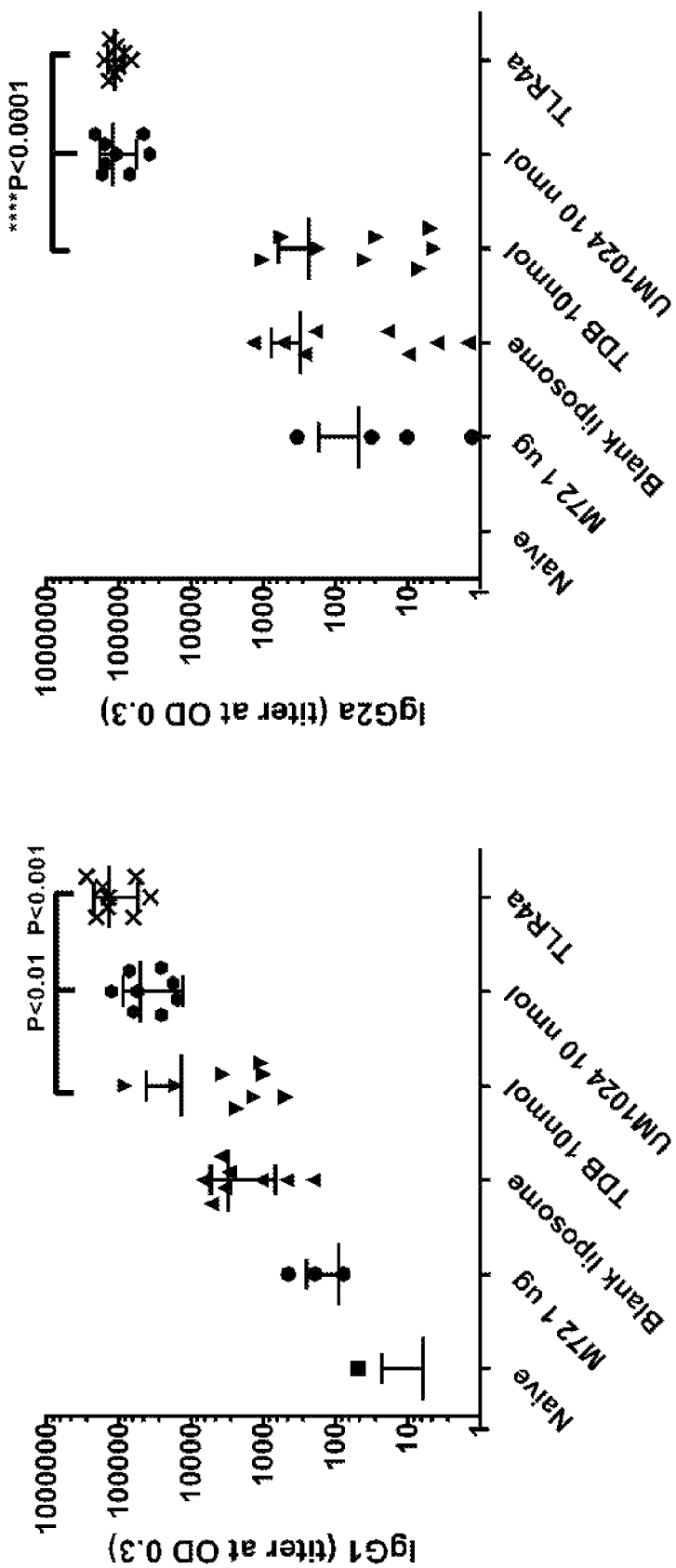

In a follow-up mouse study, animals were injected intramuscularly two times, 14 days apart, with a higher dose of M72 antigen, 1 μg, in combination with a single dose of adjuvant, 10 nmol. 14 days post-secondary injection blood was harvested, serum was isolated and levels of anti-M72 antibodies (subtypes IgG1 and IgG2a) were determined (FIG. 5B). Responses were compared to naïve mice, M72 antigen alone, and M72 antigen with blank liposomes (no CLR compound added).

Figure 6A:
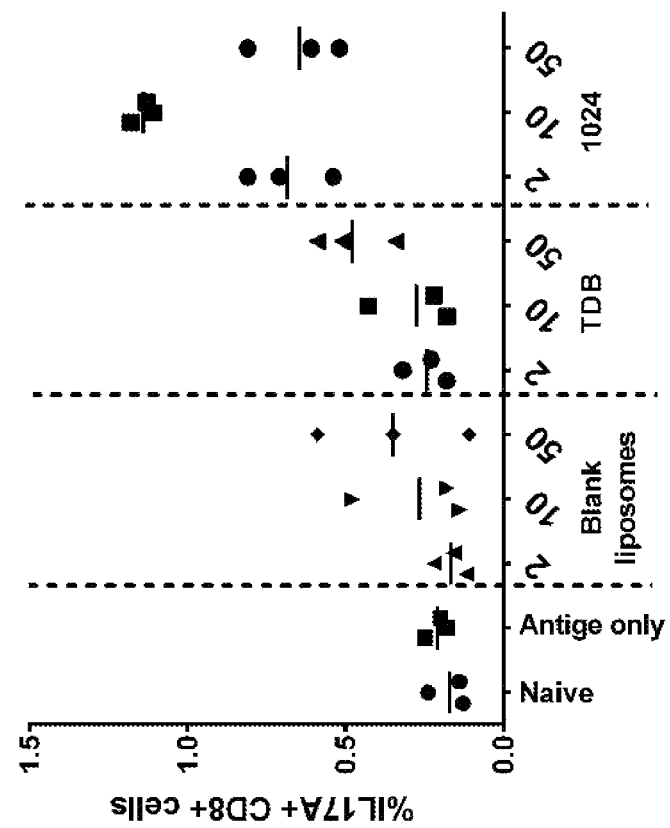
FIG. 6 shows the frequency of IL-17A (FIG. 6A), IL-5 (FIG. 6B) or IL-2 (FIG. 6C) producing CD4 and CD8 T cells in restimulated mouse spleen red blood cells following immunization with liposomal formulations containing select CLR adjuvant candidates.
Figure 6A:
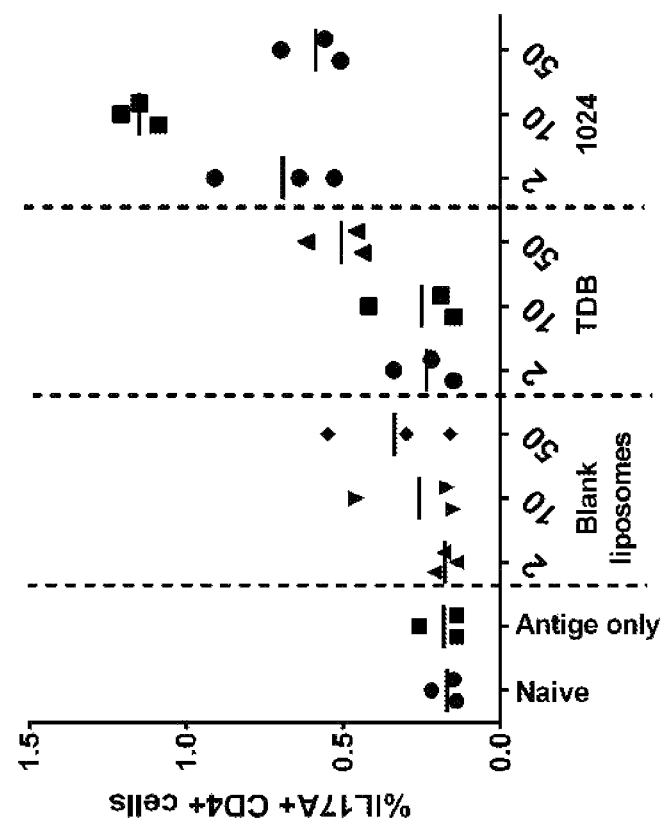

Splenocytes from harvested spleens were re-stimulated with M72 antigen to determine CD4+ and CD8+ T cell responses to the various vaccines. Responses were compared to naïve mice, M72 antigen alone, and M72 antigen with empty liposomes (no CLR compound added). UM1024, in liposomes, induced high levels of antigen-specific CD4+ and CD8+ IL17A producing cells by intracellular cytokine staining (FIG. 6A) indicating a Th17 response. Restimulation of spleen cells from mice that were vaccinated with the highest dose of TDB, induced some IL-17A. The induction of antigen-specific Th17 cells, as shown by the increased IL17A response, was important as Th17 cells provide protection against Mtb after immunization in mice.

Figure 6B:
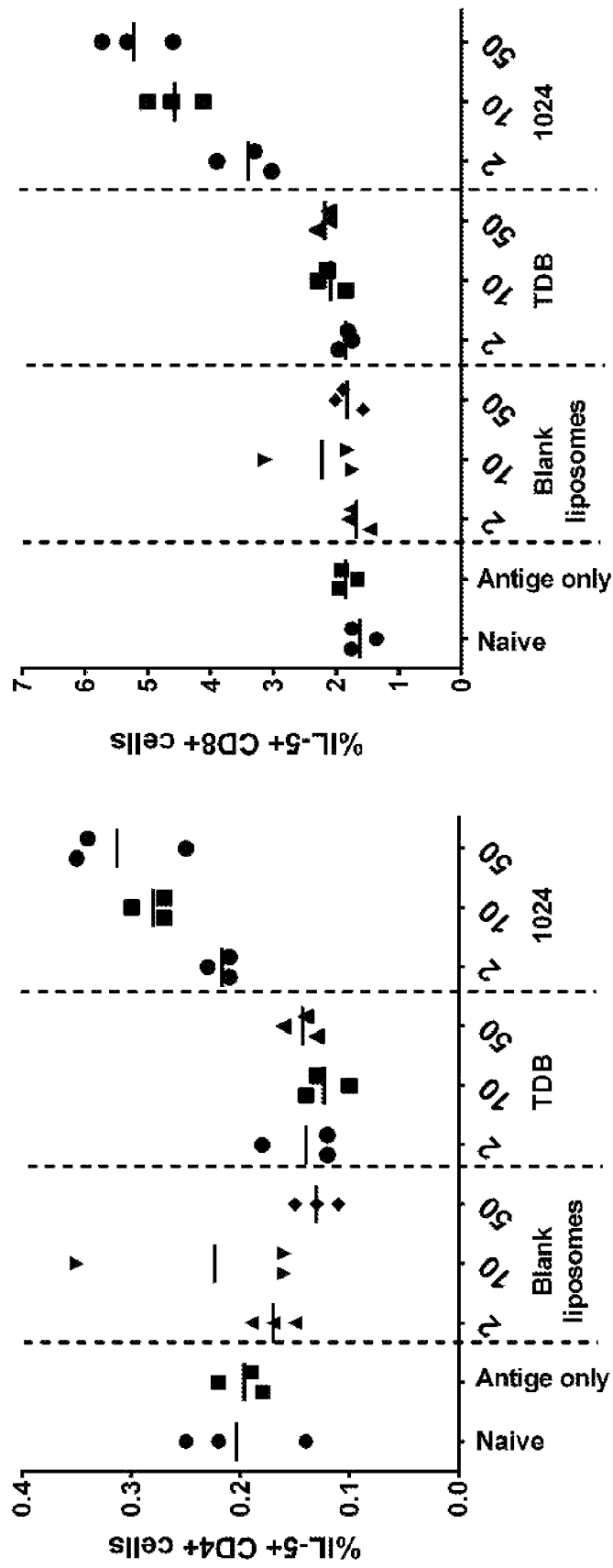

IL-5 production, indicative of a Th2 response, was seen in restimulated cells from mice that received vaccines adjuvanted with UM-1024 (FIG. 6B). However, as the Balb/c mouse strain is known to be Th2 biased, it is difficult to say whether this is reflective of further Th2 polarization in response to the UM-1024 adjuvant or is a byproduct of increased immune activation in a Th2 biased mouse strain.

Figure 6C:
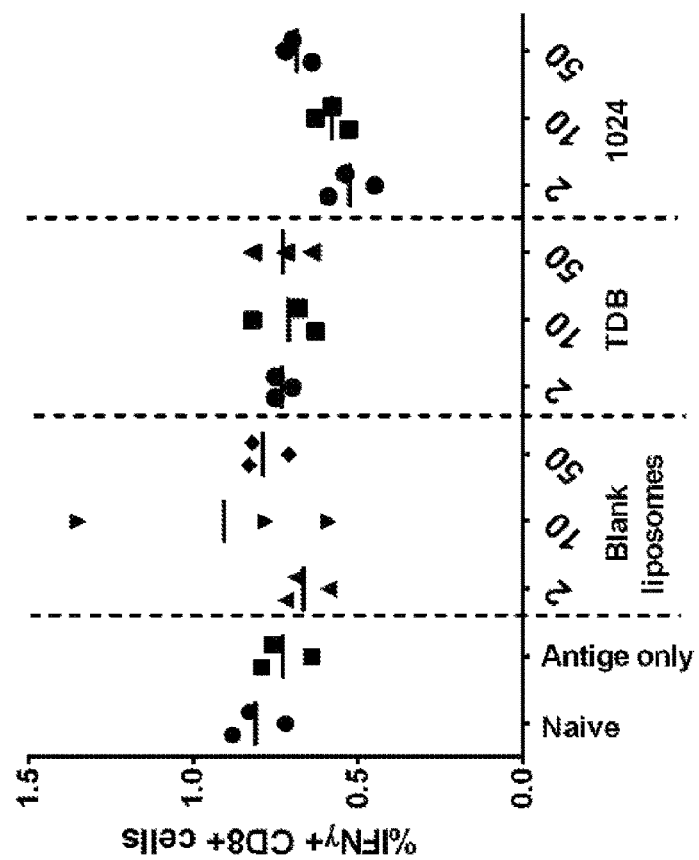
Figure 6C:
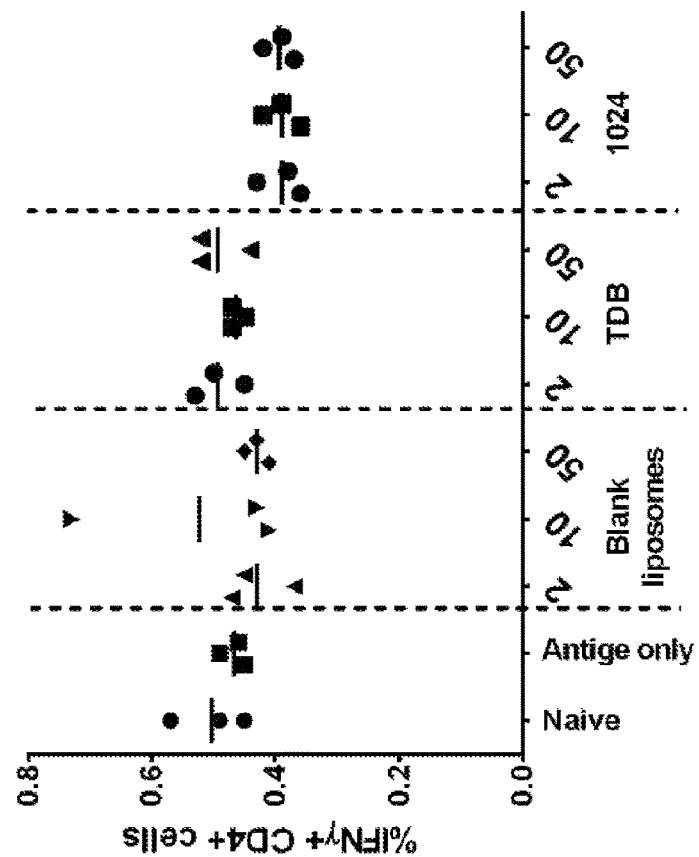

IFNγ production was not increased above levels of naïve mice in any of the vaccinated groups, suggesting that a Th1 response was not induced. TNFα production increased compared to controls in the UM-1024 adjuvanted group at the higher doses and IL-2 production was moderately increased in most adjuvanted groups, with the exception of the UM-1024 10 nmol group where IL-2 production was substantially increased compared to controls (FIG. 6C).

It is understood that the foregoing detailed description and accompanying examples are merely illustrative and are not to be taken as limitations upon the scope of the disclosure, which is defined solely by the appended claims and their equivalents.

For reasons of completeness, various aspects of the invention are set out in the following numbered clauses:

Clause 1. A compound of formula (I),

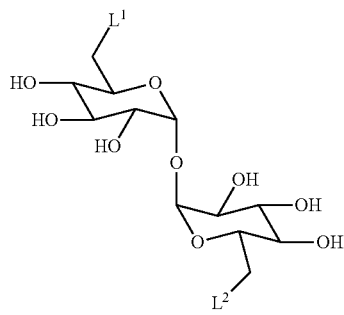

(I)

or a pharmaceutically acceptable salt thereof, wherein
$L^1$ is —OH or —X(CR$^{1a}$R$^{1a'}$)$_m$O$_p$Ar$^1$;
$L^2$ is —Y(CR$^{2a}$R$^{2a'}$)$_n$O$_q$Ar$^2$;
X and Y are each independently selected from —OC(O)—, —NR$^a$C(O)—, —NRC(S)—, —NR$^c$—, —SO$_2$NR$^c$—, —O—, and —OC(O)CH=CH—;
R$^a$, R$^b$, and R$^c$ are each independently selected from hydrogen and C$_1$-C$_4$alkyl;
m is 0, 1 or 2;
n is 0, 1 or 2;
R$^{1a}$, R$^{1a'}$, R$^{2a}$ and R$^{2a'}$, when present, are each independently selected from hydrogen and C$_1$-C$_4$ alkyl;
p is 0 or 1;
q is 0 or 1;
Ar$^1$ and Ar$^2$ are each independently selected from aryl or heteroaryl, wherein each aryl or heteroaryl may be independently substituted or unsubstituted with 1, 2, 3, 4, or 5 substituents independently selected from hydrogen, C$_1$-C$_{12}$alkyl, hydroxy, C$_1$-C$_{12}$alkoxy, halo, C$_1$-C$_4$haloalkyl, Ar$^3$, C$_1$-C$_8$alkoxy-C$_1$-C$_8$alkoxy, C$_1$-C$_8$alkoxy-C$_1$-C$_8$alkyl, hydroxy-C$_1$-C$_8$alkyl, amino, nitro, —NH—Ar$^4$, C$_1$-C$_8$alkoxy-Ar$^5$, C$_1$-C$_8$alkylsulfonyl, and C$_1$-C$_8$alkoxy-C$_1$-C$_8$alkoxy-C$_1$-C$_8$alkoxy, or the substituents, together with the atoms to which they are attached, are optionally taken together to form an aryl ring; wherein each heteroaryl may include 1, 2, 3, 4, or 5 heteroatoms selected from O, S or N;
Ar$^3$, Ar$^4$ and Ar$^5$ are each independently selected from aryl or heteroaryl independently unsubstituted or substituted with 1, 2, 3, or 4 substituents independently selected from C$_1$-C$_4$alkyl, hydroxy, C$_1$-C$_4$alkoxy, halo, C$_1$-C$_4$haloalkyl, and C$_1$-C$_4$hydroxyalkyl; and
wherein the compound is not:
6,6'-bis(2-methoxybenzoyl)-α,α-D-trehalose,
6,6'-bis(benzoylamino)-α,α-D-trehalose,
6,6'-bis(2-hydroxybenzoyl)-α,α-D-trehalose,
6,6'-bis(2-hydroxybenzoylamino)-α,α-D-trehalose,
6,6'-bis(2-methylbenzoyl)-α,α-D-trehalose,
6,6'-bis(2-methylbenzoylamino)-α,α-D-trehalose,
6,6'-bis(4-methoxybenzoyl)-α,α-D-trehalose,
6,6'-bis(4-methoxybenzoylamino)-α,α-D-trehalose,
6,6'-bis(4-hydroxybenzoyl)-α,α-D-trehalose,
6,6'-bis(4-hydroxybenzoylamino)-α,α-D-trehalose,
6,6'-bis(4-benzyloxybenzoyl)-α,α-D-trehalose,
6,6'-bis(2,3-dimethoxybenzoyl)-α,α-D-trehalose,
6,6'-bis(2,3-dimethoxybenzoylamino)-α,α-D-trehalose,
6,6'-bis(2,6-difluorobenzoyl)-α,α-D-trehalose,
6,6'-bis(2,6-difluorobenzoylamino)-α,α-D-trehalose,
6,6'-bis(2,6-dichlorobenzoyl)-α,α-D-trehalose,
6,6'-bis(2,3-dihydroxybenzoyl)-α,α-D-trehalose,
6,6'-bis(2,4-dihydroxybenzoyl)-α,α-D-trehalose,
6,6'-bis(2,4-dihydroxybenzoylamino)-α,α-D-trehalose,
6,6'-bis(2,3-dibenzyloxybenzoyl)-α,α-D-trehalose,
6,6'-bis(2-hydroxy-3-methoxybenzoyl)-α,α-D-trehalose,
6,6'-bis(2-benzyloxy-3-methoxybenzoyl)-α,α-D-trehalose,
6,6'-bis(2-methyl-6-aminobenzoyl)-α,α-D-trehalose,
6,6'-bis(3-methoxy-4-fluorobenzoyl)-α,α-D-trehalose,
6,6'-bis(3,4,5-trimethoxybenzoyl)-α,α-D-trehalose,
6,6'-bis(3,4,5-trimethoxybenzoylamino)-α,α-D-trehalose,
6,6'-bis(2,4-dihydroxy-6-methylbenzoyl)-α,α-D-trehalose,
6,6'-bis(2,4-dimethoxy-6-methylbenzoyl)-α,α-D-trehalose,
6,6'-bis(2-hydroxy-4-n-heptyloxybenzoyl)-α,α-D-trehalose,
6,6'-bis(2-hydroxy-4-n-pentyloxybenzoyl)-α,α-D-trehalose,
6,6'-bis(2-hydroxy-4-methoxybenzoyl)-α,α-D-trehalose,
6,6'-bis(4-n-pentyloxybenzoyl)-α,α-D-trehalose,
6,6'-bis(2,4-dihydroxy-6-methylbenzoyl)-α,α-D-trehalose,
6,6'-bis(cinnamoylamino)-α,α-D-trehalose,
6,6'-bis(3,4-dimethoxycinnamoylamino)-α,α-D-trehalose,
6,6'-bis(isonicotinoylamino)-α,α-D-trehalose, or
6,6'-bis(pyrazine-2-carbonylamino)-α,α-D-trehalose.

Clause 2. The compound of clause 1, or a pharmaceutical salt thereof, wherein p and q are 0.

Clause 3. The compound of clause 1 or 2, or a pharmaceutical salt thereof, wherein $L^1$ is

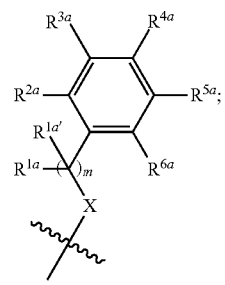

m is 0, 1 or 2;
R$^{1a}$ and R$^{1a'}$, when present, are each independently selected from hydrogen and C$_1$-C$_4$ alkyl; and
R$^{2a}$, R$^{3a}$, R$^{4a}$, R$^{5a}$, and R$^{6a}$ are each independently selected from hydrogen, C$_1$-C$_{12}$alkyl, hydroxy, $C_1$-$C_{12}$alkoxy, halo, $C_1$-$C_4$haloalkyl, aryl, $C_1$-$C_8$alkoxy-$C_1$-$C_8$alkoxy, $C_1$-$C_8$alkoxy-$C_1$-$C_8$alkyl, hydroxy-$C_1$-$C_8$alkyl, amino, nitro, arylamino, $C_1$-$C_8$alkoxy-aryl, $C_1$-$C_8$alkylsulfonyl, and $C_1$-$C_8$alkoxy-$C_1$-$C_8$alkoxy-$C_1$-$C_8$alkoxy, or together with the atoms to which they are attached, are optionally taken together to form an aryl ring.

Clause 4. The compound of any of clauses 1-3, or a pharmaceutical salt thereof, wherein $R^{1a'}$, when present, is hydrogen.

Clause 5. The compound of any of clauses 3-4, or a pharmaceutical salt thereof, wherein $R^{2a}$, $R^{3a}$, $R^{4a}$, $R^{5a}$, and $R^{6a}$ are each independently selected from hydrogen, $C_1$-$C_8$alkyl, hydroxy, $C_1$-$C_8$alkoxy, halo, $C_1$-$C_4$haloalkyl, aryl, $C_1$-$C_8$alkoxy-$C_1$-$C_8$alkoxy, $C_1$-$C_8$alkoxy-$C_1$-$C_8$alkyl, and hydroxy-$C_1$-$C_8$alkyl;

wherein $R^{3a}$ and $R^{4a}$, together with the carbon atoms to which they are attached, are optionally taken together to form an aryl ring.

Clause 6. The compound of any of clauses 1-5, or a pharmaceutical salt thereof, wherein $L^2$ is

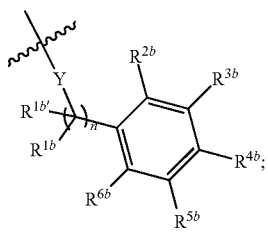

n is 0, 1 or 2;

$R^{1b}$ and $R^{1b'}$, when present, are each independently selected from hydrogen and $C_1$-$C_4$ alkyl; and $R^{2b}$, $R^{3b}$, $R^{4b}$, $R^{5b}$, and $R^{6b}$ are each independently selected from hydrogen, $C_1$-$C_{12}$alkyl, hydroxy, $C_1$-$C_{12}$alkoxy, halo, $C_1$-$C_4$haloalkyl, aryl, $C_1$-$C_8$alkoxy-$C_1$-$C_8$alkoxy, $C_1$-$C_8$alkoxy-$C_1$-$C_8$alkyl, hydroxy-$C_1$-$C_8$alkyl, amino, nitro, arylamino, $C_1$-$C_8$alkoxy-aryl, $C_1$-$C_8$alkylsulfonyl, and $C_1$-$C_8$alkoxy-$C_1$-$C_8$alkoxy-$C_1$-$C_8$alkoxy, or together with the atoms to which they are attached, are optionally taken together to form an aryl ring.

Clause 7. The compound of any of clauses 1-6, or a pharmaceutical salt thereof, wherein $R^{1b'}$, when present, is hydrogen.

Clause 8. The compound of any of clauses 1-7, or a pharmaceutical salt thereof, wherein $R^{2b}$, $R^{3b}$, $R^{4b}$, $R^{5b}$, and $R^{6b}$ are each independently selected from hydrogen, $C_1$-$C_8$alkyl, hydroxy, $C_1$-$C_8$alkoxy, halo, $C_1$-$C_4$haloalkyl, aryl, $C_1$-$C_8$alkoxy-$C_1$-$C_8$alkoxy, $C_1$-$C_8$alkoxy-$C_1$-$C_8$alkyl, and hydroxy-$C_1$-$C_8$alkyl;

wherein $R^{3b}$ and $R^{4b}$, together with the carbon atoms to which they are attached, are optionally taken together to form an aryl ring.

Clause 9. The compound of clause 1, wherein the compound is a compound of formula (Ia):

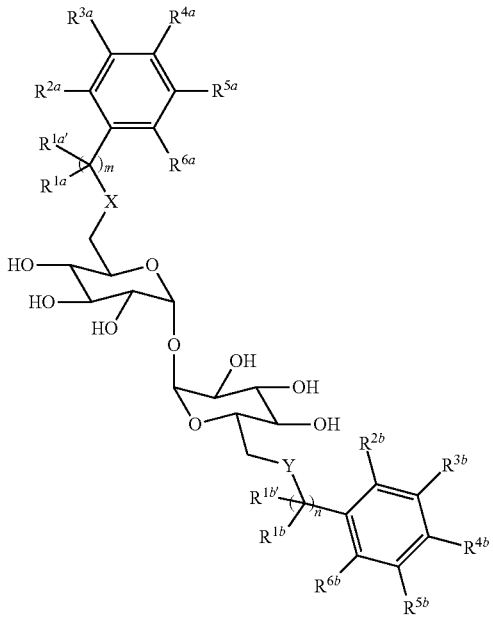

(Ia)

or a pharmaceutically acceptable salt thereof, wherein

X and Y are each independently selected from —OC(O)— and —NR$^a$C(O)—;

$R^a$ is independently selected from hydrogen and $C_1$-$C_4$ alkyl;

m is 0, 1 or 2;

n is 0, 1 or 2;

$R^{1a}$, $R^{1a'}$, $R^{1b}$ and $R^{1b'}$ when present, are each hydrogen; and $R^{2a}$, $R^{2b}$, $R^{3a}$, $R^{3b}$, $R^{4a}$, $R^{4b}$, $R^{5a}$, $R^{5b}$, $R^{6a}$, and $R^{6b}$ are each independently selected from hydrogen, $C_1$-$C_8$alkyl, and hydroxy.

Clause 10. The compound of clause 9, or a pharmaceutically acceptable salt thereof, wherein at least one of $R^{2a}$, $R^{3a}$, $R^{4a}$, $R^{5a}$, and $R^{6a}$ is $C_1$-$C_8$alkyl and at least one of $R^{2b}$, $R^{3b}$, $R^{4b}$, $R^{5b}$, and $R^{6b}$ is $C_1$-$C_8$alkyl.

Clause 11. The compound of clause 10, or a pharmaceutically acceptable salt thereof, wherein each of $R^{3a}$, $R^{3b}$, $R^{5a}$, and $R^{5b}$ are $C_1$-$C_8$alkyl.

Clause 12. The compound of clause 11, or a pharmaceutically acceptable salt thereof, wherein the $C_1$-$C_8$alkyl is isopropyl, tert-butyl, methyl or ethyl.

Clause 13. The compound of clause 12, or a pharmaceutically acceptable salt thereof, wherein the $C_1$-$C_8$alkyl is tert-butyl.

Clause 14. The compound of clause 11, or a pharmaceutically acceptable salt thereof, wherein $R^{2a}$, $R^{2b}$, $R^{4a}$, $R^{4b}$, $R^{6a}$, $R^{6b}$ are each independently hydroxy or hydrogen.

Clause 15. The compound of clause 14, or a pharmaceutically acceptable salt thereof, $R^{2a}$ and $R^{2b}$ are each hydroxy.

Clause 16. The compound of clause 14, or a pharmaceutically acceptable salt thereof, wherein $R^{4a}$ and $R^{4b}$ are each hydroxy.

Clause 17. The compound of clause 10, or a pharmaceutically acceptable salt thereof, wherein $R^{2a}$, $R^{2b}$, $R^{6a}$, and $R^{6b}$ are methyl.

Clause 18. The compound of clause 17, or a pharmaceutically acceptable salt thereof, wherein $R^{3a}$, $R^{3b}$, $R^{4a}$, $R^{4b}$, $R^{5a}$, and $R^{5b}$ are each independently hydrogen or $C_1$-$C_8$alkyl.

Clause 19. The compound of clause 18, or a pharmaceutically acceptable salt thereof, wherein the $C_1$-$C_5$ alkyl is methyl or tert-butyl.

Clause 20. The compound of any one of clauses 9-19, or a pharmaceutically acceptable salt thereof, wherein m and n are 0.

Clause 21. The compound of clause 1, wherein the compound is a compound of formula (Ib):

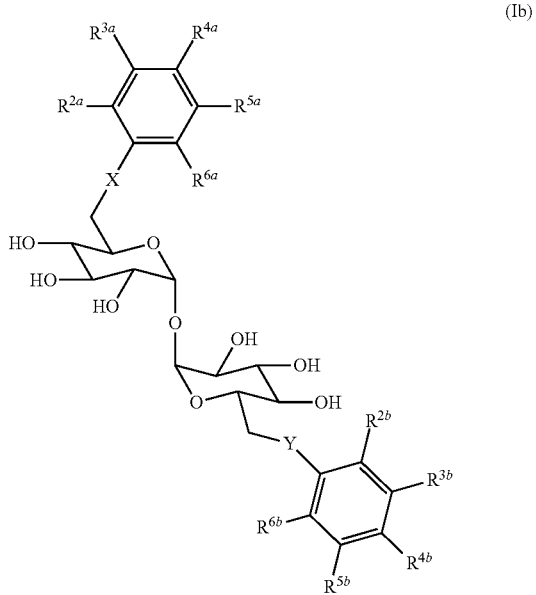

(Ib)

or a pharmaceutically acceptable salt thereof, wherein
X and Y are each independently selected from —OC(O)— and —NR$^a$C(O)—;
R$^a$ is independently selected from hydrogen and $C_1$-$C_4$alkyl;
$R^{2a}$, $R^{2b}$, $R^{3a}$, $R^{3b}$, $R^{4a}$, $R^{4b}$, $R^{5a}$, $R^{5b}$, $R^{6a}$, and $R^{6b}$ are each independently selected from hydrogen, $C_1$-$C_{12}$alkyl, hydroxy, $C_1$-$C_{12}$alkoxy, $C_1$-$C_4$haloalkyl, Ar$^3$ and, —NH—Ar$^4$ or together with the atoms to which they are attached, are optionally taken together to form an aryl ring;
Ar$^3$, Ar$^4$ and Ar$^5$ are each independently selected from aryl or heteroaryl independently unsubstituted or substituted with 1, 2, 3, or 4 substituents independently selected from $C_1$-$C_4$ alkyl, hydroxy, $C_1$-$C_4$alkoxy, halo, $C_1$-$C_4$haloalkyl, and $C_1$-$C_4$hydroxyalkyl.

Clause 22. The compound of clause 21, or a pharmaceutically acceptable salt thereof, wherein $R^{3a}$, $R^{3b}$, $R^{5a}$, and $R^{5b}$ are each $C_1$-$C_8$alkoxy.

Clause 23. The compound of clause 22, or a pharmaceutically acceptable salt thereof, wherein $R^{2a}$, $R^{2b}$, $R^{4a}$, $R^{4b}$, $R^{6a}$, and $R^{6b}$ are each hydrogen.

Clause 24. The compound of clause 22, or a pharmaceutically acceptable salt thereof, wherein $R^{4a}$ and $R^{4b}$ are each $C_1$-$C_5$alkoxy.

Clause 25. The compound of clause 24, or a pharmaceutically acceptable salt thereof, wherein $R^{3a}$, $R^{3b}$, $R^{4a}$, $R^{4b}$, $R^{5a}$, and $R^{5b}$ are each ethoxy.

Clause 26. The compound of claim use 24, or a pharmaceutically acceptable salt thereof, wherein $R^{2a}$, $R^{2b}$, $R^{6a}$ and $R^{6b}$ are each hydrogen.

Clause 27. The compound of clause 21, or a pharmaceutically acceptable salt thereof, wherein $R^{2a}$ and $R^{2b}$ are each $C_1$-$C_5$alkoxy or hydroxy.

Clause 28. The compound of clause 27, or a pharmaceutically acceptable salt thereof, wherein at least one of $R^{3a}$, $R^{4a}$, $R^{5a}$, and $R^{6a}$ is $C_1$-$C_8$alkyl and at least one of $R^{3b}$, $R^{4b}$, $R^{5b}$, and $R^{6b}$ is $C_1$-$C_8$alkyl.

Clause 29. The compound of clause 28, or a pharmaceutically acceptable salt thereof, wherein the $C_1$-$C_8$alkyl is tert-butyl.

Clause 30. The compound of clause 21, or a pharmaceutically acceptable salt thereof, wherein at least one of $R^{2a}$, $R^{3a}$, $R^{4a}$, $R^{5a}$, and $R^{6a}$ is $C_1$-$C_4$haloalkyl and at least one of $R^{2b}$, $R^{3b}$, $R^{4b}$, $R^{5b}$, and $R^{6b}$ is $C_1$-$C_4$haloalkyl.

Clause 31. The compound of clause 30, or a pharmaceutically acceptable salt thereof, wherein $R^{2a}$ and $R^{2b}$ are each $C_1$-$C_4$haloalkyl.

Clause 32. The compound of clause 31, or a pharmaceutically acceptable salt thereof, wherein $R^{3a}$, $R^{3b}$, $R^{5a}$, and $R^{5b}$ are each hydrogen.

Clause 33. The compound of clause 32, or a pharmaceutically acceptable salt thereof, wherein $R^{6a}$ and $R^{6b}$ are each hydrogen or $C_1$-$C_4$haloalkyl.

Clause 34. The compound of clause 33, or a pharmaceutically acceptable salt thereof, wherein $R^{4a}$ and $R^{4b}$ are each hydrogen or $C_1$-$C_4$alkoxy.

Clause 35. The compound of clause 34, or a pharmaceutically acceptable salt thereof, wherein the $C_1$-$C_4$alkoxy is methoxy.

Clause 36. The compound of clause 30, or a pharmaceutically acceptable salt thereof, wherein $R^{3a}$ and $R^{3b}$ are each $C_1$-$C_4$haloalkyl.

Clause 37. The compound of clause 36, or a pharmaceutically acceptable salt thereof, wherein $R^{5a}$ and $R^{5b}$ are each hydrogen or $C_1$-$C_4$haloalkyl.

Clause 38. The compound of clause 37, or a pharmaceutically acceptable salt thereof, wherein $R^{2a}$, and $R^{2b}$ are each hydrogen or hydroxy.

Clause 39. The compound of clause 38, or a pharmaceutically acceptable salt thereof, wherein $R^{4a}$, $R^{4b}$, $R^{6a}$, and $R^{6b}$ are each hydrogen.

Clause 40. The compound of clause 31, or a pharmaceutically acceptable salt thereof, wherein $R^{5a}$ and $R^{5b}$ are each $C_1$-$C_4$alkoxy.

Clause 41. The compound of clause 40, or a pharmaceutically acceptable salt thereof, wherein the $C_1$-$C_4$alkoxy are methoxy.

Clause 42. The compound of clause 41, or a pharmaceutically acceptable salt thereof, wherein $R^{3a}$, $R^{3b}$, $R^{4a}$, $R^{4b}$, $R^{6a}$, and $R^{6b}$ are hydrogen.

Clause 43. The compound of clauses 30-42, or a pharmaceutically acceptable salt thereof, wherein the $C_1$-$C_4$haloalkyl is trifluoromethyl.

Clause 44. The compound of clause 21, or a pharmaceutically acceptable salt thereof, wherein
$R^{6a}$ and $R^{6b}$ are each hydrogen;
$R^{2a}$, $R^{2b}$, $R^{3a}$, $R^{3b}$, $R^{4a}$, $R^{4b}$, $R^{5a}$, and $R^{5b}$ are each independently selected from hydrogen, hydroxy, Ar$^3$ and, —NH—Ar$^4$, wherein at least one of $R^{2a}$, $R^{3a}$, $R^{4a}$, and $R^{5a}$ is Ar$^3$ or —NH—Ar$^4$ and at least one of $R^{2b}$, $R^{3b}$, $R^{4b}$, and $R^{5b}$ is Ar$^3$ or —NH—Ar$^4$; and
Ar$^3$ and Ar$^4$ are each independently selected from aryl or heteroaryl independently unsubstituted or substituted with 1, 2, 3, or 4 substituents independently selected from $C_1$-$C_4$ alkyl, hydroxy, $C_1$-$C_4$alkoxy, halo, $C_1$-$C_4$haloalkyl, and $C_1$-$C_4$hydroxyalkyl.

Clause 45. The compound of clause 44, or a pharmaceutically acceptable salt thereof, wherein Ar$^3$ and Ar$^4$ are phenyl unsubstituted or substituted with 1, 2, or 3 substituents independently selected from the group consisting of hydroxy, alkoxy, $C_1$-$C_4$alkyl, and hydroxy-$C_1$-$C_4$alkyl.

Clause 46. The compound of clause 45, or a pharmaceutically acceptable salt thereof, wherein the phenyl is substituted with one substituent selected from methyl, hydroxy, and hydroxymethyl.

Clause 47. The compound of clauses 44-46, or a pharmaceutically acceptable salt thereof, wherein at least one of $R^{2a}$, $R^{3a}$, $R^{4a}$, and $R^{5a}$ is hydroxy and at least one of $R^{2b}$, $R^{3b}$, $R^{4b}$, and $R^{5b}$ is hydroxy.

Clause 48. The compound of clause 21, or a pharmaceutically acceptable salt thereof, wherein at least two of $R^{3a}$, $R^{4a}$, and $R^{5a}$ are $C_5$-$C_{12}$alkoxy, at least two of $R^{3b}$, $R^{4b}$, and $R^{5b}$ are $C_5$-$C_{12}$alkoxy, and $R^{2a}$, $R^{2b}$, $R^{6a}$, and $R^{6b}$ are each hydrogen.

Clause 49. The compound of clause 48, or a pharmaceutically acceptable salt thereof, wherein $R^{3a}$, $R^{3b}$, $R^{5a}$, and $R^{5b}$ are each $C_5$-$C_2$alkoxy.

Clause 50. The compound of clause 49, or a pharmaceutically acceptable salt thereof, wherein $R^{4a}$ and $R^{4b}$ are each $C_5$-$C_{12}$alkoxy.

Clause 51. A compound selected from the group consisting of
6,6'-bis(3,5-dimethoxybenzoyl)-α,α-D-trehalose,
6,6'-bis(2-hydroxy-3,5-di-tert-butylbenzoyl)-α,α-D-trehalose,
6,6'-bis(3,5-dipentyloxybenzoyl)-α,α-D-trehalose,
6,6'-bis(3,4,5-triethoxybenzoyl)-α,α-D-trehalose,
6,6'-bis(2-hydroxy-3,5-di-tert-butylbenzoylamino)-α,α-D-trehalose,
6,6'-bis(2,6-hydroxy-3,5-di-tert-butylbenzoylamino)-α,α-D-trehalose,
or a pharmaceutically acceptable salt thereof.

Clause 52. A compound that is 6,6-bis(3,5-dimethoxybenzoyl)-α,α-D-trehalose, or a pharmaceutically acceptable salt thereof.

Clause 53. A compound that is 6,6-bis(2-hydroxy-3,5-di-tert-butylbenzoyl)-α,α-D-trehalose, or a pharmaceutically acceptable salt thereof.

Clause 54. An adjuvant composition comprising an effective amount of a compound of any one of clauses 1-53, or a pharmaceutically acceptable salt thereof.

Clause 55. A method for inducing an enhanced immune response in a subject, comprising administering to the subject the adjuvant composition of clause 54.

Clause 56. A vaccine composition comprising: (a) an antigen; and (b) an adjuvant composition comprising an effective amount of a compound of any one of clauses 1-53, or a pharmaceutically acceptable salt thereof.

Clause 57. A method for inducing or enhancing immunogenicity of an antigen in a subject, comprising administering to the subject a vaccine composition comprising the antigen and an adjuvant composition comprising an effective amount of a compound of any one of clauses 1-53, or a pharmaceutically acceptable salt thereof.

Clause 58. An immunomodulatory composition comprising an effective amount of a compound of any one of clauses 1-53, or a pharmaceutically acceptable salt thereof.

Clause 59. A method of modulating an immune response in a subject, comprising administering to the subject the immunomodulatory composition of clause 58.

Clause 60. The method of clause 59, wherein the immunomodulatory composition is administered as a monotherapy.

Clause 61. The method of clause 59 or clause 60, wherein the immune response in the subject is increased.

Clause 62. The method of any one of clauses 59-61, wherein the subject is suffering from cancer, an autoimmune disorder, or an infectious disease.

Clause 63. A compound of formula (II),

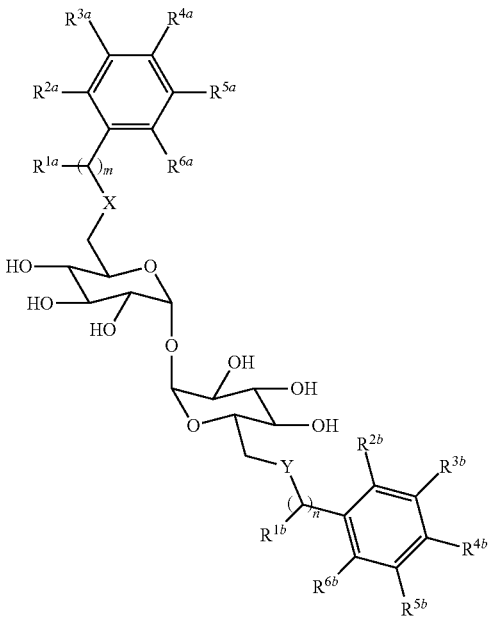

(II)

or a pharmaceutically acceptable salt thereof, wherein
m is 0, 1 or 2;
n is 0, 1 or 2;
X and Y are each independently selected from —C(O)O—, —C(O)NR$^a$—, —C(S)NR$^b$—, —NR$^c$—, and —O—;
R$^a$, R$^b$, and R$^c$ are each independently selected from hydrogen and $C_1$-$C_4$alkyl;
R$^{1a}$ and R$^{1b}$, when present, are each independently selected from hydrogen and $C_1$-$C_4$alkyl;
$R^{2a}$, $R^{2b}$, $R^{3a}$, $R^{3b}$, $R^{4a}$, $R^{4b}$, $R^{5a}$, $R^{5b}$, $R^{6a}$, and $R^{6b}$ are each independently selected from hydrogen, $C_1$-$C_8$alkyl, hydroxy, $C_1$-$C_8$alkoxy, halo, $C_1$-$C_4$haloalkyl, aryl, $C_1$-$C_8$alkoxy-$C_1$-$C_8$alkoxy, $C_1$-$C_8$alkoxy-$C_1$-$C_8$alkyl, and hydroxy-$C_1$-$C_8$alkyl;
wherein $R^{3a}$ and $R^{4a}$, together with the carbon atoms to which they are attached, are optionally taken together to form an aryl ring;
wherein $R^{3b}$ and $R^{4b}$, together with the carbon atoms to which they are attached, are optionally taken together to form an aryl ring;
wherein each aryl is independently unsubstituted or substituted with 1, 2, or 3 substituents independently selected from $C_1$-$C_4$alkyl, hydroxy, $C_1$-$C_4$alkoxy, halo, $C_1$-$C_4$haloalkyl, and $C_1$-$C_4$hydroxyalkyl; and
wherein the compound is not:
6,6'-bis(2-methoxybenzoyl)-α,α-D-trehalose,
6,6'-bis(2-hydroxybenzoyl)-α,α-D-trehalose,
6,6'-bis(2-methylbenzoyl)-α,α-D-trehalose,
6,6'-bis(4-methoxybenzoyl)-α,α-D-trehalose,
6,6'-bis(4-hydroxybenzoyl)-α,α-D-trehalose,
6,6'-bis(4-benzyloxybenzoyl)-α,α-D-trehalose,
6,6'-bis(2,3-dimethoxybenzoyl)-α,α-D-trehalose,
6,6'-bis(2,6-difluorobenzoyl)-α,α-D-trehalose,
6,6'-bis(2,6-dichlorobenzoyl)-α,α-D-trehalose,
6,6'-bis(2,3-dihydroxybenzoyl)-α,α-D-trehalose,
6,6'-bis(2,4-dihydroxybenzoyl)-α,α-D-trehalose,
6,6'-bis(2,3-dibenzyloxybenzoyl)-α,α-D-trehalose, 6,6'-bis(2-hydroxy-3-methoxybenzoyl)-α,α-D-trehalose,
6,6'-bis(2-benzyloxy-3-methoxybenzoyl)-α,α-D-trehalose,
6,6'-bis(2-methyl-6-aminobenzoyl)-α,α-D-trehalose,
6,6'-bis(3-methoxy-4-fluorobenzoyl)-α,α-D-trehalose,
6,6'-bis(3,4,5-trimethoxybenzoyl)-α,α-D-trehalose,
6,6'-bis(2,4-dihydroxy-6-methylbenzoyl)-α,α-D-trehalose,
6,6'-bis(2,4-dimethoxy-6-methylbenzoyl)-α,α-D-trehalose,
6,6'-bis(2-hydroxy-4-n-heptyloxybenzoyl)-α,α-D-trehalose,
6,6'-bis(2-hydroxy-4-n-pentyloxybenzoyl)-α,α-D-trehalose,
6,6'-bis(2-hydroxy-4-methoxybenzoyl)-α,α-D-trehalose,
6,6'-bis(4-n-pentyloxybenzoyl)-α,α-D-trehalose, or
6,6'-bis(2,4-dihydroxy-6-methylbenzoyl)-α,α-D-trehalose.

Clause 64. The compound of clause 63, wherein $R^{3a}$, $R^{3b}$, $R^{5a}$, and $R^{5b}$ are each $C_2$-$C_8$alkoxy.

Clause 65. The compound of clause 64, wherein the $C_2$-$C_8$alkoxy is ethoxy.

Clause 66. The compound of clause 63 or clause 64, wherein $R^{2a}$, $R^{2b}$, $R^{4a}$, $R^{4b}$, $R^{6a}$, and $R^{6b}$ are hydrogen.

Clause 67. The compound of clause 63, wherein at least one of $R^{2a}$, $R^{2b}$, $R^{3a}$, $R^{3b}$, $R^{4a}$, $R^{4b}$, $R^{5a}$, $R^{5b}$, and $R^{6a}$, and $R^{6b}$ is tert-butyl.

Clause 68. The compound of clause 67, wherein $R^{3a}$, $R^{3b}$, $R^{5a}$, and $R^{5b}$ are each tert-butyl.

Clause 69. The compound of clause 68, wherein $R^{2a}$ and $R^{2b}$ are each hydroxy.

Clause 70. The compound of any one of clauses 67-69, wherein $R^{4a}$, $R^{4b}$, $R^{6a}$, and $R^{6b}$ are each hydrogen.

Clause 71. The compound of any one of clauses 63-70, wherein m is 0 and n is 0.

Clause 72. The compound of any one of clauses 63-71, wherein X and Y are each —C(O)O—.

Clause 73. A compound of formula (IIa):

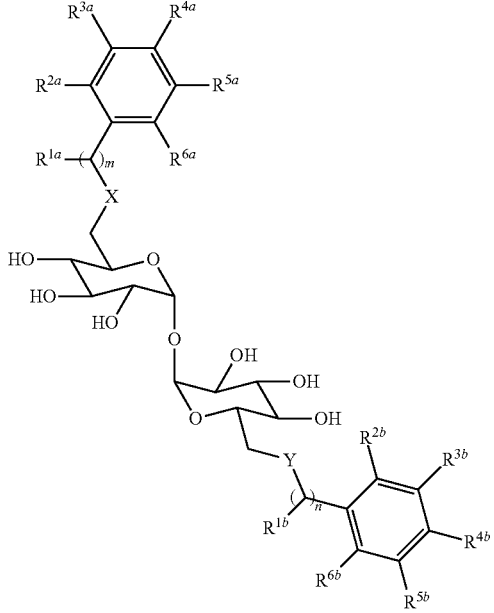

(IIa)

or a pharmaceutically acceptable salt thereof, wherein:
m is 0, 1 or 2;
n is 0, 1 or 2;
X and Y are each independently selected from —C(O)O—, —C(O)NR$^a$—, —C(S)NR$^b$—, —NR$^c$—, and —O—;
R$^a$, R$^b$, and R$^c$ are each independently selected from hydrogen and $C_1$-$C_4$alkyl;

R$^{1a}$ and R$^{1b}$, when present, are each independently selected from hydrogen and $C_1$-$C_4$alkyl;
$R^{2a}$, $R^{2b}$, $R^{6a}$ and $R^{6b}$ are each independently selected from hydrogen, $C_1$-$C_4$alkyl, hydroxy, and $C_1$-$C_4$-alkoxy;
$R^{4a}$ and $R^{4b}$ are hydrogen; and
$R^{3a}$, $R^{3b}$, $R^{5a}$, and $R^{5b}$ are each independently selected from $C_1$-$C_8$alkyl, hydroxy, $C_1$-$C_8$alkoxy, halo, $C_1$-$C_8$haloalkyl, aryl, $C_1$-$C_8$alkoxy-$C_1$-$C_8$alkoxy, $C_1$-$C_8$alkoxy-$C_1$-$C_8$alkyl, hydroxy-$C_1$-$C_8$alkyl;
wherein each aryl is independently unsubstituted or substituted with 1, 2, or 3 substituents independently selected from $C_1$-$C_4$alkyl, hydroxy, $C_1$-$C_4$alkoxy, halo, $C_1$-$C_4$haloalkyl, and $C_1$-$C_4$hydroxyalkyl.

Clause 74. The compound of clause 73, wherein
each n is 0; $R^{2a}$ and $R^{2b}$ are each independently hydrogen or hydroxy; $R^{3a}$ and $R^{3b}$ are each independently selected from $C_1$-$C_8$alkyl, hydroxy, $C_2$-$C_8$alkoxy, $C_1$-$C_4$alkoxy-$C_1$-$C_4$alkoxy, and $C_1$-$C_4$haloalkyl; $R^{5a}$ and $R^{5b}$ are each independently selected from $C_1$-$C_8$alkyl, hydroxy, $C_2$-$C_8$alkoxy, $C_1$-$C_4$alkoxy-$C_1$-$C_4$alkoxy, and $C_1$-$C_4$haloalkyl; and $R^{6a}$ and $R^{6b}$ are each independently hydrogen or hydroxy.

Clause 75. The compound of clause 73 or clause 74, wherein $R^{3a}$, $R^{3b}$, $R^{5a}$, and $R^{5b}$ are each $C_2$-$C_8$alkoxy.

Clause 76. The compound of clause 75, wherein the $C_2$-$C_8$alkoxy is ethoxy.

Clause 77. The compound of clause 75 or clause 76, wherein $R^{2a}$, $R^{2b}$, $R^{6a}$, and $R^{6b}$ are each hydrogen.

Clause 78. The compound of clause 73 or clause 74, wherein at least one of $R^{3a}$, $R^{3b}$, $R^{5a}$, and $R^{5b}$ is tert-butyl.

Clause 79. The compound of clause 78, wherein $R^{3a}$, $R^{3b}$, $R^{5a}$, and $R^{5b}$ are each tert-butyl.

Clause 80. The compound of clause 78 or clause 79, wherein $R^{2a}$ and $R^{2b}$ are each hydroxy.

Clause 81. The compound of any one of clauses 78-80, wherein $R^{6a}$ and $R^{6b}$ are each hydrogen.

Clause 82. The compound of any one of clauses 73-83, wherein m is 0 and n is 0.

Clause 83. The compound of any one of clauses 73-82, wherein X and Y are each —C(O)O—.

Clause 84. A compound of formula (IIb):

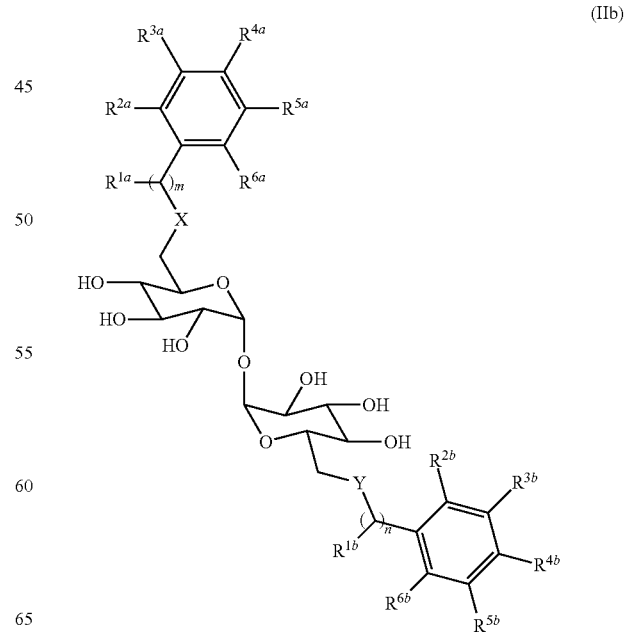

(IIb)

or a pharmaceutically acceptable salt thereof, wherein:
m is 0, 1 or 2;
n is 0, 1 or 2;
X and Y are each independently selected from —C(O)O—, —C(O)NR$^a$—, —C(S)NR$^b$—, —NR$^c$—, and —O—;
R$^a$, R$^b$, and R$^c$ are each independently selected from hydrogen and $C_1$-$C_4$alkyl;
R$^{1a}$ and R$^{1b}$, when present, are each independently selected from hydrogen and $C_1$-$C_4$alkyl;
R$^{6a}$ and R$^{6b}$ are each hydrogen; and
R$^{2a}$, R$^{2b}$, R$^{3a}$, R$^{3b}$, R$^{4a}$, R$^{4b}$, R$^{5a}$, and R$^{5b}$ are each independently selected from hydrogen, hydroxy, and aryl, wherein at least one of R$^{2a}$, R$^{2b}$, R$^{3a}$, R$^{3b}$, R$^{4a}$, R$^{4b}$, R$^{5a}$, and R$^{5b}$ is aryl; or
wherein R$^{3a}$ and R$^{4a}$, together with the carbon atoms to which they are attached, are optionally taken together to form an aryl ring; or
wherein R$^{3b}$ and R$^{4b}$, together with the carbon atoms to which they are attached, are optionally taken together to form an aryl ring;
wherein each aryl is independently unsubstituted or substituted with 1, 2, or 3 substituents independently selected from $C_1$-$C_4$alkyl, hydroxy, $C_1$-$C_4$alkoxy, halo, $C_1$-$C_4$haloalkyl, and $C_1$-$C_4$hydroxyalkyl.

Clause 85. The compound of clause 84, wherein m is 0 and n is 0.

Clause 86. The compound of clause 84 or clause 85, wherein one of R$^{2a}$, R$^{2b}$, R$^{3a}$, R$^{3b}$, R$^{4a}$, R$^{4b}$, R$^{5a}$, and R$^{5b}$ is phenyl, and the phenyl is unsubstituted or substituted with 1, 2, or 3 substituents independently selected from the group consisting of hydroxy, alkoxy, $C_1$-$C_4$alkyl, and hydroxy-$C_1$-$C_4$alkyl.

Clause 87. The compound of clause 86, the phenyl is substituted with one substituent selected from methyl, hydroxy, and hydroxymethyl.

Clause 88. The compound of any one of clauses 84-87, wherein X and Y are each —C(O)O—.

Clause 89. A compound of formula (IIc):

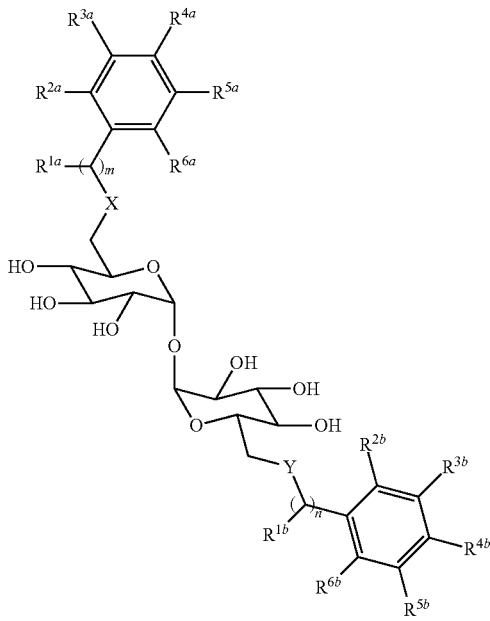

(IIc)

or a pharmaceutically acceptable salt thereof, wherein:
m is 0, 1 or 2;
n is 0, 1 or 2;
X and Y are each independently selected from —C(O)O—, —C(O)NR$^a$—, —C(S)NR$^b$—, —NR$^c$—, and —O—;
R$^a$, R$^b$, and R$^c$ are each independently selected from hydrogen and $C_1$-$C_4$alkyl;
R$^{2a}$, R$^{2b}$, R$^{3a}$, R$^{3b}$, R$^{4a}$, R$^{4b}$, R$^{5a}$, R$^{5b}$, R$^{6a}$, and R$^{6b}$ are each independently selected from hydrogen, hydroxy, and $C_1$-$C_4$alkoxy, and $C_1$-$C_4$haloalkyl, wherein at least one of R$^{2a}$, R$^{2b}$, R$^{3a}$, R$^{3b}$, R$^{4a}$, R$^{4b}$, R$^{5a}$, R$^{5b}$, R$^{6a}$, and R$^{6b}$ is $C_1$-$C_4$haloalkyl.

Clause 90. The compound of clause 89, wherein
m is 0;
n is 0;
R$^{2a}$ and R$^{2b}$ are each independently selected from hydrogen, hydroxy, $C_1$-$C_4$alkoxy, and $C_1$-$C_4$haloalkyl;
R$^{3a}$, R$^{3b}$, R$^{5a}$, R$^{5b}$, R$^{6a}$ and R$^{6b}$ are each independently selected from hydrogen and $C_1$-$C_4$haloalkyl; and
R$^{4a}$ and R$^{4b}$ are each independently selected from hydrogen, hydroxy, and $C_1$-$C_4$haloalkyl.

Clause 91. The compound of clause 89 or clause 90, wherein at least one of R$^{2a}$, R$^{2b}$, R$^{3a}$, R$^{3b}$, R$^{4a}$, R$^{4b}$, R$^{5a}$, R$^{5b}$, R$^{6a}$, and R$^{6b}$ is trifluoromethyl.

Clause 92. The compound of any one of clauses 89-91, wherein X and Y are each —C(O)O—.

Clause 93. A compound of formula (IId):

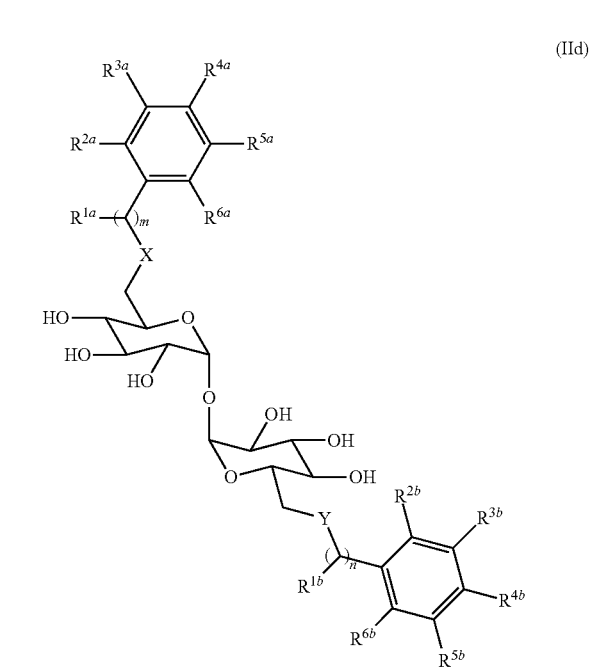

(IId)

or a pharmaceutically acceptable salt thereof, wherein:
m is 1;
n is 1;
X and Y are each independently selected from —C(O)O—, —C(O)NR$^a$—, —C(S)NR$^b$—, —NR$^c$—, and —O—;
R$^a$, R$^b$, and R$^c$ are each independently selected from hydrogen and $C_1$-$C_4$alkyl;
R$^{1a}$ and R$^{1b}$, when present, are each independently selected from hydrogen and $C_1$-$C_4$alkyl; and
R$^{2a}$, R$^{2b}$, R$^{3a}$, R$^{3b}$, R$^{4a}$, R$^{4b}$, R$^{5a}$, R$^{5b}$, R$^{6a}$, and R$^{6b}$ are each independently selected from hydrogen, $C_1$-$C_8$alkyl, hydroxy, $C_1$-$C_8$alkoxy, halo, $C_1$-$C_4$haloalkyl, aryl, $C_1$-$C_8$alkoxy-$C_1$-$C_8$alkoxy, $C_1$-$C_8$alkoxy-$C_1$-$C_8$alkyl, and hydroxy-$C_1$-$C_8$alkyl.

Clause 94. The compound of clause 93, wherein $R^{1a}$ and $R^{1b}$ are each hydrogen.

Clause 95. The compound of clause 93 or clause 94, wherein $R^{2a}$, $R^{2b}$, $R^{4a}$, $R^{4b}$, $R^{6a}$, and $R^{6b}$ are each independently selected from hydrogen, hydroxy, and $C_1$-$C_4$alkoxy; and $R^{3a}$, $R^{3b}$, $R^{5a}$, and $R^{5b}$ are each independently selected from hydrogen and $C_1$-$C_8$alkoxy.

Clause 96. The compound of any one of clauses 93-95, wherein X and Y are each —C(O)O—.

Clause 97. A compound of formula (IIe):

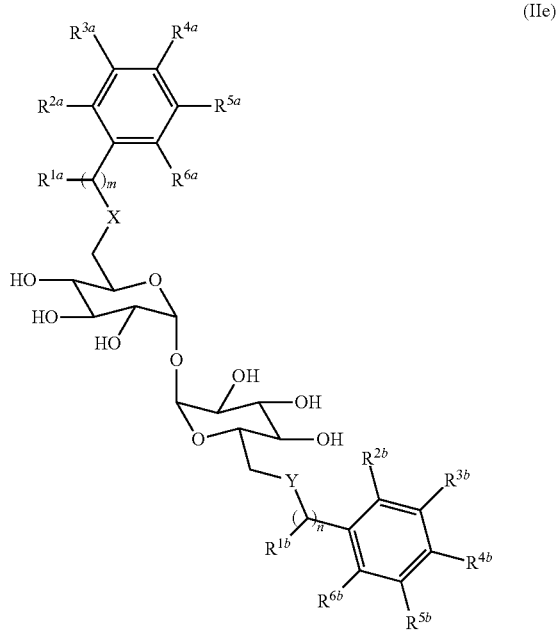

(IIe)

or a pharmaceutically acceptable salt thereof, wherein:
m is 0 or 1;
n is 0 or 1;
X and Y are each independently selected from —C(O) O—, —C(O)NR$^a$—, —C(S)NR$^b$—, —NR$^c$—, and —O—;
$R^a$, $R^b$, and $R^c$ are each independently selected from hydrogen and $C_1$-$C_4$alkyl;
$R^{1a}$ and $R^{1b}$, when present, are each independently selected from hydrogen and $C_1$-$C_4$alkyl;
$R^{2a}$, $R^{2b}$, $R^{5a}$, $R^{5b}$, $R^{6a}$, and $R^{6b}$ are each hydrogen; and
$R^{3a}$, $R^{3b}$, $R^{4a}$, and $R^{4b}$ are each independently selected from $C_1$-$C_8$alkyl, hydroxy, $C_1$-$C_8$alkoxy, $C_1$-$C_8$alkoxy-$C_1$-$C_8$alkoxy, $C_1$-$C_8$alkoxy-$C_1$-$C_8$alkyl, and hydroxy-$C_1$-$C_8$alkyl.

Clause 98. The compound of clause 97, wherein $R^{3a}$, $R^{3b}$, $R^{4a}$, and $R^{4b}$ are each independently selected from hydroxy and $C_1$-$C_8$alkoxy.

Clause 99. The compound of clause 97 or clause 98, wherein m is 0 and n is 0.

Clause 100. The compound of any one of clauses 97-99, wherein X and Y are each —C(O)O—.

Clause 101. A compound selected from the group consisting of:

6,6'-bis(3,5-dimethoxybenzoyl)-α,α-D-trehalose, and
6,6'-bis(2-hydroxy-3,5-di-tert-butylbenzoyl)-α,α-D-trehalose,
or a pharmaceutically acceptable salt thereof.

Clause 102. A compound that is 6,6'-bis(3,5-dimethoxybenzoyl)-α,α-D-trehalose, or a pharmaceutically acceptable salt thereof.

Clause 103. A compound that is 6,6'-bis(2-hydroxy-3,5-di-tert-butylbenzoyl)-α,α-D-trehalose, or a pharmaceutically acceptable salt thereof.

Clause 104. An adjuvant composition comprising an effective amount of a compound of any one of clauses 63-103, or a pharmaceutically acceptable salt thereof.

Clause 105. A method for inducing an enhanced immune response in a subject, comprising administering to the subject the adjuvant composition of clause 104.

Clause 106. A vaccine composition comprising: (a) an antigen; and (b) an adjuvant composition comprising an effective amount of a compound of any one of clauses 63-103, or a pharmaceutically acceptable salt thereof.

Clause 107. A method for inducing or enhancing immunogenicity of an antigen in a subject, comprising administering to the subject a vaccine composition comprising the antigen and an adjuvant composition comprising an effective amount of a compound of any one of clauses 63-103, or a pharmaceutically acceptable salt thereof.

Clause 108. An immunomodulatory composition comprising an effective amount of a compound of any one of clauses 63-103, or a pharmaceutically acceptable salt thereof.

Clause 109. A method of modulating an immune response in a subject, comprising administering to the subject the immunomodulatory composition of clause 108.

Clause 110. The method of clause 109, wherein the immunomodulatory composition is administered as a monotherapy.

Clause 111. The method of clause 109 or clause 110, wherein the immune response in the subject is increased.

Clause 112. The method of any one of clauses 109-111, wherein the subject is suffering from cancer, an autoimmune disorder, or an infectious disease.

What is claimed is:
1. A compound selected from the group consisting of:
6,6'-bis(3,5-diethoxybenzoyl)-α,α-D-trehalose,
6,6'-bis(2-hydroxy-3,5-di-tert-butylbenzoyl)-α,α-D-trehalose,
6,6'-bis(3,5-dipentyloxybenzoyl)-α,α-D-trehalose,
6,6'-bis(3,4,5-triethoxybenzoyl)-α,α-D-trehalose, and
6,6'-bis(2,6-hydroxy-3,5-di-tert-butylbenzoylamino)-α,α-D-trehalose,
or a pharmaceutically acceptable salt thereof.

2. An adjuvant composition comprising an effective amount of a compound of claim 1, or a pharmaceutically acceptable salt thereof.

3. A vaccine composition comprising: (a) an antigen; and (b) an adjuvant composition comprising an effective amount of a compound of claim 1, or a pharmaceutically acceptable salt thereof.

4. The compound of claim 1, or a pharmaceutically acceptable salt thereof, wherein the compound is 6,6'-bis(3,5-diethoxybenzoyl)-α,α-D-trehalose.

5. A vaccine composition comprising: (a) an antigen; and (b) an adjuvant composition comprising an effective amount of the compound of claim 4, or a pharmaceutically acceptable salt thereof.

6. The compound of claim 1, or a pharmaceutically acceptable salt thereof, wherein the compound is 6,6'-bis(2-hydroxy-3,5-di-tert-butylbenzoyl)-α,α-D-trehalose.

7. A vaccine composition comprising: (a) an antigen; and (b) an adjuvant composition comprising an effective amount of the compound of claim 6, or a pharmaceutically acceptable salt thereof.

8. The compound of claim 1, or a pharmaceutically acceptable salt thereof, wherein the compound is 6,6'-bis(3,5-dipentyloxybenzoyl)-α,α-D-trehalose.

9. A vaccine composition comprising: (a) an antigen; and (b) an adjuvant composition comprising an effective amount of the compound of claim 8, or a pharmaceutically acceptable salt thereof.

10. The compound of claim 1, or a pharmaceutically acceptable salt thereof, wherein the compound is 6,6'-bis(3,4,5-triethoxybenzoyl)-α,α-D-trehalose.

11. A vaccine composition comprising: (a) an antigen; and (b) an adjuvant composition comprising an effective amount of the compound of claim 10, or a pharmaceutically acceptable salt thereof.

12. The compound of claim 1, or a pharmaceutically acceptable salt thereof, wherein the compound is 6,6'-bis(2,6-hydroxy-3,5-di-tert-butylbenzoylamino)-α,α-D-trehalose.

13. A vaccine composition comprising: (a) an antigen; and (b) an adjuvant composition comprising an effective amount of the compound of claim 12, or a pharmaceutically acceptable salt thereof.

14. A compound selected from the group consisting of:

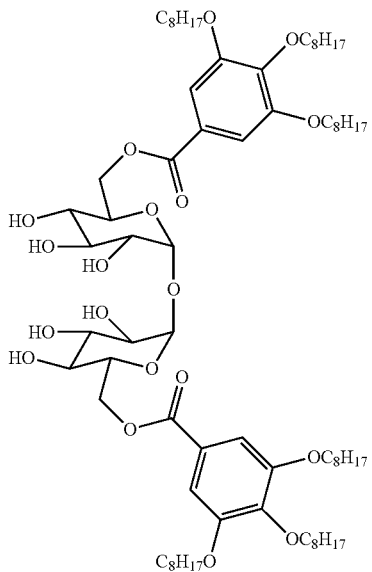

1098 and 6,6'-bis(2-hydroxy-3,5-di-tert-butylbenzoylamino)-α,α-D-trehalose, or a pharmaceutically acceptable salt thereof.

15. The compound of claim 14, or a pharmaceutically acceptable salt thereof, wherein the compound is

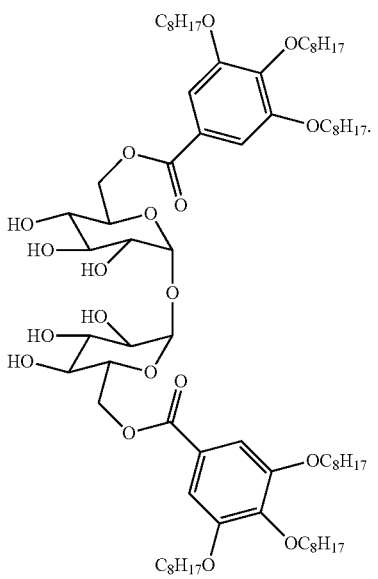

1098

16. A vaccine composition comprising: (a) an antigen; and (b) an adjuvant composition comprising an effective amount of the compound of claim 15, or a pharmaceutically acceptable salt thereof.

17. The compound of claim 14, or a pharmaceutically acceptable salt thereof, wherein the compound is 6,6'-bis(2-hydroxy-3,5-di-tert-butylbenzoylamino)-α,α-D-trehalose.

18. A vaccine composition comprising: (a) an antigen; and (b) an adjuvant composition comprising an effective amount of the compound of claim 17, or a pharmaceutically acceptable salt thereof.

19. An adjuvant composition comprising an effective amount of a compound of claim 14, or a pharmaceutically acceptable salt thereof.

\* \* \* \* \*